(12) United States Patent
Kim et al.

(10) Patent No.: US 7,582,426 B2
(45) Date of Patent: *Sep. 1, 2009

(54) METHOD FOR EXPRESSION OF PROTEINS ON SPORE SURFACE

(75) Inventors: June-Hyung Kim, Seoul (KR);
Byung-Gee Kim, Seoul (KR);
Soo-Keun Choi, Daejon (KR);
Heung-Chae Jung, Daejon (KR);
Jae-gu Pan, Daejon (KR)

(73) Assignee: Geneofocus Co., Ltd., Daejon (KR)

( * ) Notice: Subject to any disclaimer, the term of this patent is extended or adjusted under 35 U.S.C. 154(b) by 555 days.

This patent is subject to a terminal disclaimer.

(21) Appl. No.: 10/433,577

(22) PCT Filed: Dec. 7, 2001

(86) PCT No.: PCT/KR01/02124

§ 371 (c)(1),
(2), (4) Date: Jun. 5, 2003

(87) PCT Pub. No.: WO02/46388

PCT Pub. Date: Jun. 13, 2002

(65) Prior Publication Data

US 2004/0171065 A1  Sep. 2, 2004

(30) Foreign Application Priority Data

Dec. 8, 2000  (KR) .......................... 2000-0074835

(51) Int. Cl.
*C12Q 1/68* (2006.01)
*C12N 9/36* (2006.01)
*C12N 1/14* (2006.01)

(52) U.S. Cl. .......................... 435/6; 435/254.1; 435/207

(58) Field of Classification Search .................. 435/6, 435/254.1, 207
See application file for complete search history.

(56) References Cited

U.S. PATENT DOCUMENTS

| 5,766,914 | A | * | 6/1998 | Deits | .......................... | 435/207 |
| 5,800,821 | A | * | 9/1998 | Acheson et al. | .......... | 424/200.1 |
| 2004/0180348 | A1 | * | 9/2004 | Pan et al. | ........................ | 435/6 |

OTHER PUBLICATIONS

Sacco et al. , Journal of Bacteriology, vol. 177, No. 2, pp. 372-377, Jan. 1995.*
Nacelerio et al., "Bacillus subtilis Spore Coat Assembly Requires CotH Gene Expression", Journal of Bacteriology, vol. 178, No. 15, pp. 4375-4380, Aug. 1996.*
Bauer et al., "Functional Regions of the Bacillus subtilis Spore Coat Morphogenic Protein CotE", Journal of Bacteriology, vol. 181, No. 22, pp. 7043-7051, Nov. 1999.*
Ichikawa et al., "Combined action of transcription factors regulates genes encoding spore coat proteins of Bacillus subtilis", J. Biological Chemistry; May 2000; vol. 275, No. 18; pp. 13849-13855.

* cited by examiner

*Primary Examiner*—Robert Mondesi
*Assistant Examiner*—Khatol Shahnan-Shah
(74) *Attorney, Agent, or Firm*—Nixon & Vanderhye P.C.

(57) ABSTRACT

The present invention relates to a method for display of proteinson spore surface and a method for improving protein with rapidity using the same, which comprises the steps of (i) preparing a vector for spore surface display comprising a gene construct containing a gene encoding spore coat protein and a gene encoding a protein of interest, wherein, when expressed, the gene construct expresses a fusion protein between the spore coat protein and the protein of interest, (ii) transforming a host cell with the vector for spore surface display; (iii) displaying the protein of interest on a surface of a spore of the host cell; and (iv) recovering the spore displaying on its surface the protein of interest.

6 Claims, 15 Drawing Sheets

US 7,582,426 B2

METHOD FOR EXPRESSION OF PROTEINS ON SPORE SURFACE

This application is the U.S. national phase of international application PCT/KR01/02124 filed Dec. 7, 2001 which designated the U.S.

FIELD OF THE INVENTION

The present invention relates to a method for display of proteins on spore surface, in particular to a method for surface display using spore coat proteins as surface display motif and a high throughput method for improving protein.

DESCRIPTION OF THE RELATED ART

The technology of surface display in which organism displays on its surface the desired proteinaceous substance such as peptide and polypeptide has wider application fields depending on the types of protein displayed or host organism (Georgiou et al., 1993, 1997; Fischetti et al., 1993; and Schreuder et al., 1996). The gene of protein to be displayed is contained in host organism and thus the host can be selectively screened using the characteristics of the protein displayed, thereby obtaining the desired gene from the selected host with easiness. Therefore, such surface display technology can guarantee a powerful tool on molecular evolution of protein (see WO 9849286; and U.S. Pat. No. 5,837,500).

High-Throughput Screening

For instance, phage displaying on its surface antibody having desired binding affinity is bound to immobilized antigen and then eluted, followed by propagating the eluted phage, thereby yielding the gene coding for target antibody from phage (U.S. Pat. No. 5,837,500). The bio panning method described above can provide a tool to select target antibody by surface displaying antibody library on phage surface in large amount and comprises the consecutive steps as follows: (1) constructing library; (2) surface displaying the library; (3) binding to immobilized antigen; (4) eluting the bound phage; finally (5) propagating selected clones.

The technology of phage surface display has been found to be useful in obtaining the desired monoclonal variant form enormous library (e.g., $10^6$-$10^9$ variants) and thus applied to the field of high-throughput screening of antibody. Antibody has been used in various fields such as therapy, diagnosis, analysis, etc. and thus its demand has been largely increased. In this context, there has been a need for novel antibody to have binding affinity to new substance or catalyze biochemical reaction. The hybridoma technology to produce monoclonal antibody has been conventionally used so as to satisfy the need. However, the conventional method needs high expenditure and long time for performance whereas the yield of antibody is very low. In addition to this, to screen novel antibody, more than $10^{10}$ antibody libraries is generally used, as a result, the hybridoma technology has been thought to be inadequate in finding antibody exhibiting new binding property.

Many researches has focused on novel methods which is easier and more effective that the bio panning method described above and then developed novel technologies performed in such a manner that libraries are displayed on surface of bacteria or yeast and then cells displaying target protein is sorted with flow cytometry in a high-throughput manner. According to the technology, antigen labeled with fluorescent dye is bound to surface-displaying cell and the antibody having the desired binding affinity is isolated with flow cytometry capable of analyzing more than $10^8$ cells a hour. Francisco, et al., have demonstrated the usefulness of microbial display technology by revealing that surface-displayed monoclonal antibody could be concentrated with flow cytometry at rate of more than $10^5$, finally more than 79% have been proved to be the desired cells (Daugherty et al., 1998).

Live Vaccine

The surface display technology mentioned above can display antigen or fragment thereof and hence provide a delivery system for recombinant live vaccine. Up to now, attenuated pathogens or viruses have been predominantly employed as vaccine. Particularly, the bacteria have been found to express antigen intracellularly or extracellularly or on its cell membrane, thereby delivering antigen to host cell. The surface-displayed live vaccine induces a potential immune reaction and expresses continuously antigen during propagation in host cell; therefore, it has been highlighted as novel delivery system for vaccine. In particular, pathogen-derived antigenic epitope displayed on surface of nonpathogenic *E. coli* or *Salmonella* is administered orally in viable form and then exhibits to induce immune reaction in more continuous and powerful manner (Georgiou et al., 1997; and Lee et al., 2000).

Whole Cell Bioconversion

Whole cell as biocatalyst displaying on its surface enzyme capable of catalyzing chemical reaction can avoid necessities for direct expression, isolation and stabilization of enzyme. In case of expressing enzyme in cell for bioconversion, the cell is compelled to recovery and chemical (e.g., toluene) treatment to ensure impermeability of substrate. In addition, the lasting use renders the enzyme inactive or gives a problem on transference of substrate and product, thus dropping the productivity of overall process.

The above-mentioned shortcomings can be removed using enzyme displayed on cell surface (Jung et al, 1998a: 1998b) With whole cell displaying on its surface phosphodiesterase, organophosphorous-typed parathion and paraoxon with higher toxicity can be degraded, which is a typical example representing the applicability of cells displaying enzyme to environmental purification process (Richins et al., 1997).

Antipeptide Antibody

Martineau et al. have reported a highly simple method for production of antipeptide antibody using surface display technology of *E. coli* (Martineau et al., 1991). As described, the desired peptide is displayed on the protruding region of MalE and outer membrane protein, LamB and then whole cell or fragmented cell is administered to animal so as to generate antipeptide antibody. The method makes it possible to produce antibody with avoiding chemical synthesis of peptide and its linkage to carrier protein.

Whole Cell Absorber

To immobilize antibody or polypeptide on suitable carrier, which is useful in absorption chromatography, several subsequent steps must be performed, for example, protein production by fermentation, isolation of protein in pure form, and immobilization on a carrier. Generally, it is difficult to prepare the bioabsorber.

As absorber, a whole cell displaying absorption protein has been developed. The whole cell absorber known mostly is *Staphylococcus aureus* displaying on its surface protein A naturally, which has a high binding affinity to Fc domain of mammalian antibody. Currently, novel method has been proposed to remove and recover heavy metals, which employs metallothionein or metal-absorption protein displayed on microbial cell surface in large amount (Sousa et al., 1996, 1998; and Samuelson et al., 2000). The method is more effective in removing and recovering heavy metals from contamination source in comparison with the conventional method using metal-absorption microbes.

As understood based on the matters described above, in order to display foreign protein on cell surface, a suitable surface protein and foreign protein must be linked each other in gene level to express fusion protein, and the fusion protein should pass stably across inner membrane of cell to be attached to cell surface. Preferably, the surface protein having the following characteristics is recommended as surface display motif: 1) existence of secretory signal enabling passage across inner membrane of cell, 2) existence of target signal enabling stable attachment to cell surface, 3) high expression level on cell surface, and 4) stable expression regardless of protein size (Georgiou et al., 1993).

Therefore, the surface display motif or novel recombinant protein, which meets the requirements described above, should be selected or prepared to develop novel surface display system overcoming disadvantages of the known systems. In addition, the selection of a suitable host cell to display is very pivotal.

Up to date, the developed surface display systems are as follows: phage surface display system (Chiswell and McCarferty, 1992), bacterial surface display system (Georgiou et al., 1993; Little et al., 1993; and Georgiou et al., 1997), surface display system of Gram negative bacteria (Francisco et al., 1992; Fuchs et al., 1991; Klauser et al., 1990, 1992; and Hedegaard et al., 1989), surface display system of Gram positive bacteria (Samuelson et al., 1995; Palva et al., 1994; and Sleytr and Sara, 1997), and surface display system of yeast (Ferguson, 1988; and Schreuder et al., 1996).

In the developed phage display system, the concentration of the desired clone from phage library has been found to be difficult and the antibody selected from phage library displaying has usually exhibited very low expression rate. According to a surface display system of Gram negative bacteria, the incorporation of foreign polypeptide into surface structure results in not only its steric limitation which makes it impossible to have stable membrane protein (Charbit et al., 1987; and Agterberg et al., 1990) but also drop of the stability of cell outer membrane and its viability. In addition, in surface display system of yeast, because the vector used has usually shown a low rate of transformation, which is unfavorable to surface display of library.

The surface display systems developed have been cooperatively used each other. For example, to screen antibody variant with enhanced binding affinity, a primary screening is performed using phage surface display system and additionally, the secondary screening is carried out using cell surface display system (Georgiou, 2000). However, the phage display technology is encountered to difficulty in concentration of the desired clones from phage library. The reason is that the antibody displayed on phage surface does not show the elution pattern depending exactly on its binding affinity, which is ascribed to avidity of antibody displayed on phage surface. Therefore, there remains a need of novel methods ensuring screening the desired antibody from antibody library.

*E. coli* as display host, which has been intensively studied, uses generally cell outer membrane protein as surface display motif. However, the over-expression of cell outer membrane protein fused to foreign protein is likely to bring about structural instability of cell outer membrane, consequently, diving the viability of host cell (Georgiou et al., 1996). To be from the shortcomings, ice-nucleation protein with no effect on viability has been used as display motif, and has been applied to bioconversion process, surface display of enzyme library and screening enzyme variants (Jung et al., 1998a, 1998b; and Kim et al., 1998, 1999, 2000).

The size of library displayed on surface depends on the transformation efficiency of host cell with vector; thus *E. coli* as host has an advantage in view of the size of library to be displayed. Gram positive bacteria as host are relatively rigid and permit stable display of the desired protein; however, transformation efficiency is exhibited low, which results in smaller size of library than *E. coli*.

The host organisms having been developed are likely to be sensitive to a variety of physiochemical treatments, which makes it impossible to select proteins displayed on surface by virtue of direct physiochemical treatment. For example, in screening a variant of antibody with enhanced binding affinity, abrupt change of pH or adjustment of the concentration of base is generally performed to elute the variant, which are found to decrease the viability of phage or bacteria in medium.

In addition, the host organisms used conventionally have a complicated and weak structure of cell surface, which drops adaptability to extreme environment such as high temperature and high pressure. To employ *E. coli* displaying on its surface enzyme in bioconversion reaction, the cells must have represent stability in bioconversion system. In this context, the surface of *E. coli* displaying on, its surface enzyme is generally subject to immobilization, which does not lead to satisfying results (Freeman et al., 1998).

As described above, the known surface display technologies, based on applying fields, have used bacteriophage, Gram negative or positive bacterium, yeast, cilium or mammalian cell as host organism and surface proteins of each organism as surface display motif. However, in the surface display methods having been developed, the host organism does not have resistance to chemicals and physiochemical change such as pH change, and displaying protein on its surface in excess leads to disadvantages in cell surface, finally reducing the viability of host cell largely (Georgiou et al., 1996).

DETAILED DESCRIPTION OF THIS INVENTION

Under such situation, the present inventors have made intensive studies to be from the shortcoming of conventional display methods, and as a result, we have developed novel display system using a spore as host and a coat protein as motif of surface display. Surprisingly, the developed display system has been found to have excellent stability to a variety of physiochemical stresses in surrounding environment and have much broader applicability.

Accordingly, it is an object of this invention to provide a method for displaying a protein of interest on spore surface using a system for spore surface display.

It is another object of this invention to provide a method for improving a protein of interest using a system for spore surface display.

It is still another object of this invention to provide a method for bioconversion using a system for spore surface display.

It is further object of this invention to provide a method for preparing protein microarray using a system for spore surface display.

It is still further object of this invention to provide a method producing an antibody to antigen in vertebrates using a system for spore surface display.

It is another object of this invention to provide a method for preparing a whole cell absorber using a system for spore surface display.

It is still another object of this invention to provide a microbial transformant for spore surface display of a protein of interest.

It is further object of this invention to provide a spore for spore surface display of a protein of interest.

It is still further object of this invention to provide a vector for spore surface display.

The principle of the present invention lies in the employment of microbial spore as host for surface display and spore coat protein as surface display motif. The present inventors have been compelled to select a system for spore surface display since the spore has a following advantages (Driks, 1999): 1) a higher heat stability, 2) a significant stability to radioactivity, 3) a stability to toxins, 4) a higher stability to acid and base, 5) a significant stability to lysozyme, 6) a resistance to dryness, 7) a higher stability to organic solvents, 8) a fusion protein between a surface display motif and a protein of interest is displayed on spore surface immediately after expression without secretion in host cell, 9) no metabolic activity, and 10) shorter time for obtaining spore, e.g. within several hours.

In particular, the spore coat proteins used in this invention circumvent a necessity for passage across cell membrane, so that they do not need secretion signal and target signal which are prerequisites of surface display motif, thereby ensuring a surface display of protein such as β-galactosidase, in orderly fashion, which is difficult to pass across cell membrane.

U.S. Pat. No. 5,766,914 discloses a method of producing and purifying enzymes using fusion protein between cotC or cotD among spore coat proteins of Bacillus subtilis and lacZ as reporter. However, as disclosed, a purification method for demonstrating surface display of protein is not recognized to isolate spores specifically. Furthermore, the activity of enzyme expressed has been very low and the display of enzyme on spore surface has never been demonstrated by means of reliable methods such as biochemical, physical and immunological methods. In addition to this, the inner coat protein, cotD is enclosed by outer coat protein of 70-200 nm thickness, which makes it difficult to be exposed to spore surface. In case of fusion protein expression using outer coat protein, cotC, the activity of enzyme is increased by four-fold in comparison with that of cotD; however, the activity, 0.02 U, is considered negligible, in particular, in consideration of industrial scale. Therefore, the matter disclosed in the document above cannot be considered to use and recognize a system for spore surface display. In other words, the patent document cannot be recognized to describe a system for spore surface display. U.S. Pat. Nos. 5,837,500 and 5,800,821 also indicate cotC and cotD as a preferable surface display motif, and therefore the patent documents cannot be recognized to describe a system for spore surface display because of the reasons mentioned above.

Furthermore, according to the purification method of spore proposed in U.S. Pat. No. 5,766,914, half of the purified resultant has been observed under microscope to have the complex forms between cells harboring spores and cell-lysis matters bound to spores (see FIG. 1; cells with blackish color and long side are those not forming spore and spores is observed to be white and circular), which has been demonstrated by the present inventors. The facts hereinabove reveals possibility to bring about the false results by measuring of the activity of reporter enzyme or analyzing of reporter enzyme with flow cytometry in vegetative cells rather than on spore surface. In contrast, the renografin gradient centrifugation as demonstrated in Examples below allows for the perfect purification of spores (see FIG. 2), thereby measuring the activity of enzyme displayed on spore surface solely.

Observations on lower enzyme activity in several documents including the patents above are likely to be resulted from the following reasons. First, it is suggested that the expression level of coat protein itself is low. The maximum expression levels of CotC and CotD are 40 and 147 Miller Units, respectively, which is considered to be largely low, in particular, in consideration of CotE of 6021 Miller Units (Zheng L and Losick R., J. Mol. Biol. 212:645-660(1990)). Furthermore, it is notable that the amount of enzyme displayed on spore surface has not been reported. Secondly, it is possible that the protein displayed on spore surface is cleaved by protease in host cell. Such suggestion is made based on the fact that at spore-forming stage of Bacillus subtilis a variety of proteases are expressed and reconstitution for spore formation is occurred. The suggestion can be demonstrated in Examples below in which a variant lack protease exhibits a much higher enzyme activity displayed on spore surface (see FIG. 7).

Using gene of GFP (green fluorescence protein) as reporter linked to cotE and spoIVA, the studies on gene expression and localization of the expressed protein in spore has been attempted (Webb et al., 1995; Lewis et al., 1996). The publications disclose that the fusion protein expressed is found in spore by means of observation under fluorescence microscope using fluorescence of GFP; however, they never describe if the fusion protein is displayed and linked on spore surface.

As another example of spore surface display using coat protein, U.S. Pat. No. 5,800,821 discloses a spore as delivery system of antigen. However, the publication does not disclose that the antigen expressed is displayed on spore surface and the spore containing antigen administered can induce immunization reaction in host.

The present inventors have recognized the shortcomings of the conventional arts described above and developed an efficient and optimized system for spore surface display, which have been confirmed by enzymological, immunological and physiochemical methods using various spore coat proteins.

In one aspect of this invention, there is provided a method for displaying a protein of interest on spore surface, which comprises the steps of: (i) preparing a vector for spore surface display comprising a gene construct containing a gene encoding spore coat protein and a gene encoding a protein of interest, wherein, when expressed, the gene construct expresses a fusion protein between the spore coat protein and the protein of interest; (ii) transforming a host cell with the vector for spore surface display; (iii) displaying the protein of interest on a surface of a spore of the host cell; and (iv) recovering the spore displaying on its surface the protein of interest.

In another aspect of this invention, there is provided a method for improving a protein of interest, which comprises the steps of: (i) constructing a gene library of the protein of interest; (ii) preparing a vector by linking the gene library to a gene encoding spore coat protein; (iii) transforming a spore-forming host cell with the vector; (iv) forming a spore in the transformed host cell and displaying the protein of interest on a surface of the spore; (v) recovering the spore displaying on its surface the protein of interest; and (vi) screening the spore displaying a variant of the protein of interest having a desired property.

In still another aspect of this invention, there is provided a method for improving a protein of interest using a resistance property of spore, which comprises the steps of: (i) constructing a gene library of the protein of interest; (ii) preparing a vector by linking the gene library to a gene encoding spore coat protein; (iii) transforming a spore-forming host cell with the vector; (iv) forming a spore in the transformed host cell and displaying the protein of interest on a surface of the spore; (v) treating the spore displaying on its surface the protein of interest with one or more selected from the group consisting of organic solvent, heat, acid, base, oxidant, dryness, surfactant and protease; (vi) recovering the spore displaying on its surface the protein of interest; and (vii) screening the spore displaying a variant of the protein of interest having a resistance to the treatment.

In further aspect of this invention, there is provided a method for bioconversion, which comprises the steps of: (i) preparing a vector for spore surface display comprising a gene construct containing a gene encoding spore coat protein and a gene encoding a protein of interest conducting a bioconversion reaction, wherein, when expressed, the gene construct expresses a fusion protein between the spore coat protein and the protein of interest; (ii) transforming a host cell with the vector for spore surface display; (iii) displaying the protein of interest on a surface of a spore of the host cell; (iv) recovering the spore displaying on its surface the protein of interest; and (v) performing the bioconversion reaction using the spore displaying on its surface the protein of interest.

In still further aspect of this invention, there is provided a method for preparing protein microarray, which comprises the steps of: (i) preparing a vector for spore surface display comprising a gene construct containing a gene encoding spore coat protein and a gene encoding antibody or antigen having binding affinity to a protein to be analyzed, wherein, when expressed, the gene construct expresses a fusion protein between the spore coat protein and the antibody or antigen; (ii) transforming a host cell with the vector for spore surface display; (iii) displaying the antibody or antigen on a surface of a spore of the host cell; (iv) recovering the spore displaying on its surface the antibody or antigen; and (v) immobilizing onto a solid surface the spore displaying on its surface the antibody or antigen.

In another aspect of this invention, there is provided a method producing an antibody to antigen in vertebrates, which comprises the steps of: (i) preparing a vector for spore surface display comprising a gene construct containing a gene encoding spore coat protein and a gene encoding the antigen, wherein, when expressed, the gene construct expresses a fusion protein between the spore coat protein and the antigen; (ii) transforming a host cell with the vector for spore surface display; (iii) displaying the antigen on a surface of a spore of the host cell; (iv) recovering the spore displaying on its surface the antigen; and (v) administering to vertebrates a composition containing an immunologically effective amount of the spore displaying on its surface the antigen.

In still another aspect of this invention, there is provided a method for preparing a whole cell absorber, which comprises the steps of: (i) preparing a vector for spore surface display comprising a gene construct containing a gene encoding spore coat protein and a gene encoding a protein having a binding affinity to a certain substance, wherein, when expressed, the gene construct expresses a fusion protein between the spore coat protein and the protein; (ii) transforming a host cell with the vector for spore surface display; (iii) displaying the protein on a surface of a spore of the host cell; (iv) recovering the spore displaying on its surface the protein; and (v) immobilizing onto a carrier the spore displaying on its surface the protein.

According to preferred embodiments of this invention, the gene encoding spore coat protein is derived from a spore-forming Gram negative bacterium including Myxococcus; a spore-forming Gram positive bacterium including *Bacillus*; a spore-forming Actionmycete; a spore-forming yeast including *Saccharomyces cerevisiae*, Candida and Hansenulla or a spore-forming fungus, but not limited to. More preferably, the gene encoding spore coat protein is derived from a spore-forming Gram positive bacterium, most preferably, *Bacillus* including *Bacillus subtilis* and *Bacillus polymyxa*, etc.

The gene of spore coat protein useful in this invention includes cotA, cotB, cotC, cotD (W. Donovan et al., *J. Mol. Biol.*, 196:1-10(1987)), cotE (L. Zheng et al., *Genes & Develop.*, 2:1047-1054(1988)), cotF (S. Cutting et al., *J. Bacteriol.*, 173:2915-2919(1991)), cotG, cotH, cotJA, cotJC, cotK, cotL, cotM, cotS, cotT (A. Aronson et al., *Mol. Microbiol.*, 3:437-444(1989)), cotV, cotW, cotX, cotY, cotZ (J. Zhang et al., *J. Bacteriol.*, 175:3757-3766(1993)), spoIVA, spoVID and sodA, but not limited to.

In addition, the gene encoding spore coat protein useful in this invention is a modified form or a recombinant form of one selected from the group consisting of cotA, cotB, cotC, cotD, cotE, cotF, cotG, cotH, cotJA, cotJC, cotK, cotL, cotM, cotS, cotT, cotV, cotW, cotX, cotY, cotZ, spoIVA, spoVID and sodA, in which the modified form or the recombinant form has a more compatibility for spore surface display relative to wild type genes. The modified form of the gene is obtained by DNA shuffling method (Stemmer, *Nature*, 370: 389-391 (1994)), StEP method (Zhao, H., et al., *Nat. Biotechnol.*, 16: 258-261 (1998)), RPR method (Shao, Z., et al., *Nucleic acids Res.*, 26: 681-683 (1998)), molecular breeding method (Ness, J. E., et al., *Nat. Biotechnol.*, 17: 893-896 (1999)), ITCHY method (Lutz S. and Benkovic S., *Current Opinion in Biotechnology*, 11: 319-324 (2000)), error prone PCR (Cadwell, R. C. and Joyce, G. F., *PCR Methods Appl.*, 2: 28-33 (1992)), point mutagenesis (Sambrook et al., *Molecular Cloning: A Laboratory Manual*, Cold Spring Harbor, N.Y., 1989), nucleotide mutagenesis (Smith M. *Annu. Rev. Genet.* 19: 423-462 (1985)), combinatorial cassette mutagenesis (Wells et al., Gene 34: 315-323 (1985)) and other suitable random mutagenesis.

Further to this, the gene encoding spore coat protein is selected from the group consisting of cotA, cotB, cotC, cotD, cotE, cotF, cotG, cotH, cotJA, cotJC, cotK, cotL, cotM, cotS, cotT, cotV, cotW, cotX, cotY, cotZ, spoIVA, spoVID and sodA, in which the gene has a substituted promoter for its promoter to enhance spore surface display relative to wild type genes. The promoter for enhancing surface display, for example, includes the promoters of cotE or cotG genes, which show higher expression level.

In preferred embodiments of this invention, the gene encoding spore coat protein is selected from the group consisting of cotA, cotE, cotF, cotG, cotH, cotJA, cotJC, cotK, cotL, cotM, cotS, cotT, cotV, cotW, cotX, cotY, cotZ, spoIVA, spoVID and sodA, more preferably, cotE or cotG and most preferably, cotG.

According to the present methods, as linking a gene of coat protein and a gene of the protein of interest, the overall sequence, fragments, two or more repeated sequences of the gene of coat protein are useful. In two or more repeated sequences, the repeated sequences may be the same or different each other. The overall sequence, two or more repeated sequences of the gene of the protein of interest are also useful in the fusion sequence. In two or more repeated sequences, the repeated sequences may be the same or different each other. Other combinations also may be useful in the fusion sequence.

It is understood by one skilled in the art that the gene construct may exist as plasmid in host cell independently or as integrated form into chromosome of host cell. Additionally, in the gene construct, it is recognized by one skilled in the art that the gene of coat protein may be followed or preceded by the gene of the protein of interests Integrated form into the counterpart gene may be useful.

It is recognized by one skilled in the art that the expression of the fusion protein between coat protein and protein of interest can be induced by virtue of promoters of coat protein gene and protein of interest or other suitable promoters inducible in host cell The present methods is applicable to any protein, for example, including enzyme, enzyme inhibitor, hormone, hormone analogue, hormone receptor, signal transduction protein, antibody, monoclonal antibody, antigen, attachment protein, structural protein, regulatory protein, toxin protein, cytokine, transcription regulatory protein, blood clotting protein, plant defense-inducing protein and fragments thereof. The applicable proteins include multimer as well as monomer. The surface display of multimeric proteins has been rarely reported, for instance, the surface display of alkaline phosphatase in *E. coli*, has resulted the display toward inner part of cell outer membrane (Stathopoulus et al., 1996). β-galactosidase used as reporter enzyme in Examples of the present invention must form tetramer to exhibit its activity and has not been published to be successful in surface display. β-galactosidase generally cannot pass across cell membrane and comprises an amino acid sequence detrimental to cell membrane, as a result, the fusion protein between surface display motif and β-galactosidase has been recognized not to be displayed on cell surface. Therefore, the surface display of β-galactosidase described in Examples proves to be surprising.

The term used herein "protein" refers to molecule consisting of peptide bond, for example including oligopeptide and polypeptide.

The host cell suitable in this invention, includes spore-forming Gram negative bacterium including Myxococcus, a spore-forming Gram positive bacterium including *Bacillus*, a spore-forming Actionmycete, a spore-forming yeast and a spore-forming fungus, but not limited to. Preferably, the host cell is a spore-forming Gram positive bacterium, more preferably, *Bacillus*. In particular, *Bacillus subtilis* is advantageous in the senses that genetic knowledge and experimental methods on its spore forming as well as culturing method are well known.

According to the present methods, the spore may be reproductive or non-reproductive. In the method for improving a protein, the recovered coats are subject to reproduction but the methods using a spore as delivery means of protein of interest obviate the necessity for reproduction of spore. It is considerable that the organisms genetically engineered is likely to be regulated under laws and rules; hence non-reproductive spore is preferable. For example, *Bacillus subtilis* lack of cwlD gene is preferably used due to being non-reproductive.

According preferred embodiments of this invention, the recovery of spore is performed in such a manner that the display of the protein of interest on the spore surface is maximized by controlling culture time, after which culturing is terminated and the spore is then recovered. Suitable culture time is varied depending upon the type of cell used, for example, in case of using *Bacillus subtilis* as host, the culture time of 16-25 hours is preferred.

In the present methods, the recovery of spore may be carried out according to the conventional methods known to one skilled in the art, more preferably, renografin gradients methods (C. R. Harwood, et al., "Molecular Biological Methods for *Bacillus*," John Wiley & Sons, New York, p. 416(1990)).

As demonstrated in Examples, the stability of spore displaying the foreign protein of interest an its surface is very high in the present invention, indicating maintenance of the integrity of spore surface structure formed by cooperation of coat proteins while the foreign protein is displayed.

The protein of interest displayed on spore surface according to the present methods can be demonstrated with a wide variety of methods as follows: 1) A primary antibody is bound to the protein of interest displayed on spore surface and then reacted with a secondary antibody labeled with fluorescent chemical to stain the spore, followed by observation with fluorescence microscope or analysis with flow cytometry. 2) The protein of interest displayed on spore surface is treated with protease, followed by measurement of the activity of the protein or detecting lower signal with fluorescence microscope or flow cytometry. 3) In case that the protein of interest uses a substrate with higher molecular weight, the direct measurement of the activity of the protein can provide the level of display since the substrate cannot pass across outer coat of spore.

In the method for improving protein, the construction of gene library for the protein of interest is performed by a mutagenesis of the gene encoding the protein of interest of wild type, in which the mutagenesis includes DNA shuffling method (Stemmer, *Nature*, 370: 389-391(1994)), StEP method (Zhao, H., et al., *Nat. Biotechnol.*, 16: 258-261 (1998)), RPR method (Shao, Z., et al., *Nucleic acids Res.*, 26: 681-683 (198)), molecular breeding method (Ness, J. E., et al., *Nat. Biotechnol.*, 17: 893-896 (1999)), ITCHY method (Lutz S. and Benkovic S., *Current Opinion in Biotechnology*, 11: 319-324 (2000)), error prone PCR (Cadwell, R. C. and Joyce, G. F., *PCR Methods Appl.*, 2: 28-33 (1992)), point mutagenesis (Sambrook et al., *Molecular Cloning: A Laboratory Manual*, Cold Spring Harbor, N.Y., 1989), nucleotide mutagenesis (Smith M. *Annu. Rev. Genet.* 19: 423-462 (1985)), combinatorial cassette mutagenesis (Wells et al., *Gene* 34: 315-323 (1985)) and other suitable random mutagenesis.

In the method for improving protein, the screening is performed in a rapid manner by means of measuring an activity of the protein or flow cytometry (Georgiou, 2000). In case of using an activity of the protein, the screening is carried out by measuring growth of host expressing the protein or colorimetrical reaction catalyzed by the protein. In the method for improving protein using a resistance property of spore, the screening is carried out in a rapid manner by virtue of measuring an activity of the protein or using the structural stability of the protein.

The methods for improving protein provide in a high-throughput manner, from wild type, 1) enzymes catalyzing non-biological reaction (e.g., Diels-Alder condensation), 2) enzymes with non-natural steroselectivity or regioselectivity, 3) enzymes with activity in organic solvent or organic solvent-aqueous solution two-phase system, and 4) enzymes with activity in extreme conditions such as high temperature or pressure.

In addition, to select a variant of antibody with enhanced binding affinity, it is general that pH is abruptly changed or the concentration of base is adjusted to elute the variant. In a method using phage or bacteria as carrier, such elution conditions are likely to decrease the viability of phage or bacteria in medium. However, the methods for improving protein using system of spore surface display overcome the drawback.

In the meantime, the bioconversion process using surface-displayed enzymes requires a physiochemical stability of surface displaying host in extreme conditions because the process is usually executed in high temperature and/or organic solvent. In particular, a chemical synthesis valuable in current industry is mainly carried out in organic solvent and the synthesis of chiral compound or the resolution of racemic mixture is also performed in highly severe physiochemical conditions. Therefore, the surface-displayed enzyme as well as the organisms displaying enzyme is compelled to have stability in such extreme conditions. In this connection, it is demonstrated that the methods for bioconversion using system for spore surface display is largely advantageous.

The chemical processes using surface-displayed enzymes have been proposed (Georgiou et al., 1993). However, the proposed processes have generally required immobilization of cell surface with cross-linking agent since the host displaying enzyme is very unstable during process (Freeman et al., 1996). The present bioconversion process is free from the disadvantage mentioned above. Because the surface-displayed enzyme as well as the host displaying enzyme is largely stable, the present method avoids the immobilization. In Examples described hereinafter, the bioconversion reaction with β-galactosidase is exemplified and thus it is understood by one skilled in the are that the present method can be also applied to any type of enzyme such as lipase, protease, cellulase, glycosyltransferase, oxidoreductase and aldolase. In addition, the present method is useful in single step or multi-step reaction and in aqueous or non-aqueous solution. The present bioconversion method employs spore as free or immobilized form and can be performed with other microbes or enzymes.

Similar to DNA microarray, a protein microarray provides means for analyzing expression or expression level of target protein in certain cell. In order to fabricate protein array, the suitable proteins to be arrayed must be obtained and then immobilized on solid surface. During analysis using protein array, washing step is necessarily performed to remove unbound proteins and various treatments such as high temperature, higher salt concentration and pH adjustment are executed; therefore, it is pivotal to guarantee proteinaceous substance with higher stability in such detrimental environment.

In addition, the conventional process for preparing protein array needs tedious and repetitive works such as cloning genes of several thousands to tens of thousands of proteins and immobilizing of the proteins expressed. Therefore, there remains a need to improve simplicity and rapidity of the works.

According to the method for preparing protein microarray of this invention, it is ensured that the works described-above cane be performed with much greater readiness. In the present method, a gene construct containing a gene encoding spore coat protein and a gene encoding the desired protein is introduced into host cell and the spore displaying on its surface the desired protein is isolated, followed by immobilization of the isolated spore onto a solid surface. In the me-hod for preparing protein array, the conventional steps may be used (see Wo 0061806, WO 0054046, U.S. Pat. No. 5,807,754, EP 0818467, WO 9742507, U.S. Pat. No. 5,114,674 and WO 9635953). The protein microarray manufactured by the present invention has a variety of applicable fields including diagnosis, analysis of gene expression, analysis of interaction between proteins, analysis of interaction between protein and ligand, study on metabolism, screening novel or improved enzymes, combinatorial biochemical synthesis and biosensor.

The solid substrate suitable in the present method includes, but not limited to, glasses (e.g., functionalized glasses), Si, Ge, GaAs, GaP, SiO, $SiN_4$, modified silicone nitrocellulose, polyvinylidene fluoride, polystylene, polytetrafluoroethylene, polycarbonate, nylon, fiber and combinations thereof.

The spore optionally may be attached to the array substrate through linker molecules. It is preferred that the regions of the array surface not being spotted are blocked. The amount of spores applied to each spot (or address) depends on the type of array. Interaction between the protein displayed on spore attached to solid substrate and the sample applied can be detected based on their inherent characteristics (e.g., immunogenicity) or can be rendered detectable by being labeled with an independently detectable tag (e.g., fluorescent, luminescent or radioactive molecules, and epitopes). The data generated with protein array of this invention can be analyzed using known computerized systems such as "reader" and "scanner".

According to the method producing an antibody of this invention, a composition containing an immunologically effective amount of the spore, preferably, further comprises adjuvant such as incomplete and complete Freund's adjuvants. In the present method, the mode of administration is, preferably, injection and more preferably, intravenous, intraperitoneal, subcutaneous and intramuscular injections. Boosting within suitable period after the first administration is preferable to yield a sufficient amount of antibody.

Meanwhile, in the process for preparing absorption chromatography, antibody or polypeptide is produced, purified and immobilized on a carrier. Generally, it is very difficult to prepare the bioabsorbers. The disadvantage may be overcome using whole cell displaying protein as described in Georgiou et al., 1997. Therefore, the system for spore surface display of this invention provides a whole cell absorber to solve the problems of the known absorbers.

In further aspect of this invention, there is provided a microbial transformant for spore surface display of a protein of interest, characterized in that the transformant is produced by transformation with a vector for spore surface display containing (i) a gene encoding a protein of interest and (ii) a gene encoding spore coat protein is selected from the group consisting of cotA, cotB, cotC, cotD, cotE, cotF, cotG, cotH, cotJA, cotJC, cotK, cotL, cotM, cotS, cotT, cotV, cotW, cotX, cotY, cotZ, spoIVA, spoVID and sods, in which when expressed, a fusion protein between the spore coat protein and the protein of interest is expressed.

According to preferred embodiment, the transformant is derived from a variant mutated to enhance spore surface display. For example, the mutation to enhance spore surface display eliminates a production of extracellular secretory protease in the transformant, so that the protein of interest displayed on spore surface is stably maintained. In addition, the mutation to enhance spore surface display eliminates a production of intracellular protease in the transformant. It is also preferred that a gene or genes involved in spore forming is subject to mutation in order to the rate of spore forming (Perego, M., et al., *Mol. Microbiol.* 19: 1151-1157 (1996)).

In still further aspect of this invention, there is provide a spore for spore surface display of a protein of interest, characterized in that the spore displays the protein of interest on its surface.

According to the present invention, the spore may be reproductive or non-reproductive one which is selected based on its application field. Preferably, the non-reproductive spore can be obtained by virtue of one or more methods selected from the group consisting of genetic method (Popham D. L., et al., *J. Bacteriol.*, 181: 6205-6209 (1999)), chemical method (Setlow T. R., et al., *J. Appl. Microbiol.*, 89: 330-338 (2000)) and physical method (Munakata N, et al., *Photochem. Photobiol.*, 54: 761-768 (1991)). The genetic method to make the spore non-reproductive is accomplished by, for example, deleting a gene of host cell involved in reproduction of spore.

In the present invention, it is preferred that the spore is derived from a variant mutated to increase its agglutination property because in bioconversion performed in industrial scale, the separation between the resulting product and spores is rendered easier. The increase of the agglutination property in the spore is accomplished by one or more methods selected from the group consisting of genetic method, chemical method and physical method. As example of the physical method, the heat treatment can be proposed (Wiencek K. M., et. al., *Appl. Environ. Microbiol.,* 56: 2600-2605 (1990)).

In another aspect of this invention, there is provided a vector for spore surface display, characterized in that the vector comprises a replication origin, an antibiotic-resistance gene, a restriction site, a gene encoding a spore coat protein, a gene encoding a protein of interest and a promoter operatively linked to the gene encoding a spore coat protein, in which when expressed, a fusion protein between the spore coat protein and the protein of interest is expressed.

According to preferred embodiment, the gene encoding a spore coat protein is selected from the group consisting of cotA, cotB, cotC, cotD, cotE, cotF, cotG, cotH, cotJA, cotJC, cotK, cotL, cotM, cotS, cotT, cotV, cotW, cotX, cotY, cobZ, spoIYA, spoVID and sodA, more preferably, cotE or cotG, and most preferably, cotG.

In the vector of this invention, the replication origin can include various origins known to one skilled in the art, for example, when the vector is introduced into a spore-forming yeast, 2μ, ARS, ARS1 or ARS2 can be used as replication origin. In case of using *Bacillus* as host, ori 322, ColE1 origin, Rep1060, etc. can be used. The antibiotic-resistance gene used as selective marker, when prokaryote such as *Bacillus* is used as host, is a resistance gene to antibiotics acting to prokaryotes, for example, including kanamycin, ampicillin, carbenicillin, chloramphenicol, streptomycin, geneticin, neomycin and tetracycline. The promoter used in the present vector includes a promoter of the gene of spore coat protein and a known promoter operable in host cell.

The following specific examples are intended to be illustrative of the invention and should not be construed as limiting the scope of the invention as defined by appended claims.

EXAMPLES

Example I

Isolation of the Gene Encoding Coat Proteins

I-1: Construction of the Vector for Spore Surface Display

To isolate the most appropriate coat protein for spore surface display among coat proteins consisting of spore, the recombinant vector having the gene encoding a fusion protein between coat protein and β-galactosidase was constructed as follow:

To begin with, the DNA was extracted from the *Bacillus subtilis* 168 strain provided from Dr. F. Kunst (Kunst F., et al., *Nature,* 390: 249-256(1997)) by Kalman's method (Kalman S., et al., *Appl. Environ. Microbiol.* 59, 1131-1137(1993)), and the purified DNA was served as template for PCR to spoIVA primers (SEQ ID NOs: 1 and 2), cotB primers (SEQ ID NOs: 3 and 4), cotC primers (SEQ ID NOs: 5 and 6), cotD primers (SEQ ID NOs: 7 and 8), cotE primers (SEQ ID NOs: 9 and 10), cotG primers (SEQ ID NOs: 11 and 12), cotH primers (SEQ ID NOs: 13 and 14), cotM primers (SEQ ID NOs: 15 and 16), cotV primers (SEQ ID NOs: 17 and 18), cotX primers (SEQ ID NOs: 19 and 20) and cotY primers (SEQ ID NOs: 21 and 22). Taq polymerase purchased from Boehringer Mannheim was used for total 35 cycles of PCR under condition of denaturation for 30 sec at 94° C., annealing for 30 sec at 55° C. and extension for 1 min at 72° C.

Figure 1:
FIG. 1 is a microscopic photograph showing spores of *Bacillus subtilis* purified according to method described in U.S. Pat. No. 5,766,914.
Figure 2:
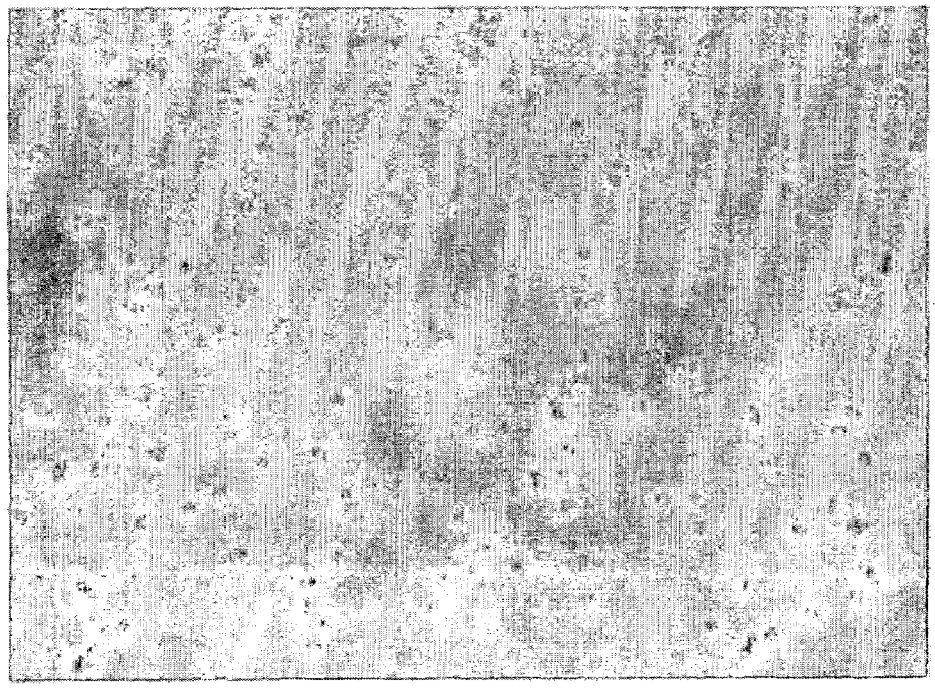
FIG. 2 is a microscopic photograph showing spores of *Bacillus subtilis* purified according to renografin gradients method.
Figure 3:
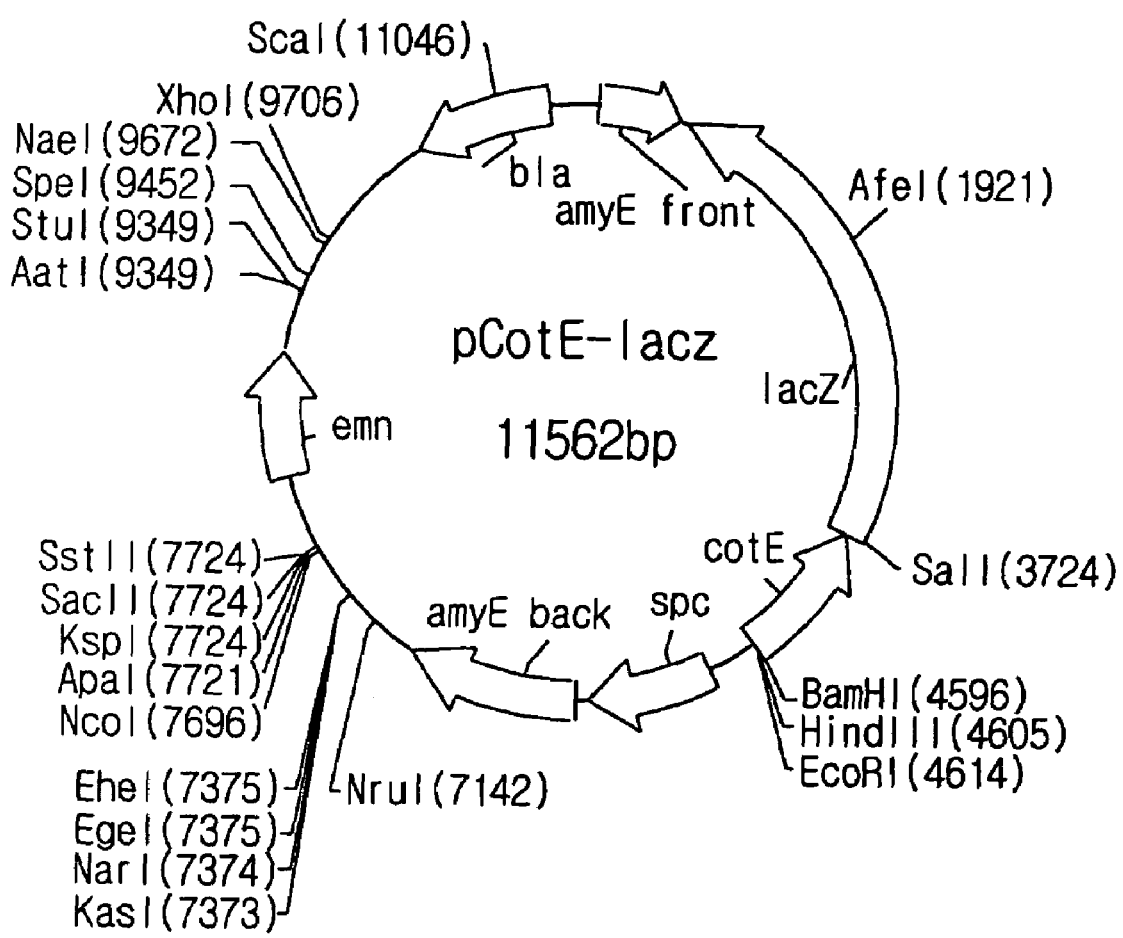
FIG. 3 is a genetic map of the recombinant vector pCotE-lacZ of the present invention.
Figure 4:
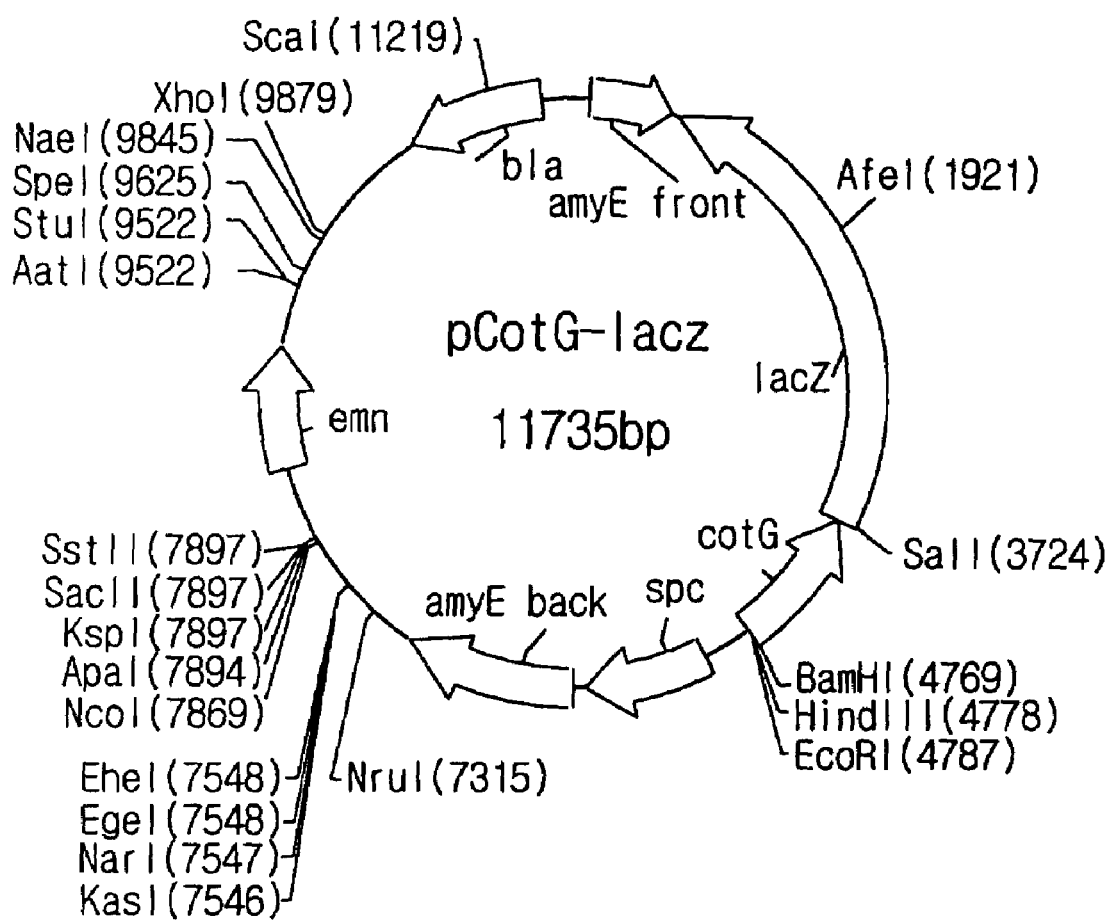
FIG. 4 is a genetic map of the recombinant vector pCotG-lacz of the present invention.

After then, each amplified PCR products were digested with BamHI and SalI and cloned between BamHI and SalI sites of plasmid pDG1728 which is a gratuitous gift by Dr. P. Stragier (Geurout-Fleury, A. M., et al., *Gene,* 180: 57-61 (1996)), thus the constructed vectors express the fusion protein of coat protein and β-galactosidase. FIG. 3a shows the genetic map of pCotE-lacZ expressing fusion protein of CotE protein and β-galactosidase and FIG. 3b shows the genetic map of pCotG-lacZ expressing Fusion protein of CotG protein and β-galactosidase.

SEQ ID NO:23 shows the sequence of cotE-lacZ fused genes and SEQ ID NO:24 shows the amino acid sequence of CotE-LacZ fusion protein. In SEQ ID NO:23, promoter for cotE is 1-329, CotE structural gene is 330-872, restriction site is 873-878 and LacZ structural gene is 879-3902.

SEQ ID NO:25 shows the sequence of cotG-lacZ fused genes and SEQ ID NO:26 shows the amino acid sequence of CotG-LacZ fusion protein. In SEQ ID NO:25, promoter of cotG is 1-460, CotE structural gene is 461-1045, restriction site is 1046-1051 and LacZ structural gene is 1052-4075.

I-2: Pure Isolation of Spores

Constructed recombinant expression vectors were transformed into *Bacillus subtilis* DB104 (Kawamura F. and Doi R. H., J. Bacteriol. 160: 442-444(1984)) using natural transformation (C. R. Harwood, et al., Molecular Biological Methods for *Bacillus*, John Wiley & Sons, New York, p. 416 (1990)).

Other methods such as conjugation or trnasduction can be applied for introduction of the recombinant vectors into *Bacillus* strain.

Subsequently, each *Bacillus* strain comprising the fused gene between coat protein and β-galactosidase was cultured for 24 hr at a shaking incubator (37° C., 250 rpm) in GYS medium (($NH_4$)$_2SO_4$ 2 g/l, Yeast extract 2 g/l, $K_2HPO_4$ 0.5 g/l, glucose 1 g/l, $MgSO_4 \cdot 5H_2O$ 0.07 g/l), and the only pure spores were isolated using renografin gradients method (C. R. Harwood, et al., "Molecular Biological Methods for *Bacillus*." John Wiley & Sons, New York, p. 416(1990)).

I-3: Display of Proteins on Spore Surface

Figure 5:
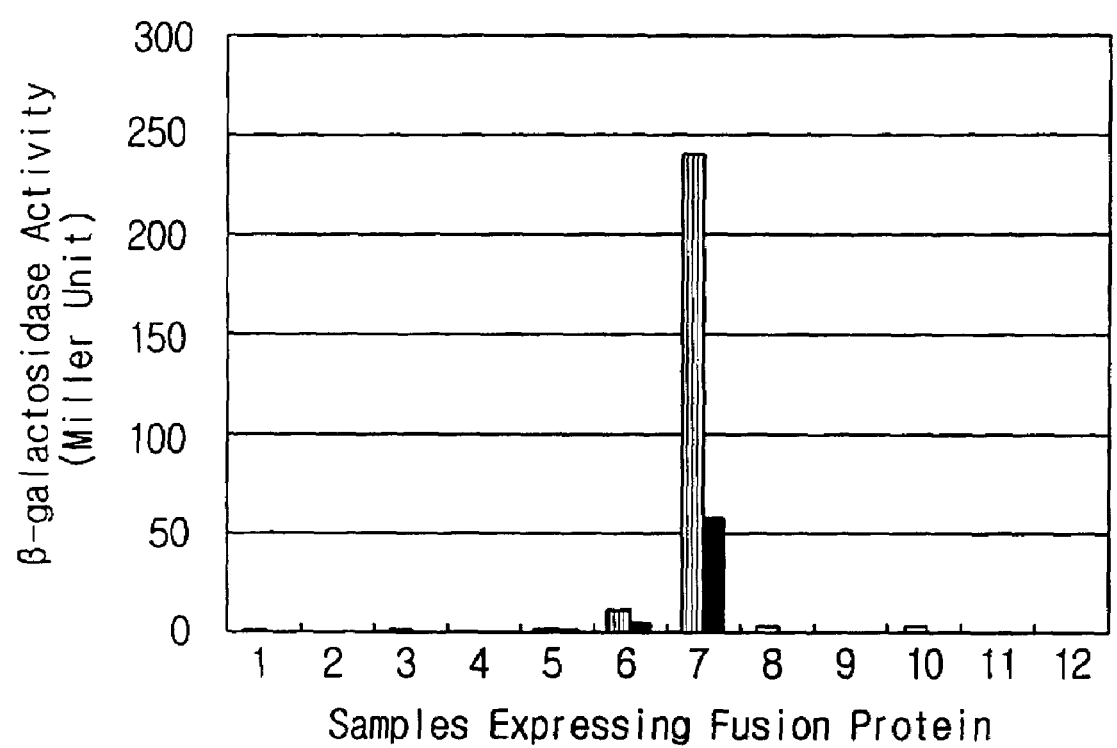
FIG. 5 represents screening results demonstrating the preferred surface display motif in the present invention.

The spores isolated in the above-described Example and the cell pellet of *Bacillus subtilis* DB104 were subjected to evaluation of the activity of β-galactosidase using Miller's method (Miller, "Experiments in Molecular Genetics", Cold Spring Harbor, N.Y.: Cold Spring Harbor Laboratory, p. 352-355(1972)) and the results are shown in FIG. 5. In FIG. 5, the gray bar indicates cell pellet, the black bar indicates the activity of β-galactosidase in purely isolated spores and '1' relates to result of control *Bacillus subtilis* DB104; '2' to result of SpoIVA-LacZ; '3' to result of CotB-LacZ; '4' to result of CotC-LacZ; '5' to result of CotD-LacZ; '6' to result of CotE-LacZ; '7' to result of CotG-LacZ; '8' to result of CotH-LacZ; '9' to result of CotM-LacZ; '10' to result of CotV-LacZ; '11' to result of CotX-LacZ; and '12' to result of CotY-LacZ fusion protein, respectively.

As shown in FIG. 5, it is known that Deits TL (U.S. Pat. No. 5,766,914) fails to induce the sufficient surface display of cotC and cotD since the expression levels of cotC and cotD are as low as the control. However, the expression level of cotE and cotG are comparatively high and especially, expression level of cotG is remarkably high comparing to other coat proteins. In addition, in the isolated spores, the surface display using cotG shows the highest enzyme activity, which demonstrates that CotG-LacZ fusion proteins are the highest level of display on spore surface.

Considering the expression level and the amount of fusion proteins displayed on spore surface, it is known that the cotG is the most preferable surface display motif. It is known to one skilled in the art that these results exclude other coat proteins other than cotG from applying to spore surface display.

I-4: Effect of Proteases on the Surface-Displayed Enzymes

Figure 6:
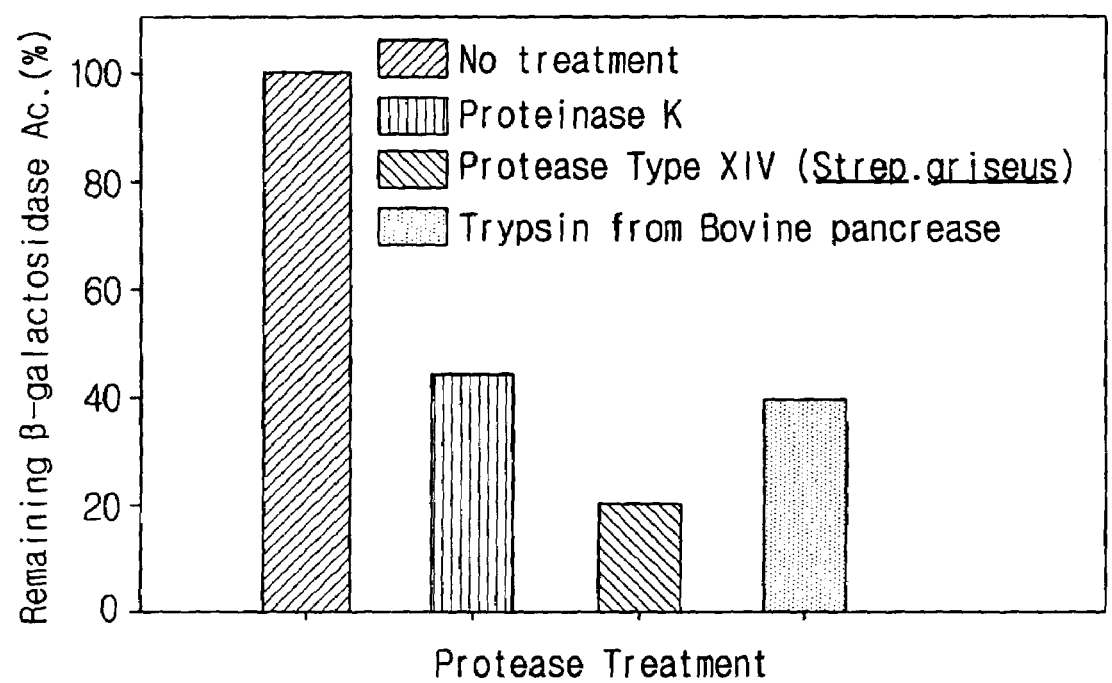
FIG. 6 is a graph showing the affect of protease to β-galactosidase displayed on spore surface.

To confirm whether the surface-displayed β-galactosidase is degraded or not, the purely isolated spore displaying CotG-LacZ was resuspended into 100 μl of PBS solution, and each 10 mg/ml of protease K, protease type XIV or trypsin was treated. Thereafter, the activity of β-galactosidase was measured as described above and the results are shown in FIG. 6. As shown in FIG. 6, the activity of spore surface-displayed β-galactosidase is decreased with some variations in each result. These results give the evidence for the localization of β-galactosidase on spore surface.

Figure 7:
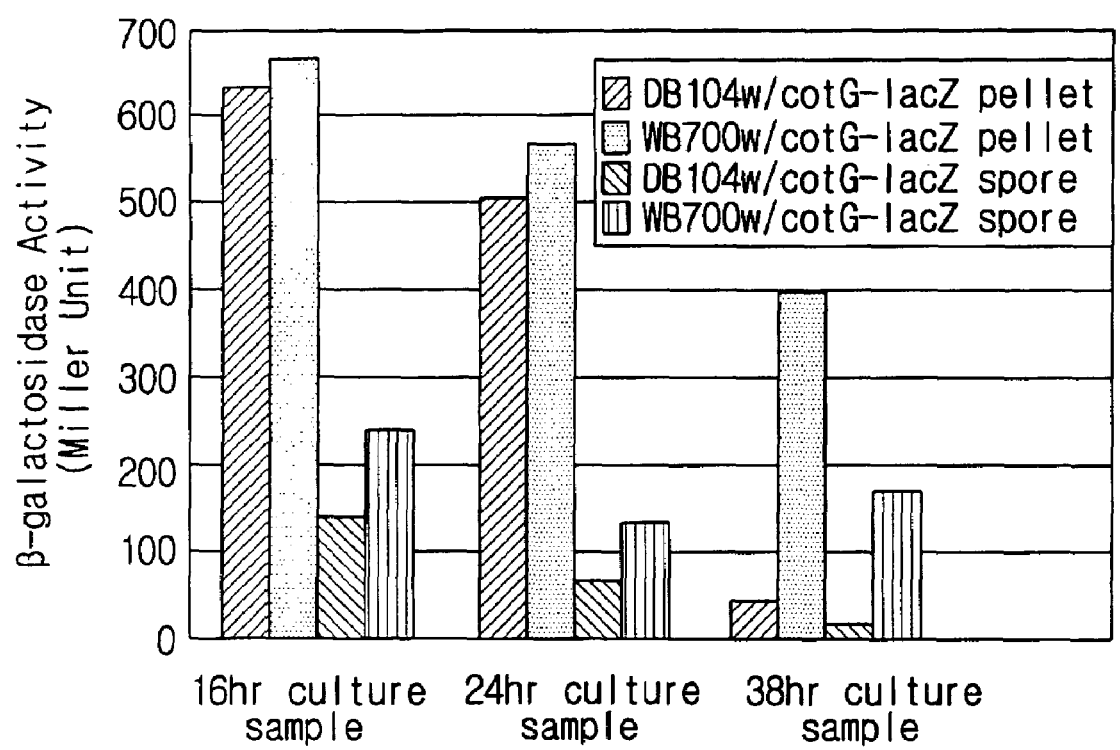
FIG. 7 is a graph showing the activity of β-galactosidase displayed on spore surface in accordance with culture time.

DB104 strain lacking neutral and alkaline protease and WB700 strain (Ye, R., et al., *Biotechnology and Bioengineering*, 62:87-96(1999)) lacking 7 proteases among proteases secreted from *Bacillus subtilis* were transformed with the pCotG-lacZ expression vector using natural transformation method as described in example I-1, and the activity of β-galactosidase in cell pellet and spores was measured as described in example I-3 (FIG. 7). As shown in FIG. 7, while the enzyme activity is abruptly decreased in DB104 strain as time goes, WB700 strain shows slight decrease in enzyme activity. These results indicate that the displayed β-galactosidases on spore surface are degraded in DB104 strain by the proteases secreted extracellularly; however, the displayed β-galactosidases in WB700 are stably maintained because of lack of the proteases secreted extracellularly. Therefore, the results also support the localization of β-galactosidase on spore surface.

Example II

Spore Production Depending on Culture Time

As shown in FIG. 7, it is required to stop incubation on a specific time point and isolate spores. In DB104, the enzyme activity of spores after 38 hr of incubation is significantly low comparing to that after 24 hr of incubation. Thus, it is demonstrated that the adjustment of incubation time makes it possible to yield spores displaying enzyme on its surface with the greatest enzyme activity.

Example III

Characterization of Spores Dispalying β-Galactosidase

Figure 8:
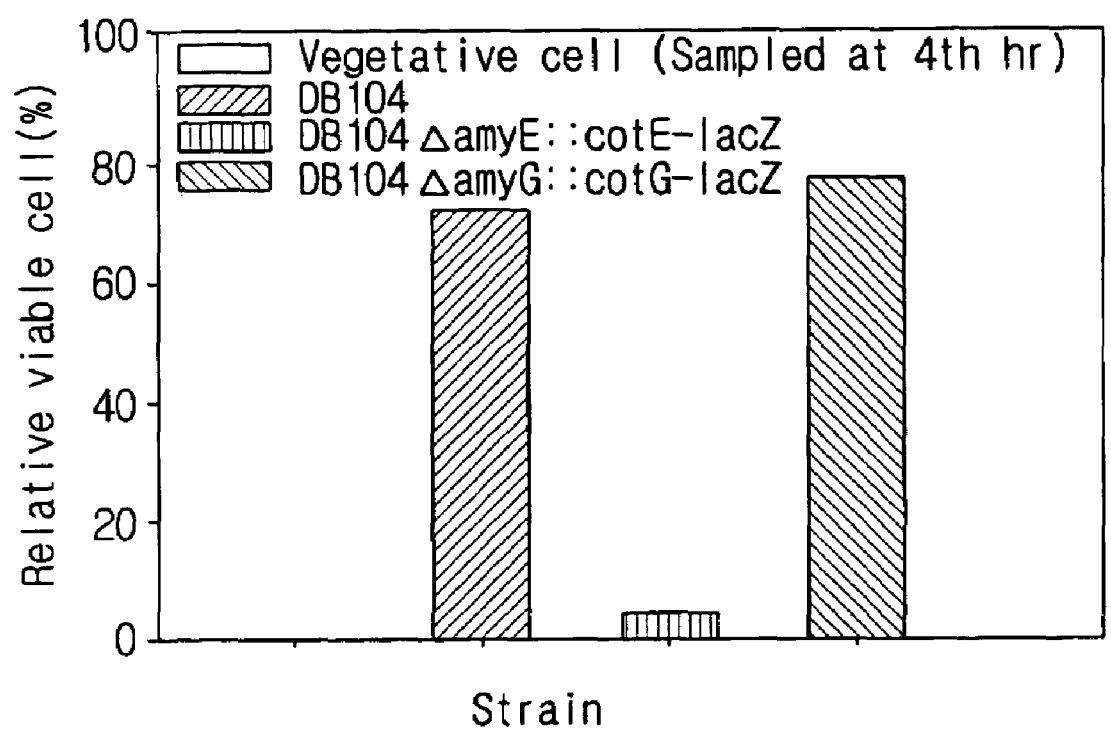
FIG. 8 is a graph representing the heat stability of *Bacillus subtilis* DB104 strain displaying on its surface the protein.

Heat resistance was measured as follow in spores displaying β-galactosidase: 100 μl of spores isolated by renografin gradients in Example I-2 were heated for 15 min and then spread on LB plates to evaluate viability of spores (FIG. 8). As shown in FIG. 8, spores displaying CotG-LacZ show similar heat resistance to spores without surface protein. In a result, the display of the foreign protein fused to coat protein on spore surface does not affect on its inherent characteristics such as heat resistance. Moreover, these results provide the promising usage of spore displaying on its surface enzyme in chemical reactions at high temperature. In addition, from these results, it is suggested that the spores transformed according to the present invention remain their inherent resistances to lysozyme, a bacterial cell wall-degrading enzyme and solvent.

Example IV

Displaying Various Enzymes on Spore Surface

IV-1: Construction of Recombinant Vectors

To use spores displaying various enzymes, it is prerequisite to confirm whether various enzymes in addition to β-galactosidase can be surface-displayed. Firstly, plasmid pHPS9 (Haima, et al., *Gene*, 86:63-69(1990)) was digested by EcoRI and HindIII and manipulated into blunt ends using Klenow enzyme. Then, DNA fragment containing multiple cloning sites, which was obtained from plasmid p123T (EMBL Z46733) with BssHII, was ligated to the blunt-ended pHPS9 plasmid to use as virgin vector named pCSK1 in the following experiments. The pCSK-cotG plasmid was prepared by restricting PCSK1 plasmid with BamHI and PstI and ligating PCR-amplified cotG gene. In the course of PCR for cotG gene amplification, a linker between cotG gene and target gene was incorporated using cotG-linker 5 primer (SEQ ID NO:27) and 3 primer (SEQ ID NO:12) with template of DNA in *Bacillus subtilis*.

In other experiments, genes encoding carboxymethyl cellulase, levansucrase and lipase was prepared as follows: Carboxymethyl cellulase cloned in pBSI plasmid (S. H. Park et al., *Agric. Biol. Chem.*, 55: 441-448(1991)) was directly employed. The pBS1 plasmid contains the gene encoding carboxymethylcelluase cloned from *Bacillus subtilis* BSE616 strain. In the present Example, PCR was performed with the pBS1 as template using primer represented by SEQ ID NOs:28 and 29. In the case of PCR for levansucrase, pSSTS110 plasmid (Jung, H.-C., et al., *Nat. Biotech.*, 16; 576-580(1998)) was used as template and primers represented by SEQ ID NOs:30 and 31 were used. In PCR for lipase, pTOTAL (Ahn, J.-H., et al., *J. Bacteriol.*, 181: 1847-1852(1999)) was added as template and primers of SEQ ID NOs: 32 and 33 were used. All PCRs were performed in the same condition as described in Example I-1.

Figure 9:
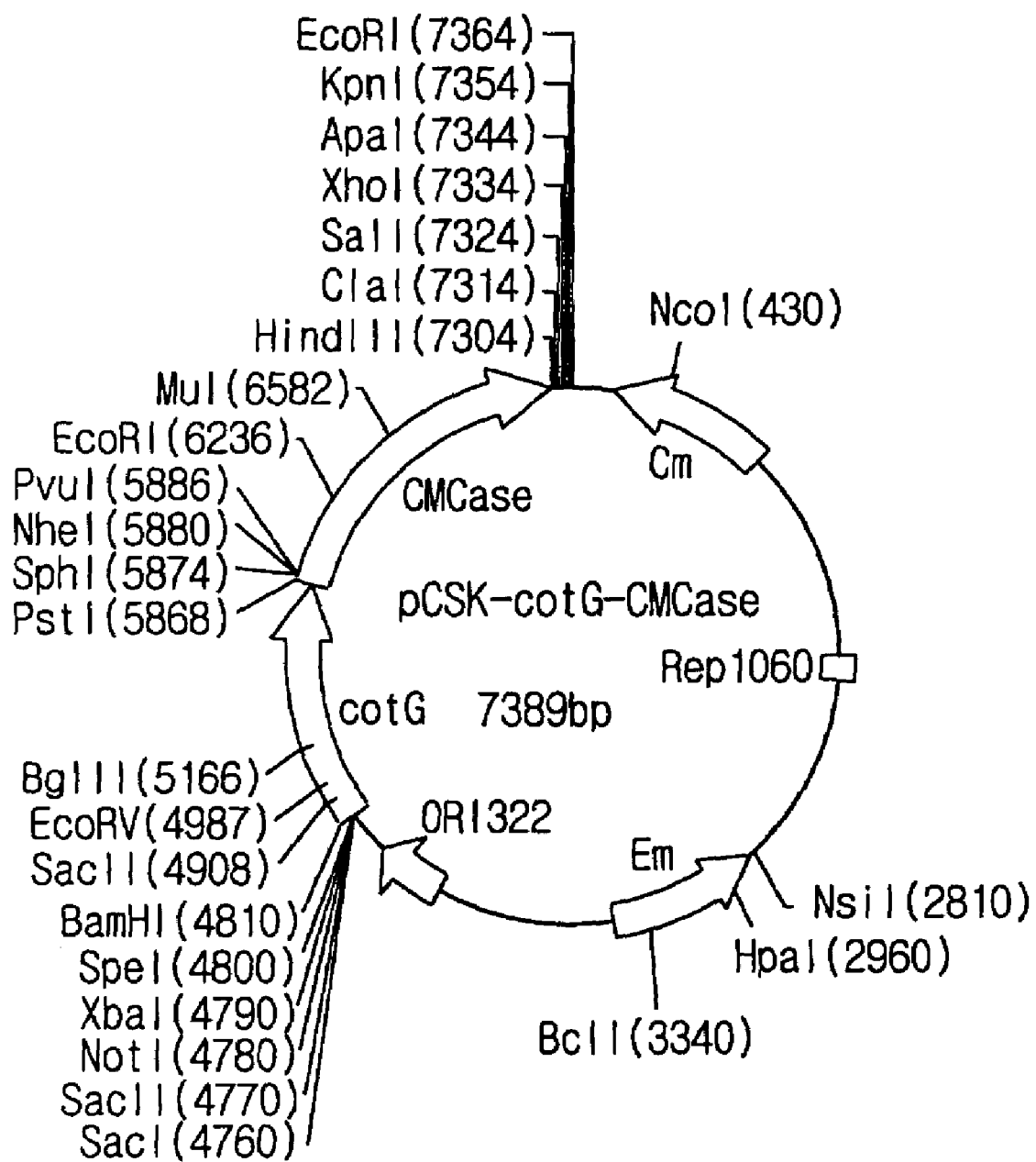
FIG. 9 is a genetic map of recombinant vector pCSK-cotG-CMCase of this invention.

Recombinant vectors containing gene coding for fusion between CotG and the carboxymethylcelluase, levansucrase or lipase were prepared by cloning into pCSK-cotG using PstI and BamHI restriction enzymes both in vector and in the PCR-amplified inserts. As an example of the above construction, FIG. 9 shows pCSK-cotG-CMCase which is the recombinant vector encoding fusion protein between CotG and carboxymethylcellulase. Transformed *Bacillus subtilis* DB104 with pCSK-cotG-CMCase was named *Bacillus subtilis* GFSD18 and deposited at the Korean Collection for Type Cultures (KCTC, KR) with accession No. KCTC 0887BP (Nov. 16, 2000).

SEQ ID NO:34 shows nucleotide sequence of fused cotG-CMCase genes and SEQ ID NO:35 shows amino acid sequence of CotG-CMCase encoded by SEQ ID NO:34. In SEQ ID NO:34, promoter for cotG is 1-460, structural gene for CotG is 461-1045, linker is 1046-1084, and structural gene for CMCase is 1085-2491.

IV-2: Expression of Recombinant Vectors and Verification

The above-prepared recombinant vectors were employed for transformation of *Bacillus subtilis* DB104 with the same procedures as described in Example I-2. Subsequently, each transformed *Bacillus* strains was cultured for 24 hr at a shaking incubator (37° C., 250 rpm) in GYS midium, the only pure spores were isolated using renografin gradients method, and enzyme activity of carboxymethylcellulase (Kim, et al., *Appl. Environ. Microbial.*, 66:788-793(2000)), levansucrase (Jung, et al., *Nat. Biotech.*, 16:576-580(1998)) or lipase was evaluated. The activity of lipase was evaluated as follow: The spores suspended in 10% PBS was mixed with 10% olive oil, reacted for 48 hr, treated with 0.2 ml cupric acid on supernatant solution and the observance of OD was performed at 715 nm.

Figure 10:
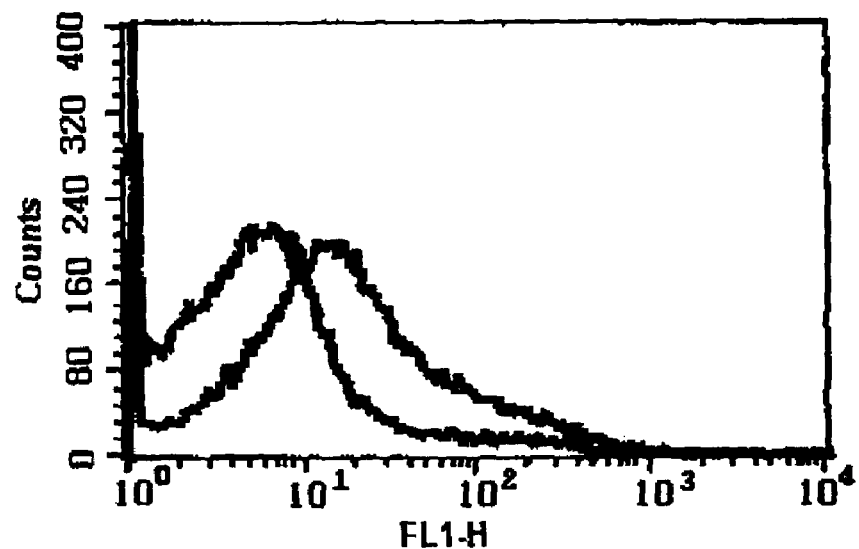
FIG. 10 is a graph showing analysis of spore surface-displayed carboxymethylcellulase using flow cytometry.

In the case of carboxymethylcellulase, the activity of enzyme displayed on spore was 175 mU comparing to 0 mU in control. In other verifying method, carboxymethylcellulase-specific andtibody (Kim, et al., *Appl. Environ. Microbiol.*, 66:788-793(2000)) was probed for flow cytometry (FACSORT (Cell Sorter Flow Cytometer, Becton Dickinson, USA) and the carboxymethylcellulases were detected on the surface of spores transformed by pCSK-cotG-CMCase (FIG. 10).

Figure 11:
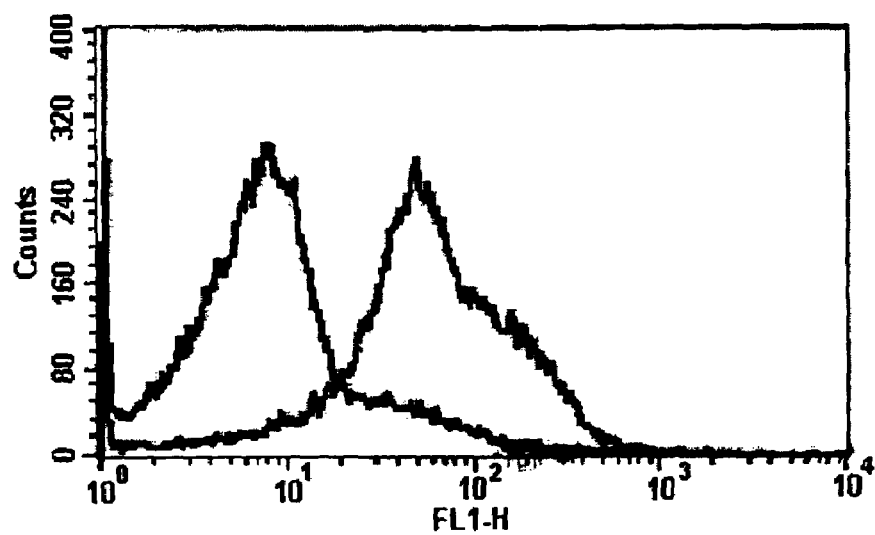
FIG. 11 is a graph showing analysis of spore surface-displayed levansucrase using flow cytometry.
Figure 12:
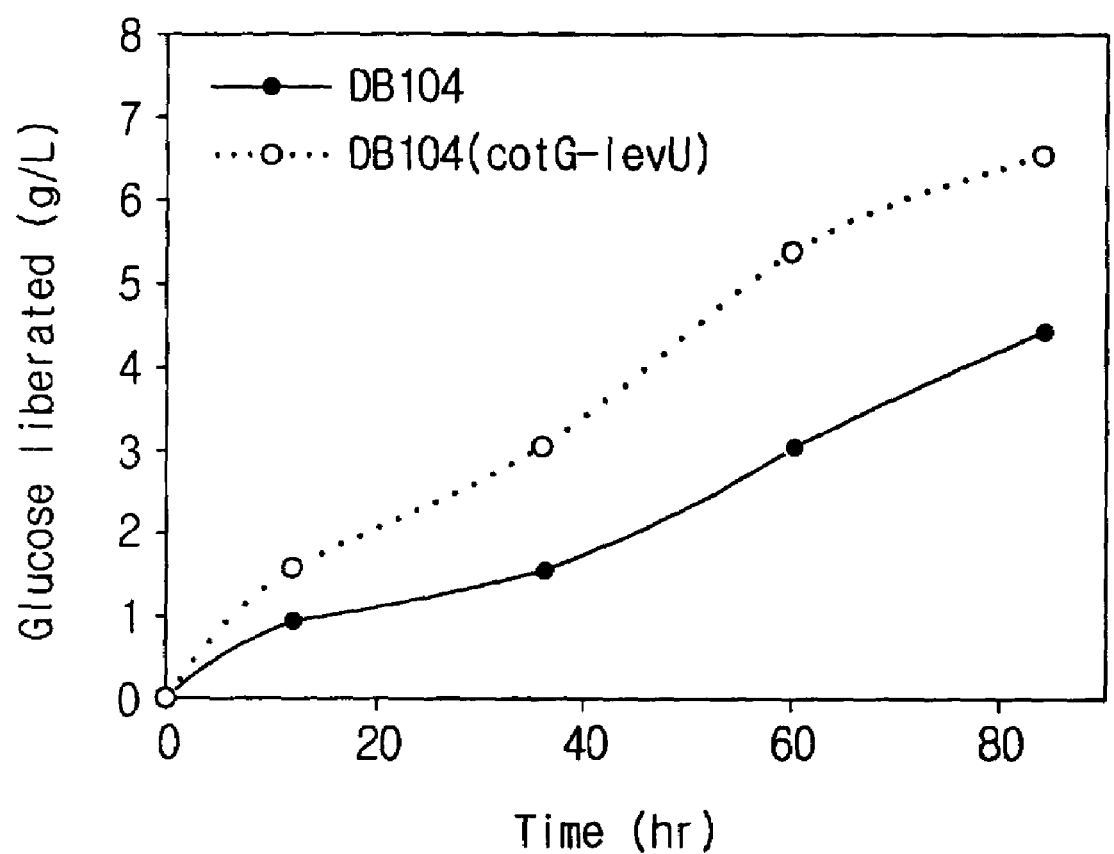
FIG. 12 is a graph showing the activity of spore surface-displayed levansucrase.

The activity of levansucrase was also high in spores transformed by recombinant vector (FIG. 12) and the levansucrases were detected on the surface of transformed spores as verified with flow cytometery using levan sucrase-specific antibody (Jung, et al., *Nat. Biotech.*, 16:576-580(1998)) in the same procedures as above-described % in carboxymethylcellulase (FIG. 11).

The activity of lipase was measured as $A_{715}$=0.14 in spores transformed with recombinant vector.

On the basis of these results, it is demonstrated that various enzymes as well as β-galactosidase can be displayed on the surface of spore according to the present invention.

Based on the results in these examples and example I, it is known to one skilled in the art that the gene construct containing gene encoding fusion protein between coat protein and protein of interest may exist as plasmid in host cell independently or as integrated form into chromosome of host cell and both forms may lead to successful spore surface display. It is also recognizable that the gene of coat protein may be followed or preceded by the gene of the protein of interest. In addition, it is recognized that in the gene construct, the overall sequence, fragments, two or more repeated sequences of the gene of coat protein are useful. In two or more repeated sequences, the repeated sequences may be the same or different each other. The overall sequence, two or more repeated sequences of the gene of the protein of interest are also useful in the fusion sequence. In two or more repeated sequences, the repeated sequences may be the same or different each other.

It is recognized by one skilled in the art that the expression of the fusion protein between coat protein and protein of interest can be induced by virtue of promoters of coat protein gene and other suitable promoters operable in host cell. Any vector carrying the present gene construct may be used in this invention, which is recognized by one skilled in the art referring to these results.

It is known that both monomric and multimeric enzyme can be applied for the present invention since the β-galactosidase used in example I is tetramer (U. Karlsson et al., *J. Ultrastruct. Res.*, 10:457-469(1964)) and the enzymes described in this Example are monomers.

Example V

Display of Antibody on Spore Surface and Screening for Directed Evolution

On the purpose of application of other proteins in addition to enzymes, the experiment to display antibody on spore surface was performed as follows:

V-1: Construction of Recombinant Vector for Surface Display of Single Chain Fv

Gene encoding single chain Fv, against Pre-S2 domain (SEQ ID NO:36) of hepatitis B virus (HBV) was linked to cotG gene encoding surface protein of *Bacillus subtilis* spore. Single chain Fv gene was amplified by PCR with pAScFv101 (WO 9737025) as template and with primers described in SEQ ID NOs:37 and 38. Taq polymerase purchased from Bioneer (Korea) was used for total 30 cycles of PCR under condition of denaturation for 30 sec at 94° C., annealing for 30 sec at 55° C. and extension for 1 min at 72° C. And then, each PCR product was restricted by ApaI and NheI, cloned into pCSK-CotG between the same restriction sites (pCSK-CotG-scFv) and transformed into JM109 using transformation method by Inoue, et al. (Inoue, H., et al., *Gene*, 96:23-28(1990)). The amplified vectors for displaying on spore surface were isolated by alkaline extraction method (Sambrook et al., *Molecular Cloning: A laboratory Manual*, Cold Spring Harbor, N.Y., 1989) and transformed into *Bacillus subtilis* DB104 by natural transformation as described in Example I-1.

V-2: Verification of Single Chain Fv Display on Spore Surface Using Flow Cytometry Affinity of the displayed single chain Fv against the Pre-S2 of HBV was evaluated by FACSORT (Cell Sorter Flow Cytometer, Becton Dickinson, U.S.A.) as the following procedures.

Firstly, Pre-S2 peptide was labeled with fluorescein (PanVera, USA) using fluorescein succinidimyl ester coupling method.

Figure 13:
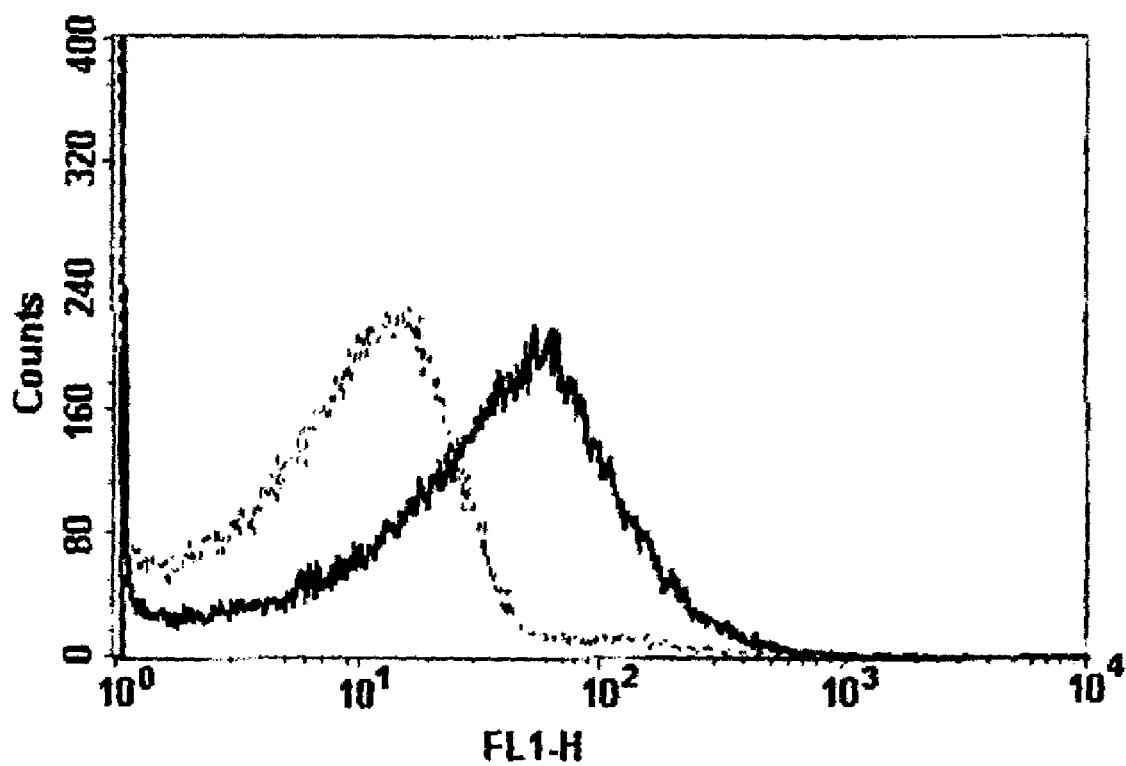
FIG. 13 is a graph representing analysis of spore surface-displayed monoclonal antibody using flow cytometry.

The transformed strains were inoculated into LB broth containing 5 μg/ml chloroamphenicol, pre-cultured for 8-10 hr at 37° C., 1% of seed culture was inoculated into GYS broth for sporulation, cultured for 24 hr at 37° C. and the cultured media was harvested. The pure spores were isolated using renografin gradients method, 100 μl pure spores were blocked with PBS containing 3% skim milk to inhibit non-specific binding and reacted with 10 μl of fluorescein labeled Pre-S2 peptide. Thereafter, the spores bound to fluorescein labeled Pre-S2 peptide were detected in the same procedures as described in example IV (FIG. 13). As shown in FIG. 13, it is demonstrated that the monoclonal antibody against Pre-S2 peptide is successfully displayed without reduction of the affinity to its antigen.

According to the above results, it is recognized that the present methods may be applicable to any protein, for example, enzyme, hormone, hormone analogue, enzyme inhibitor, signal transduction protein or its fragment, antibody or its fragment, antigen protein, attachment protein, structural protein, regulatory protein, toxin protein, plant defense-inducing protein.

V-3: Selection of Spores Displaying Single Chain Fv using Flow Cytometry

Whether the displayed single chain Fv has affinity to Pre-S2 of HBV was verified with FACSORT (Cell Sorter Flow Cytometer, Becton Dickinson, U.S.A.)as follows:

The transformed strains were inoculated into LB broth containing 5 μg/ml chloroamphenicol, pre-cultured for 8-10 hr at 37° C., 1% of seed culture was inoculated into GYS broth for sporulation, cultured for 24 hr at 37° C. and the cultured media was harvested. And then, 50 ml of harvested culture medium was centrifuged at 10,000 g for 10 min supernatant was discarded, bacteria were resuspended in 500 μl of 20% renografin (Sigma, USA). 100 μl of resuspended cell was carefully flowed onto 500 μl of 50% renogrant in microtube to form layer, the microtube was centrifuged at 10.000 g for 30 min and pure spores were isolated from pellet.

To discard remained renografin, spores were rinsed 3 times with DW and resuspended in PBS buffer. And then, spores displaying single chain Fv were mixed with wild type spores at a ratio of 1:103 and 1:105 and the spores with affinity to Pre-S2 of HBV were harvested using fluorescein-labeled Pre-S2 peptide and FACSORT (Cell Sorter Flow Cytometer, Becton Dickinson, U.S.A.).

The selectivity was evaluated by colony-forming assay on LB agar plates and LB agar plates containing 5 μl/ml of chloroamphenicol comparing to wild type. Spores displaying surface single chain Fv are resistant to chloroamphenicol owing to chloroamphenicol resistant gene contained in the recombinant vectors.

Figure 14:
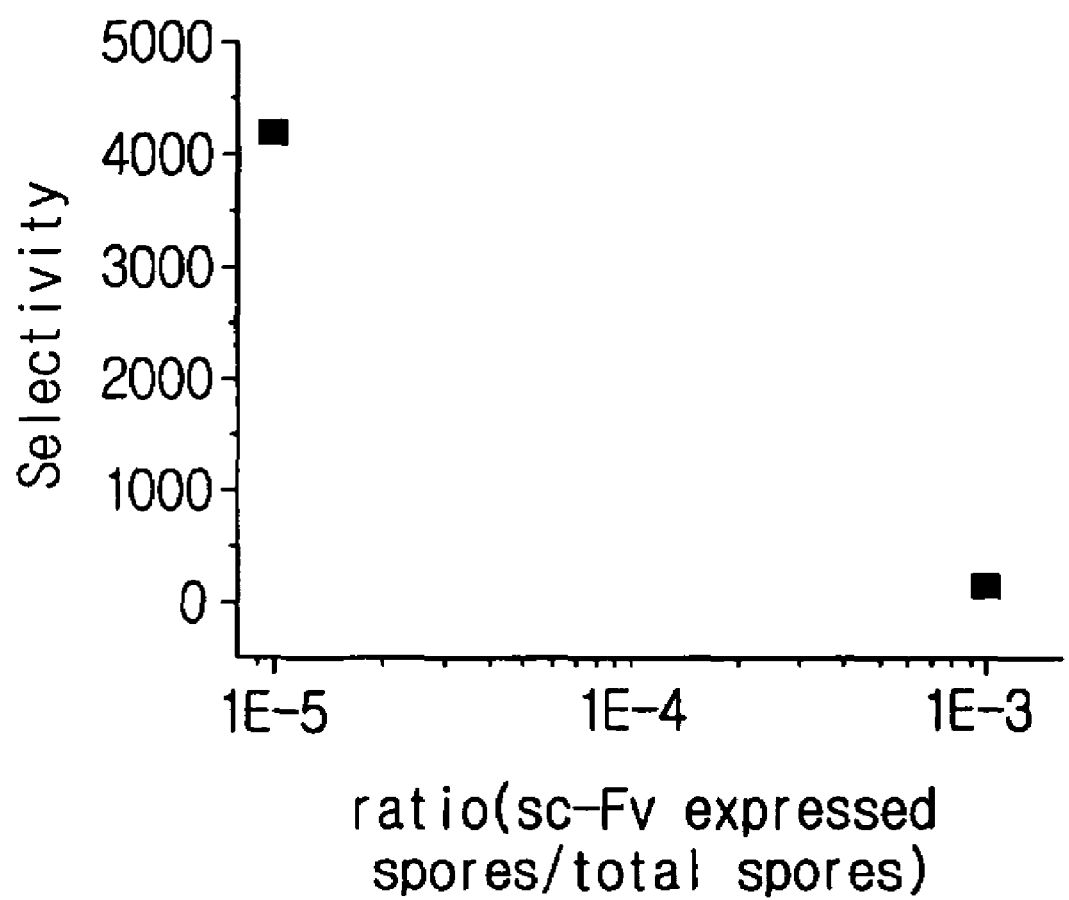
FIG. 14 is a graph demonstrating selectivity to spore displaying single chain Fv.

FIG. 14 shows the selectivity of spores displaying single chain Fv in each ratio (selectivity=ratio of spores displaying single chain Fv after flow cytometry/ratio of spores displaying single chain Fv before flow cytometry). In the case that the ratio of spores displaying single chain Fv before flow cytometry is $10^{-5}$, the selectivity was over 4,000, which indicates that spores with enhanced affinity can be selected by flow cytometry among spores displaying various antibody libraries.

V-4: Directed Evolution of Single Chain Fv Displayed on Spore Surface

To display single chain Fv library on spore surface, the gene encoding single chain Fv against Pre-S2 of HBV was amplified by error prone PCR. PCR was carried out using pAScFv101 plasmid described in the example V-1 as template and SEQ ID NOs:37 and 38 as primer. PCR mixture was prepared by mixing 0.3 μM of each primers, 5 ng of DNA template, PCR solution (10 mM Tris(pH 8.3), 50 mM KCl, 7 mM $MgCl_2$, 0.01% (w/v) gelatin), 0.2 mM dGTP, 0.2 mM dATP, 1 mM dTTP, 1 mM dCTP, 5 U Taq polymerase from Bioneer (Korea) and DW up to 100 μl. Total 13 cycles of PCR was performed under condition of denaturation for 30 sec at 94° C., annealing for 30 sec at 50° C. and extension for 1 min at 72° C.

Subsequently, restricted PCR products with ApaI and NheI were cloned into pCSK-CotG, vector for displaying on spore surface, between the same restriction sites and library was prepared by transforming the cloned vectors into JM109 *E. coli* with the method of Inoue et al.

The vectors for displaying on spore surface were isolated by alkaline extraction method and transformed into *Bacillus subtilis* DB104 by natural transformation. And then, single chain Fv library against Pre-S2 of HBV was displayed on spore surface as described in example V-2 (FIG. 15).

Figure 15:
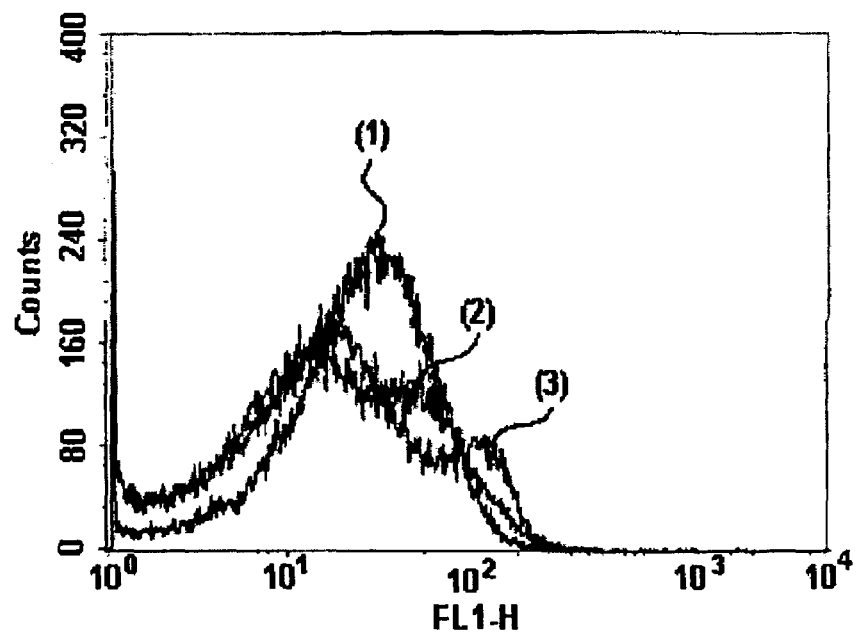
FIG. 15 is a graph representing analysis with flow cytometry of monoclonal antibody library to have binding affinity to Pre-S region of hepatitis B virus.

As shown in FIG. 15, spores with increased fluorescence (i.e., increased affinity) were isolated. This result demonstrates the applicability of the present invention to prepare and select protein variants with improved characteristics.

Example VI

Bioconversion Using Spores Displaying Protein of Interest

Forte of transglycosylation by enzyme is the capability of formation of site-specific glycosidic linkage without protection/de-protection step. There have been studied for formation of glycosidic linkage by 1) induction of reverse hydrolysis in non-aqueous system using glycosidase which is conventionally available glycosidic hydrolyzing enzyme and 2) transglycosylation in which glycosidic linkage is substituted with receptor alcohol instead of hydrolysis of glycosidic linkage by water (G. Ljunger et al., *Enzyme Microb. Technol.*, 16:1808-1814(1994); T. Usui et al., *Carbohytdr. Res.*, 244: 315-323(1993); and R. Lopez et al., *J. Org. Chem.*, 59:737-745(1994)). The above conventional methods usually use organic solvent to increase synthetic yield and inhibit hydrolysis. However, because the organic solvent inactivates enzyme, it is difficult to accomplish the high yield. Thus, it is necessary to inhibit the inactivation of glycosidase in organic solvent for higher glycosylation yield.

The purpose of the Example is to exemplify the higher glycosylation yield with improved enzyme stability even in organic solvent by virtue of displaying glycosidase on the surface of hydrophobic *Bacillus* spores.

VI-1: Stability of β-Galactosidase Displayed on Surface of Spores in Organic Solvent Each of β-galactosidase in free form (Sigma, USA) and the β-galactosidase displayed on surface of *Bacillus* spore was dispersed into 500 μl of Tris-HCl buffer (pH 7.5), added the same volume of the various solvents described in Table 1, mixed for 37° C. for 1 hr and the remained enzymatic activity was measured by Miller method described in Example I-3 (Table 1).

TABLE 1

|  | Residual activity (%) | |
| --- | --- | --- |
|  | Free form β-galactosidase | Surface-Displayed β-galactosidase |
| Control | 100 | 100 |
| Hexane | 84.3 | 100 |
| Ether | 48.2 | 77.2 |
| Toluene | 4.2 | 51.9 |
| Ethylacetate | 0.1 | 9.6 |
| Acetonitril | 0.0 | 0.8 |
| Ethanol | 0.0 | 0.0 |

As shown in Table 1, the displayed β-galactosidase shows higher stability than that of free form β-galactosidase in various organic solvents.

VI-2: Transglycosylation Reaction in Water-Organic Solvent Two-phase System Using β-galactosidase Displayed on Spore Surface To perform transglycosylation in two-phase system, β-galactosidase, which is one of conventional glycosidase, is used as a model for glycosylation reaction (Scheme 1).

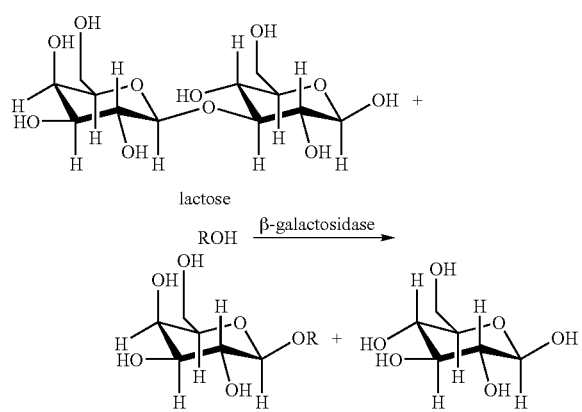

Scheme 1

At first, 1 ml of 1 M lactose in 10 mM phosphate buffer (pH 5.1) was mixed with 10 ml of 10 mM 5-phenyl-1-pentanol in hexane for reaction solution. And then, β-galactosidase displayed on spore surface (240 U; 1 U=the amount of enzyme capable of hydrolysis of 1 μmol ONPG (o-nitrophenyl-β-D-galactopyranoside) for 1 min at 37° C.) and free form β-galactosidase (240 U) was added into the above reaction solution, respectively, and reacted for 48 hr at 30° C. while stirring.

In results, the yield of 5-phenylpenthyl-β-D-galtopyranoside was 21% by β-galactosidase displayed on spore surface; however, in free form β-galactosidase, the hydrolysis of lactose only occurred with no transglycosylation. Such result is ascribed to the increased stability, in organic solvent, of β-galactosidase displayed on spore surface. Actually, after 72 hr reaction, about 5% of enzyme activity was detected in the displayed β-galactosidase while measured the complete inactivation in free form β-galactosidase. Another advantage of the displayed β-galactosidase owes to hydrophobicity of Bacillus spores. In other words, the distribution of displayed β-galactosidase at interface between water and organic solvent phase inhibits the hydrolysis comparing to free form β-galactosidase.

Based on the results of this Example, it is understood that variants and modifications thereof falling within the spirit of the invention may become apparent to those skilled in the art, for example, any enzymes in addition to β-galactosidase such as lipase and protease can be employed for bioconversion of the present invention. In addition, the present bioconversion is useful in single step or multi-step reaction and in aqueous or non-aqueous solution. The present bioconversion method can employ spore as free or immobilized form and can be performed with other microbes or enzymes.

Example VII

Display of Antigen on Spore Surface

By displaying antigen on spore surface, antigen capable of inducing immune response in vivo can be applied as live vaccine. Bacillus subtilis has been considered as safe strain to human body since it has been employed in food fermentation for a long time (Sonenshein A. L., et al., Bacillus subtilis and other gram-positive bacteria. American society for Microbiology, Washington, p871(1993)).

Gene for CotE-antigen fusion protein is constructed by cloning the gene for surface antigen of HBV into pCotG-lacZ vector constructed in Example I-1. Thereafter, the constructed recombinant vector is transformed into Bacillus subtilis and the transformants are cultured in GYS medium. And then, the antigen-displaying spores are purely isolated from culture medium by renografin gradients method.

Example VIII

Protein Improvement Using Spore Displaying Protein of Interest

For example of application of the present invention to high-throughput screening of target protein and to protein improvement, GFP (Green Fluorescence Protein) was used as follows:

VIII-1: Construction of Vector for GFP Display on Spore Surface gfp gene was cloned into pCSK-CotG vector constructed in Example IV-1 and the following sub-cloning procedures were performed for display on spore surface. Each primer was prepared for the purpose of fusing cotG gene to EGFP and GFPuv genes. The fluorescence intensity of EGFP (Excit./Emis. Maxima (nm): 488/509; Clontech, USA) has 35-fold stronger than that of wild type GFP and thus results in detection even in FITC filter and GFPuv (Excit./Emis. Maxima (nm): 395/509; Clontech, USA) is detectable with UV. For further manipulation, NheI and HindIII restriction sites were inserted into primers for egfp gene (SEQ ID NOs:39 and 40) and PstI and EcoRI restriction sites were inserted in primers for gfpvu gene (SEQ ID NOs:41 and 42).

Each of egfp (800 bp) and gfpuv (720 bp) genes was amplified by PCR (MJ Research PTC-100™ programmable Thermal Controller; 95° C. 30 sec, 55° C. 30 sec, 72° C. 2 min, 25 cycles) using Pfu Turbo polymerase (Stratagene, USA) and pEGFP-C1 (Clontedch, USA) or pGFPuv (Clontech, USA) as template.

Thereafter, pCSK-CotG-EGFP or pCSK-CotG-GFPuv vectors were constructed by cloning the restricted PCR products into NheI/HindIII (egfp gene) or PstI/EcoRI (gfpuv gene) restriction sites of pCSK-CotG vector.

VIII-2: Display and Confirmation of GFP on Spore Surface

The constructed vectors were transformed into *Bacillus subtilis* DB104 by natural transformation. Transformants were selected on LB agar plate containing 5 μg/ml chloroamphenicol. Through the selection, *Bacillus subtilis* DB104-SDG-EGFP strain for display of EGFP and *Bacillus subtilis* DB104-SDG-GFPuv strain for display of GFPvu on spore surface were obtained. As control strains, *Bacillus subtilis* DB104-SDC strain transformed with only pCSK vector and *Bacillus subtilis* DB104-SDG strain transformed for expressing only CotG protein were prepared.

For analysis of GFP display on spore surface, the above *Bacillus subtilis* DB104-SDC, -SDG, -SDG-EGFP and -SDG-GFPuv were inoculated into LB broth containing 5 μg/ml chloroamphenicol and spores were then purified as described in Example V-4.

Figure 16:
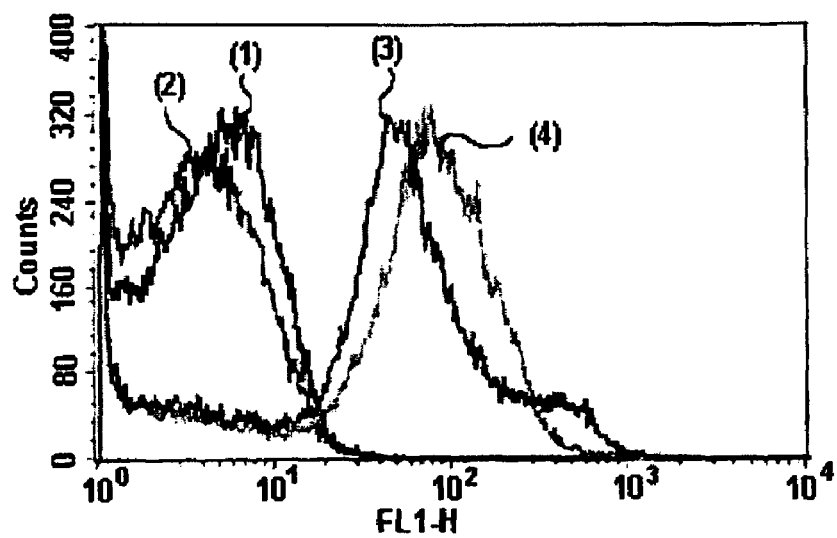
FIG. 16 is a graph showing analysis of spore surface-displayed GFP using flow cytometry.
Figure 17A:
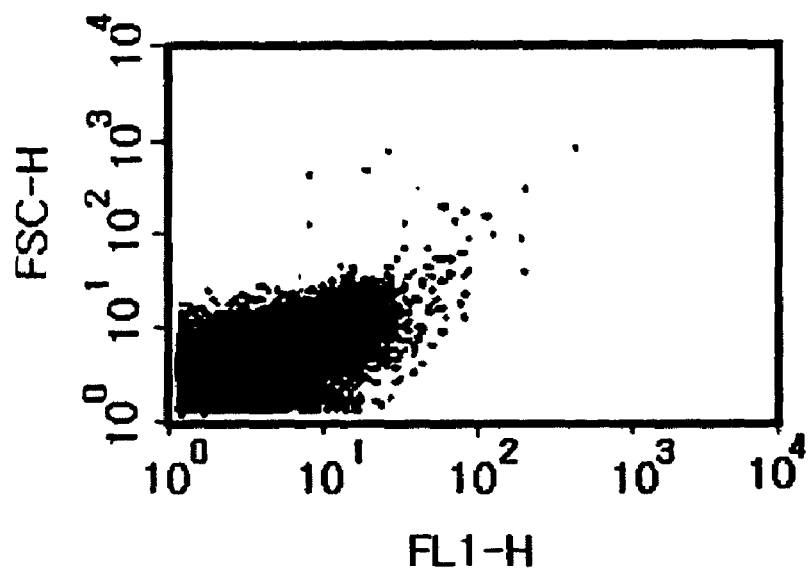
FIGS. 17a to 17d are graphs representing isolation with flow cytometry of spores displaying improved GFP.
Figure 17B:
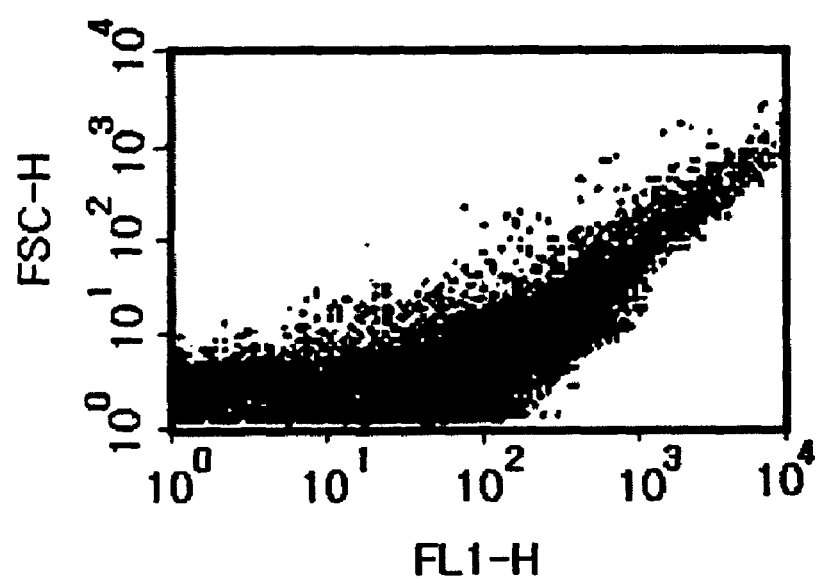
Figure 17C:
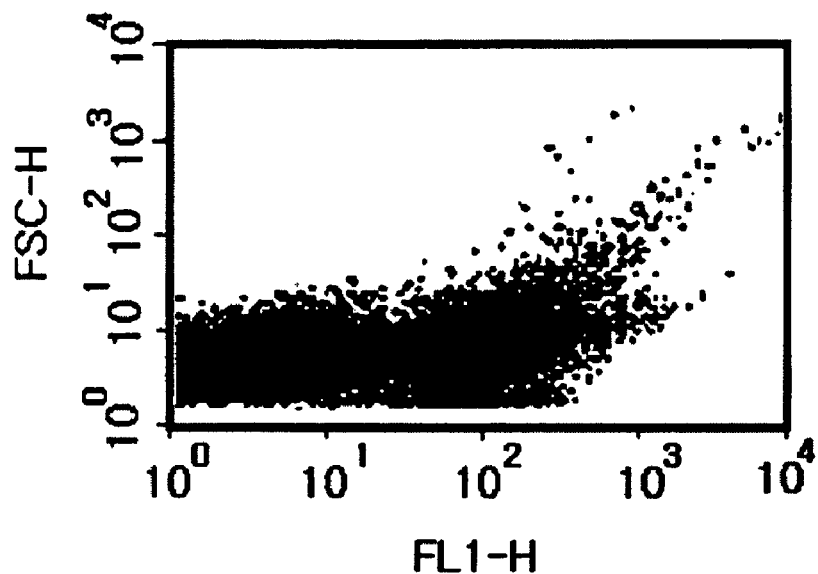
Figure 17D:
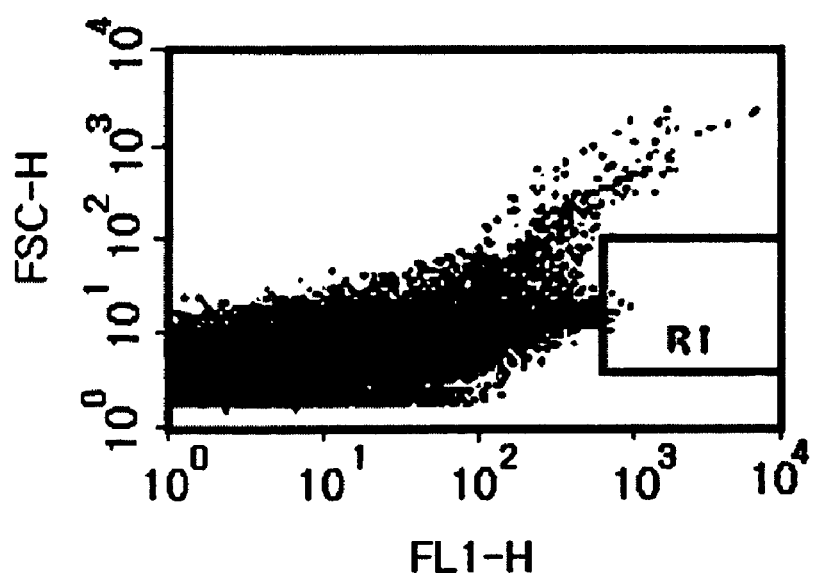

Subsequently, the display of GFP on spore surface was analyzed by measuring GFP fluorescence with flow cytometry in similar manner to Example IV (FIG. 16). In FIG. 16, curves (1)-(4) indicate the results of spores of DB104-SDC DB104-SDG, DB104-SDG-GFPuv and DB104-SDG-EFGP, respectively.

As shown in FIG. 16, the fluorescent intensity of spores derived from DB1047-SDG-EGFP (recombinant strain for EGFP-spore surface display) and DB104-SDG-GFPuv (recombinant strain for GFPuv-spore surface display) is significantly higher than that of DB104-SDC and DB104-SDG as control. In above results, the successful display of EGFP or GFPuv is validated by noticeable change of peaks indicating fluorescence in spore on its surface displaying EGFP or GFPuv comparing to controls.

VIII-3: Improvement of GFP

For the purpose of GFP improvement, error prone PCR was performed with template of pGFPuv vector (Clontech, USA) containing gfpuv gene using primers of SEQ ID NOs: 42 and 43. PCR mixture was prepared by mixing 0.3 μM of each primers, 5 ng of DNA template, PCR solution 10 mM Tris (pH 8.3), 50 mM KCl, 7 mM $MgCl_2$, 0.01% (w/v) gelatin), 0.2 mM dGTP, 0.2 mM dATP, 1 mM dTTP, 1 mM dCTP, 0.15 mM $MnCl_2$, 5 U Taq polymerase from Bioneer (Korea) and DW up to 100 μl. Total 13 cycles of PCR was performed under condition of denaturation for 30 sec at 94° C., annealing for 30 sec at 50° C. and extension for 1 min at 72° C.

Subsequently, the gfpuv genes were discarded from pCSK-CotG-GFPuv vectors by restriction with PstI/EcoRI, the above PCR-amplified inserts were cloned into the vectors with the same restriction sites and *Bacillus substilis* DB104 was transformed with the cloned vectors by natural transformation to construct gfpuv library displayed on spore surface. Then, the prepared library was inoculated into GYS medium for sporulation and pure spores were isolated as described in Example V-4. Transformant spores displaying improved GFP variant were screened by measuring GFP fluorescence with flow cytometry (FIGS. 17a to 17d). FIGS. 17a to 17d indicates the analysis of flow cytometry from *Bacillus subtilis* DB104-SDC, DB104-SDG-GFPuv, DB104-SDG-EGFP and DB104-SDG-GFP with gfp library subject to error prone PCR, respectively.

To isolate spores with higher fluorescent intensity than spores derived from DB104-SDG-EGFP and DB104-SDG-GFP control strains, the isolation of spores with higher fluorescence (region R1) among spores displaying GFP library was repeated several times.

It is understood that using the above method, the improved GFP protein exhibiting higher fluorescence intensity or fluorescence with different wavelength can be screened in a high-throughput manner.

Example VIII

Protein Array Using Spores Displaying on its Surface Protein of Interest $10^6$-$10^9$ spores displaying monoclonal antibodies against surface antigen of HBV are attached onto glass substrate for protein array (BMS, Germany) with aldehyde functional group on its surface using automated array apparatus. The attachment is made in a form of covalent linkage, which is Schiff base between amino group of protein on spore surface and aldehyde group on surface of slide glass. Although the displayed proteins attached on solid surface may be inactivated, they may have an orientation.

The protein array kit manufactured according to the present invention has a variety of applicable fields including diagnosis, analysis of gene expression, analysis of interaction between proteins, analysis of interaction between protein and ligand, study on metabolism, screening novel or improved enzymes, combinatorial biochemical synthesis and biosensor.

Example IX

Production of Antibody Using Spores Displayig Antigen

The spores on its surface displaying surface antigen of HBV isolated in Example VII are suspended in PBS and the same volume of complete Freund's adjuvant is added. Thereafter, the mixture is well agitated to make emulsion formulation and the emulsion is injected i.v. into BALB/c mice with age of 6-8 week. After 4 weeks of the injection, the secondary administration is performed. Then, the additional boosting injection is performed about 2-3 times for induction of antibody.

As described above, the display method on spore surface of the present invention provides improvements in: a resistance against physiochemical change in environment of display host, a diversity of displayable proteins, a viability of display host and rapidity of screening.

Throughout this application, various patents and publications are referenced and citations are provided in parentheses. The disclosure of these patents and publications in their entities are hereby incorporated by references into this application in order to more fully describe this invention and the state of the art to which this invention pertains.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Agterberg, M., Adriaanse, H. and Tommassen, J. Use of the outer membrane protein PhoE as a carrier for the transport of a foreign antigenic determinant to the cell surface of *Escherichia coli* K-12. *Gene* 59:145-150(1987)
2. Agterberg, M., Adriaanse, H., van Bruggen, A., Karperien, M. and Tommassen, J. Outer membrane PhoE protein of

*Escherichia coli* K-12 as an exposure vector:possibilities and limitations. *Gene* 88:37-45(1990)
3. Arnold, F. H. and Volkov, A. A. Directed evolution of biocatalysis. *Curr. Opin. Chem. Biol.* 3:54-59 (1999).
4. Charbit, A., Molla, A., Saurin, W. and Hofnung, M. Versatility of a vector for expressing foreign polypeptides at the surface of Gram-negative bacteria. *Gene* 70:181-189 (1988)
5. Charbit, A., Sobczak, E., Michel, M.-L., Molla, A., Tiollais, P. and Hofnung, M. Presentation of two epitopes of the preS2 region of hepatitis B virus on live recombinant bacteria. *J. Immunol* 139:1644-1658(1987)
6. Chiswell, D. J. and McCafferty, J. Phage antibodies:will new 'coliclonal' antibodies replace monoclonal antibodies, *TIBTECH* 10:80-84(1992)
7. Daugherty, P. S., Chen G., Olsen, M. J., Iverson, b. L., Georgiou, G. Antibody affinity maturation using bacterial surface display Protein Eng. 11:825-832 (1998)
8. d'Enfert, C., Ryter, A. and Pugsley, A. P. Cloning and expression in *Escherichia coli* of the *Klebsiella pneumoniae* genes for the production, cell surface localisation and secretion of the lipoprotein pullulanse. *EMBO J.* 6:3531-3538(1987)
9. Driks, A. *Bacillus subtilis* spore coat. Microbiol Mol Biol Rev 63(1):1-20 (1999)
10. Ferguson, M. A. J. and Williams, A. F. Cell-surface anchoring of proteins via glycosyl-phosphatidylinositol structures. *Ann. Rev. Biochem.* 57:285-320(1988)
11. Fischetti, V. A., Medaglini, D., Oggioni, M. and Pozzi, G. Expression of foreign proteins on Gram-positive commensal bacteria for mucosal vaccine delivery. *Curr. Opin. Biotechnol.* 4:603-610(1993)
12. Francisco, J. A., Earhart, C. F. and Georgiou, G. Transport and anchoring of b-lactamase to the external surface of *Eshcherichia coli*. *Proc. Natl. Acad. Sci. USA* 89:2713-2717(1992)
13. Freeman, A., Abramov, S., and Georgiou G. Site-protected fixation and immobilization of *Escherichia coli* cells displaying surface-anchored beta-lactamase. *Biotechnol Bioeng.* 62(2):155-159 (1999).
14. Fuchs, P., Breitling, F., Dubel, S., Seehaus, T. and Little, M. Targeting recombinant antibodies to the surface of *Escherichia coli*: fusion to a peptidoglycan associated lipoprotein. *Bio/Technology* 9:1369-1372(1991)
15. Georgiou, G. Analysis of large libraries of protein mutants using flow cytometry. *Adv Protein Chem.* 55:293-315 (2000).
16. Georgiou, G., Poetschke, H. L., Stathopoulos, C. and Francisco, J. A. Practical applications of engineering Gram-negative bacterial cell surfaces. *TIBTECH* 11:6-10 (1993)
17. Georgiou, G., Stathopoulos, C., Daugherty, P. S., Nayak, A. R., Iverson, B. L. and Curtiss III, R. Display of heterologous proteins on the surface of microorganisms: From the screening of combinatorial libraries to live recombinant vaccines. *Nature Biotechnology* 15:29-34(1997)
18. Georgiou, G., Stephens D., Stathopoulos, C., Poetschke H. L., Mendenhall J. and Earhart C. F. Display of b-lactamase on the *Escherichia coli* surface: outer membrane phenotypes conferred by Lpp'-OmpA'-b-lactamase fusions. Protein Eng. 9:239-247 (1996)
19. Hedegaard, L. and Klemm, P. Type 1 fimbriae of *Escherichia coli* as carriers of heterologous antigenic sequences. *Gene* 85:115-124(1989)
20. Jung, H. C., Lebeault, J. M. and Pan, J. G. Surface display of *Zymomonas mobilis* levansucrase by using the ice-nucleation protein of *Pseudomonas syringae*. *Nature Biotechnol.* 16:576-580 (1998a).
21. Jung, H. C., Park, J. H., Park, S. H., Lebeault, J. M. and Pan, J. G. Expression of carboxymethylcellulase on the surface of *Escherichia coli* using *Pseudomonas syringae* ice-nucleation protein. *Enzyme Microb. Technol.* 16:576-580 (1998b).
22. Kim, E. J. and Yoo, S. K. Cell surface display of CD8 ecto domain on *Escherichia coli* using ice-nucleation protein. *Biotechnol. Tech.* 12:197-201 (1998).
23. Kim, E. J. and Yoo, S. K. Cell surface display of hepatitis B virus surface antigen on *Escherichia coli* using *Pseudomonas syringae* ice-nucleation protein. *Lett. Appl. Microbiol.* 29:292-297 (1999).
24. Kim, Y. S., Jung, H. C. and Pan, J. G. Bacterial cell surface display of an enzyme library for selective screening of improved cellulase variants. *Appl. Environ. Microbiol.* 66:788-793 (2000).
25. Kwak, Y. D., Kim, E. J. and Yoo, S. K. Cell surface display of human immunodeficiency virus type I gp120 on *Escherichia coli* by using ice-nucleation protein. *Clinic. Diag. Lab. Immun.* 6:499-503 (1999).
26. Klauser, T., Kramer, J., Otzelberger, K., Pohlner, J. and Meyer, T. F. Characterization of the Neisseria Iga-core: The Essential unit for outer membrane targeting and extracellular protein secretion. *J. Mol. Biol.* 234:579-593(1993)
27. Klauser, T., Pohlner, J. and Meyer, T. F. Extracellular transport of cholera toxin B subunit using Neisseria IgA protease-domain: conformation-dependent outer membrane translocation. *EMBO J.* 9:1991-1999(1990)
28. Kornacker, M. G. and Pugsley, A. P. The normally periplasmic enzyme-lactamase is specifically and efficiently trnaslocated through the *Escherichia coli* outer membrane when it is fused to the cell-surface enzyme pullulase. *Mol. Microbiol.* 4(7):1101-1109(1990)
29. Lee, J. S., Shin, K. S., Pan, J. G. and Kim, C. J. *Nature Biotechnol.* 18:645-648 (2000)
30. Lewis P. J. and Errington J. Use of green fluorescent protein for detection of cell specific gene expression and subcellular protein localization during sporulation in *Bacillus subtilis* 142:733-740 (1996)
31. Little, M., Fuchs, P., Breitling, F. and Dubel, S. Bacterial surface presentation of proteins and peptides: an alternative to phage display technology, *TIBTECH* 11:3-5(1993)
32. Martineau, P., Charbit, A., Leclerc, C., Werts, C., O'Callaghan, D. and Hofnung, M. A genetic system to elicit and monitor antipeptide antibodies without peptide synthesis. *Bio/Technology* 9:170-172(1991)
33. Newton, S. M., Jacob, C. O. and Stocker, B. A. D. Immune response to cholera toxin epitope inserted in *Salmonella flagellin*. *Science* 244:70-72(1989)
34. Ochs, M., Angerer, A., Enz, S. and Braun, V. Surface signaling in transcriptional regulation of the ferric citrate transport system of *Escherichia coli*: mutational analysis of the alternative sigma factor FecI supports its essential role in fec transport gene transcription. *Mol. Gen. Genet.* 250:455-465(1996)
35. Palva, A. M. and Palva, I. A. Lactobacillus expression system using surface protein gene sequences, WO94/00581 (1994).
36. Richins, R. D., Kaneva, I., Mulchandani, A., and Chen, W. Biodegradation of organophosphorus pesticides by surface-displayed organophosphorus hydrolase. Nature Biotechnol. 15:984-987 (1997).
37. Samuelson, P., Hansson, M., Ahlborg, N., Androoni, C., Gotz, F., Bachi, T., Nguyen, T. N., Binz, H., Ulhen, M. and Stahl, S. Cell surface display of recombinant proteins on *Stapholococcus carnosus*. *J. Bacteriol.* 177(6):1470-1476 (1995).
38. Samuelson, P., Wernerus, H., Svedberg, M. and Stahl S. Staphylococcal surface display of metal-binding polyhistidyl peptides. *Appl. Envir. Microbiol.* 66: 1243-1248 (2000).
39. Schreuder, M. P., Mooren, A. T. A., Toschka, H. Y., Theo Verrips, C. and Klis, F. M. Immobilizing on the surface of yeast cells. *TIBTECH* 14:115-120 (1996).
40. Schulz, G. E. Bacterial porins: structure and function. *Curr. Opin. Cell Biol.* 5:701-707(1993)
41. Sleytr, U. B. and Sara, M. Bacterial and archaeal S-layer protein: structure-function relationships and their biotechnological applications. *TIBTECH* 15:1-9 (1997)
42. Stathopoulos, C., Georgiou G., and Earhart C. F. Characterization of *Escherichia coli* expressing an Lpp'OmpA (46-159)-PhoA fusion protein localized in the outer membrane. *Appl Microbiol Biotechnol.* 45(1-2):112-119 (1996).
43. Sousa, C., Cebolla, A., and de Lorenzo, V. Enhanced metalloadsorption of bacterial cells displaying poly-His peptides. *Nature Biotechnol.* 14:1017-1020 (1996).
44. Sousa, C., Kotrba, P., Ruml, T. Cebolla, A., and de Lorenzo, V. Metalloadsorption by *Escherichia coli* displaying yeast and mammalian metallothioneins anchored to the outer membrane protein Lams. *J. Bacteriol.* 180: 2280-2284 (1998).
45. Taylor, I. M., Harrison, J. L., Timmis, K. N. and O'Conor, C. D. The TraT lipoprotein as a vehicule for the transport of foreign antigenic determinants to the cell surface of *Escherichia coli* K12: structure-function relationships in the TraT protein. *Mol. Microbiol.* 4(8):1259-1268(1990)
46. Webb, C. D., Decatur A., Teleman A. and Losick R. Use of green fluorescent protein for ivsualization of cell specific gene expression and subcellular protein localization during sporulation in *Bacillus subtilis* J. Bacteriol. 177:5906-5911 (1995)
47. Zheng L and Losick R., Cascade regulation of spore coat gene expression in *Bacillus subtilis* J. Mol. Biol. 212: 645-660(1990)

What is claimed is:

1. A method for displaying carboxymethylcellulase on spore surface, which comprises the steps of:
   (i) preparing a recombinant vector pCSK-cotG-CMCase for spore surface protein display comprising a vector pDG1728 and a gene encoding for fusion between CotG and carboxymethylcellulase
   (ii) transforming a host cell with the recombinant vector for spore surface protein display;
   (iii) displaying the carboxymethylcellulase on a surface of a spore of the host cell; and
   (iv) recovering the spore displaying on its surface the carboxymethylcellulase.

2. The method according to claim 1 wherein the gene encoding a spore coat protein is derived from *Bacillus*.

3. The method according to claim 1 wherein the gene encoding a spore coat protein is cotG.

4. The method according to claim 1, wherein the host cell is a spore-forming Gram positive bacterium.

5. The method according to claim 4, wherein the host cell is *Bacillus*.

6. The method according to claim 1 wherein the recovering is performed in such a manner that the display of the carboxymethylcellulase on the spore surface is maximized by regulating culture time, after which culturing is terminated and the spore is then recovered.

* * * * *

SEQUENCE LISTING

<160> NUMBER OF SEQ ID NOS: 42

<210> SEQ ID NO 1
<211> LENGTH: 30
<212> TYPE: DNA
<213> ORGANISM: Artificial Sequence
<220> FEATURE:
<223> OTHER INFORMATION: spoIVA 5' primer

<400> SEQUENCE: 1
ggcagcggat ccacagtgac aagcccaatc                               30

<210> SEQ ID NO 2
<211> LENGTH: 33
<212> TYPE: DNA
<213> ORGANISM: Artificial Sequence
<220> FEATURE:
<223> OTHER INFORMATION: spoIVA 3' primer

<400> SEQUENCE: 2
tctagacgtc gaccaggatg gcgattaagc cgc                           33

<210> SEQ ID NO 3
<211> LENGTH: 30
<212> TYPE: DNA
<213> ORGANISM: Artificial Sequence
<220> FEATURE:
<223> OTHER INFORMATION: cotB 5' primer

<400> SEQUENCE: 3
cctcatggat ccgtataaaa agaatgatat                               30

<210> SEQ ID NO 4
<211> LENGTH: 33
<212> TYPE: DNA
<213> ORGANISM: Artificial Sequence
<220> FEATURE:
<223> OTHER INFORMATION: cotB 3' primer

<400> SEQUENCE: 4
ccatgacgtc gacaaattta cgtttccagt gat                           33

<210> SEQ ID NO 5
<211> LENGTH: 30
<212> TYPE: DNA
<213> ORGANISM: Artificial Sequence
<220> FEATURE:
<223> OTHER INFORMATION: cotC 5' primer

<400> SEQUENCE: 5
ctacacggat cctctatgtc aatgatagcc                                    30

<210> SEQ ID NO 6
<211> LENGTH: 33
<212> TYPE: DNA
<213> ORGANISM: Artificial Sequence
<220> FEATURE:
<223> OTHER INFORMATION: cotC 3' primer

<400> SEQUENCE: 6
ttaagacgtc gacgtagtgt tttttatgct ttt                                33

<210> SEQ ID NO 7
<211> LENGTH: 30
<212> TYPE: DNA
<213> ORGANISM: Artificial Sequence
<220> FEATURE:
<223> OTHER INFORMATION: cotD 5' primer

<400> SEQUENCE: 7
agcggcggat cctgtaaaat gacgttagtt                                    30

<210> SEQ ID NO 8
<211> LENGTH: 33
<212> TYPE: DNA
<213> ORGANISM: Artificial Sequence
<220> FEATURE:
<223> OTHER INFORMATION: cotD 3' primer

<400> SEQUENCE: 8
gtttgacgtc gacgtagtcg cagcaaggtt ttc                                33

<210> SEQ ID NO 9
<211> LENGTH: 30
<212> TYPE: DNA
<213> ORGANISM: Artificial Sequence
<220> FEATURE:
<223> OTHER INFORMATION: cotE 5' primer

<400> SEQUENCE: 9
aaccggatcc acctgctgaa aggggaaacc                                    30

<210> SEQ ID NO 10
<211> LENGTH: 32
<212> TYPE: DNA
<213> ORGANISM: Artificial Sequence
<220> FEATURE:
<223> OTHER INFORMATION: cotE 3' primer

<400> SEQUENCE: 10
gtccctgtcg acttcttcag gatctcccaa ta                                 32

<210> SEQ ID NO 11
<211> LENGTH: 30
<212> TYPE: DNA
<213> ORGANISM: Artificial Sequence
<220> FEATURE:
<223> OTHER INFORMATION: cotG 5' primer

<400> SEQUENCE: 11
gcctttggat ccagtgtccc tagctccgag                              30

<210> SEQ ID NO 12
<211> LENGTH: 33
<212> TYPE: DNA
<213> ORGANISM: Artificial Sequence
<220> FEATURE:
<223> OTHER INFORMATION: cotG 3' primer

<400> SEQUENCE: 12
aaaagacgtc gactttgtat ttcttttga cta                           33

<210> SEQ ID NO 13
<211> LENGTH: 30
<212> TYPE: DNA
<213> ORGANISM: Artificial Sequence
<220> FEATURE:
<223> OTHER INFORMATION: cotH 5' primer

<400> SEQUENCE: 13
ttttgtggat ccgagatttc ttgtgagagc                              30

<210> SEQ ID NO 14
<211> LENGTH: 36
<212> TYPE: DNA
<213> ORGANISM: Artificial Sequence
<220> FEATURE:
<223> OTHER INFORMATION: cotH 3' primer

<400> SEQUENCE: 14
tttcgacgtc gactaaaata cttaaatgat ctttga                       36

<210> SEQ ID NO 15
<211> LENGTH: 30
<212> TYPE: DNA
<213> ORGANISM: Artificial Sequence
<220> FEATURE:
<223> OTHER INFORMATION: cotM 5' primer

<400> SEQUENCE: 15
ggcaaaggat ccggctatat tgaaaacgac                              30

<210> SEQ ID NO 16
<211> LENGTH: 33
<212> TYPE: DNA
<213> ORGANISM: Artificial Sequence
<220> FEATURE:
<223> OTHER INFORMATION: cotM 3' primer

<400> SEQUENCE: 16
ctttgacgtc gacgctgaga ggaaattgaa gag                          33

<210> SEQ ID NO 17
<211> LENGTH: 30
<212> TYPE: DNA
<213> ORGANISM: Artificial Sequence
<220> FEATURE:
<223> OTHER INFORMATION: cotVWX 5' primer

<400> SEQUENCE: 17
gccaatcagg atcccttcac atatatgcca                              30

<210> SEQ ID NO 18

```
<211> LENGTH: 36
<212> TYPE: DNA
<213> ORGANISM: Artificial Sequence
<220> FEATURE:
<223> OTHER INFORMATION: cotV 3' primer

<400> SEQUENCE: 18
tgaaagatct gtcgacaagg acgtcaagtt cactaa                              36

<210> SEQ ID NO 19
<211> LENGTH: 30
<212> TYPE: DNA
<213> ORGANISM: Artificial Sequence
<220> FEATURE:
<223> OTHER INFORMATION: cotVWX 5' primer

<400> SEQUENCE: 19
gccaatcagg atcccttcac atatatgcca                                     30

<210> SEQ ID NO 20
<211> LENGTH: 36
<212> TYPE: DNA
<213> ORGANISM: Artificial Sequence
<220> FEATURE:
<223> OTHER INFORMATION: cotX 3' primer

<400> SEQUENCE: 20
ctgttgatca gtcgacgagg acaagagtga tactag                              36

<210> SEQ ID NO 21
<211> LENGTH: 30
<212> TYPE: DNA
<213> ORGANISM: Artificial Sequence
<220> FEATURE:
<223> OTHER INFORMATION: cotYZ 5' primer

<400> SEQUENCE: 21
tcatagggat cctagtattc tctcttgtcc                                     30

<210> SEQ ID NO 22
<211> LENGTH: 33
<212> TYPE: DNA
<213> ORGANISM: Artificial Sequence
<220> FEATURE:
<223> OTHER INFORMATION: cotY 3' primer

<400> SEQUENCE: 22
ttacgacgtc gactccattg tgatgatgct ttt                                 33

<210> SEQ ID NO 23
<211> LENGTH: 4000
<212> TYPE: DNA
<213> ORGANISM: Bacillus subtilis
<220> FEATURE:
<221> NAME/KEY: CDS
<222> LOCATION: (330)..(3902)

<400> SEQUENCE: 23
ggatccacct gctgaaaggg gaaaccggtt caaaggtgaa gcatttaaat aacagctgtt    60
ctctctaaac acggtgcctt tacaggcccg tgttttttta tcatttgtgc ggttaaaaat   120
gaactaaata atctatgtac caaatgttca attggttttt ctgtgctcag ccgcgtataa   180
actttatcgc acttataagt aaagtttcta ggcaccctg catacaatgg aacagaaact    240
ttgtattttt atattttatt tataaaatg cacactagac aaatgcccag cataagataa    300
```

-continued

| | |
|---|---|
| cacgaagaag aacaaggagg catgccgga atg tct gaa tac agg gaa att att<br>                                                  Met Ser Glu Tyr Arg Glu Ile Ile<br>                                                     1               5 | 353 |
| acg aag gca gta gta gcg aaa ggc cga aaa ttc acc caa tgc acc aac<br>Thr Lys Ala Val Val Ala Lys Gly Arg Lys Phe Thr Gln Cys Thr Asn<br>     10                     15                     20 | 401 |
| acc atc tcg cct gag aaa aaa ccg agc agc att ttg ggt ggt tgg att<br>Thr Ile Ser Pro Glu Lys Lys Pro Ser Ser Ile Leu Gly Gly Trp Ile<br> 25                   30                     35                     40 | 449 |
| att aac cac aag tat gac gct gaa aaa att gga aaa acg gta gaa att<br>Ile Asn His Lys Tyr Asp Ala Glu Lys Ile Gly Lys Thr Val Glu Ile<br>               45                     50                     55 | 497 |
| gaa ggg tat tat gat ata aac gta tgg tac tct tac gcg gac aac aca<br>Glu Gly Tyr Tyr Asp Ile Asn Val Trp Tyr Ser Tyr Ala Asp Asn Thr<br>               60                     65                     70 | 545 |
| aag aca gag gtt gtc aca gaa cgg gta aaa tat gta gat gtc att aaa<br>Lys Thr Glu Val Val Thr Glu Arg Val Lys Tyr Val Asp Val Ile Lys<br>     75                     80                     85 | 593 |
| ctc aga tac aga gac aat aat tac tta gat gat gag cat gaa gtg att<br>Leu Arg Tyr Arg Asp Asn Asn Tyr Leu Asp Asp Glu His Glu Val Ile<br>         90                     95                    100 | 641 |
| gcc aaa gtg ctt cag cag cca aac tgc ctt gaa gtg acc att tcg ccg<br>Ala Lys Val Leu Gln Gln Pro Asn Cys Leu Glu Val Thr Ile Ser Pro<br>105                    110                    115                 120 | 689 |
| aat gga aat aaa atc gtt gtg cag gca gaa aga gaa ttt ttg gcg gaa<br>Asn Gly Asn Lys Ile Val Val Gln Ala Glu Arg Glu Phe Leu Ala Glu<br>              125                   130                   135 | 737 |
| gtg gta ggg gaa aca aag gta gtt gtt gag gtc aat cct gac tgg gaa<br>Val Val Gly Glu Thr Lys Val Val Val Glu Val Asn Pro Asp Trp Glu<br>                  140                   145                   150 | 785 |
| gag gat gac gag gaa gat tgg gaa gat gag ctt gat gaa gag ctt gaa<br>Glu Asp Asp Glu Glu Asp Trp Glu Asp Glu Leu Asp Glu Glu Leu Glu<br>          155                   160                   165 | 833 |
| gac atc aac ccg gag ttt tta gtg gga gat cct gaa gaa gtc gac cgg<br>Asp Ile Asn Pro Glu Phe Leu Val Gly Asp Pro Glu Glu Val Asp Arg<br>      170                   175                   180 | 881 |
| gaa aac cct ggc gtt acc caa ctt aat cgc ctt gca gca cat ccc cct<br>Glu Asn Pro Gly Val Thr Gln Leu Asn Arg Leu Ala Ala His Pro Pro<br>185                    190                    195                 200 | 929 |
| ttc gcc agc tgg cgt aat agc gaa gag gcc cgc acc gat cgc cct tcc<br>Phe Ala Ser Trp Arg Asn Ser Glu Glu Ala Arg Thr Asp Arg Pro Ser<br>              205                   210                   215 | 977 |
| caa cag ttg cgc agc ctg aat ggc gaa tgg cgc ttt gcc tgg ttt ccg<br>Gln Gln Leu Arg Ser Leu Asn Gly Glu Trp Arg Phe Ala Trp Phe Pro<br>          220                   225                   230 | 1025 |
| gca cca gaa gcg gtg ccg gaa agc tgg ctg gag tgc gat ctt cct gag<br>Ala Pro Glu Ala Val Pro Glu Ser Trp Leu Glu Cys Asp Leu Pro Glu<br>             235                   240                   245 | 1073 |
| gcc gat act gtc gtc gtc ccc tca aac tgg cag atg cac ggt tac gat<br>Ala Asp Thr Val Val Val Pro Ser Asn Trp Gln Met His Gly Tyr Asp<br>250                    255                    260 | 1121 |
| gcg ccc atc tac acc aac gta acc tat ccc att acg gtc aat ccg ccg<br>Ala Pro Ile Tyr Thr Asn Val Thr Tyr Pro Ile Thr Val Asn Pro Pro<br>265                      270                    275                 280 | 1169 |
| ttt gtt ccc acg gag aat ccg acg ggt tgt tac tcg ctc aca ttt aat<br>Phe Val Pro Thr Glu Asn Pro Thr Gly Cys Tyr Ser Leu Thr Phe Asn<br>              285                   290                   295 | 1217 |
| gtt gat gaa agc tgg cta cag gaa ggc cag acg cga att att ttt gat<br>Val Asp Glu Ser Trp Leu Gln Glu Gly Gln Thr Arg Ile Ile Phe Asp<br>          300                   305                   310 | 1265 |

```
ggc gtt aac tcg gcg ttt cat ctg tgg tgc aac ggg cgc tgg gtc ggt    1313
Gly Val Asn Ser Ala Phe His Leu Trp Cys Asn Gly Arg Trp Val Gly
        315                 320                 325 tac ggc cag gac agt cgt ttg ccg tct gaa ttt gac ctg agc gca ttt    1361
Tyr Gly Gln Asp Ser Arg Leu Pro Ser Glu Phe Asp Leu Ser Ala Phe
    330                 335                 340 tta cgc gcc gga gaa aac cgc ctc gcg gtg atg gtg ctg cgt tgg agt    1409
Leu Arg Ala Gly Glu Asn Arg Leu Ala Val Met Val Leu Arg Trp Ser
345                 350                 355                 360 gac ggc agt tat ctg gaa gat cag gat atg tgg cgg atg agc ggc att    1457
Asp Gly Ser Tyr Leu Glu Asp Gln Asp Met Trp Arg Met Ser Gly Ile
                365                 370                 375 ttc cgt gac gtc tcg ttg ctg cat aaa ccg act aca caa atc agc gat    1505
Phe Arg Asp Val Ser Leu Leu His Lys Pro Thr Thr Gln Ile Ser Asp
            380                 385                 390 ttc cat gtt gcc act cgc ttt aat gat gat ttc agc cgc gct gta ctg    1553
Phe His Val Ala Thr Arg Phe Asn Asp Asp Phe Ser Arg Ala Val Leu
        395                 400                 405 gag gct gaa gtt cag atg tgc ggc gag ttg cgt gac tac cta cgg gta    1601
Glu Ala Glu Val Gln Met Cys Gly Glu Leu Arg Asp Tyr Leu Arg Val
    410                 415                 420 aca gtt tct tta tgg cag ggt gaa acg cag gtc gcc agc ggc acc gcg    1649
Thr Val Ser Leu Trp Gln Gly Glu Thr Gln Val Ala Ser Gly Thr Ala
425                 430                 435                 440 cct ttc ggc ggt gaa att atc gat gag cgt ggt ggt tat gcc gat cgc    1697
Pro Phe Gly Gly Glu Ile Ile Asp Glu Arg Gly Gly Tyr Ala Asp Arg
                445                 450                 455 gtc aca cta cgt ctg aac gtc gaa aac ccg aaa ctg tgg agc gcc gaa    1745
Val Thr Leu Arg Leu Asn Val Glu Asn Pro Lys Leu Trp Ser Ala Glu
            460                 465                 470 atc ccg aat ctc tat cgt gcg gtg gtt gaa ctg cac acc gcc gac ggc    1793
Ile Pro Asn Leu Tyr Arg Ala Val Val Glu Leu His Thr Ala Asp Gly
        475                 480                 485 acg ctg att gaa gca gaa gcc tgc gat gtc ggt ttc cgc gag gtg cgg    1841
Thr Leu Ile Glu Ala Glu Ala Cys Asp Val Gly Phe Arg Glu Val Arg
    490                 495                 500 att gaa aat ggt ctg ctg ctg ctg aac ggc aag ccg ttg ctg att cga    1889
Ile Glu Asn Gly Leu Leu Leu Leu Asn Gly Lys Pro Leu Leu Ile Arg
505                 510                 515                 520 ggc gtt aac cgt cac gag cat cat cct ctg cat ggt cag gtc atg gat    1937
Gly Val Asn Arg His Glu His His Pro Leu His Gly Gln Val Met Asp
                525                 530                 535 gag cag acg atg gtg cag gat atc ctg ctg atg aag cag aac aac ttt    1985
Glu Gln Thr Met Val Gln Asp Ile Leu Leu Met Lys Gln Asn Asn Phe
            540                 545                 550 aac gcc gtg cgc tgt tcg cat tat ccg aac cat ccg ctg tgg tac acg    2033
Asn Ala Val Arg Cys Ser His Tyr Pro Asn His Pro Leu Trp Tyr Thr
        555                 560                 565 ctg tgc gac cgc tac ggc ctg tat gtg gtg gat gaa gcc aat att gaa    2081
Leu Cys Asp Arg Tyr Gly Leu Tyr Val Val Asp Glu Ala Asn Ile Glu
    570                 575                 580 acc cac ggc atg gtg cca atg aat cgt ctg acc gat gat ccg cgc tgg    2129
Thr His Gly Met Val Pro Met Asn Arg Leu Thr Asp Asp Pro Arg Trp
585                 590                 595                 600 cta ccg gcg atg agc gaa cgc gta acg cga atg gtg cag cgc gat cgt    2177
Leu Pro Ala Met Ser Glu Arg Val Thr Arg Met Val Gln Arg Asp Arg
                605                 610                 615 aat cac ccg agt gtg atc atc tgg tcg ctg ggg aat gaa tca ggc cac    2225
Asn His Pro Ser Val Ile Ile Trp Ser Leu Gly Asn Glu Ser Gly His
```

-continued

```
                620                     625                     630
ggc gct aat cac gac gcg ctg tat cgc tgg atc aaa tct gtc gat cct      2273
Gly Ala Asn His Asp Ala Leu Tyr Arg Trp Ile Lys Ser Val Asp Pro
        635                     640                     645 tcc cgc ccg gtg cag tat gaa ggc ggc gga gcc gac acc acg gcc acc      2321
Ser Arg Pro Val Gln Tyr Glu Gly Gly Gly Ala Asp Thr Thr Ala Thr
650                     655                     660 gat att att tgc ccg atg tac gcg cgc gtg gat gaa gac cag ccc ttc      2369
Asp Ile Ile Cys Pro Met Tyr Ala Arg Val Asp Glu Asp Gln Pro Phe
665                     670                     675                 680 ccg gct gtg ccg aaa tgg tcc atc aaa aaa tgg ctt tcg cta cct gga      2417
Pro Ala Val Pro Lys Trp Ser Ile Lys Lys Trp Leu Ser Leu Pro Gly
                685                     690                     695 gag acg cgc ccg ctg atc ctt tgc gaa tac gcc cac gcg atg ggt aac      2465
Glu Thr Arg Pro Leu Ile Leu Cys Glu Tyr Ala His Ala Met Gly Asn
            700                     705                     710 agt ctt ggc ggt ttc gct aaa tac tgg cag gcg ttt cgt cag tat ccc      2513
Ser Leu Gly Gly Phe Ala Lys Tyr Trp Gln Ala Phe Arg Gln Tyr Pro
        715                     720                     725 cgt tta cag ggc ggc ttc gtc tgg gac tgg gtg gat cag tcg ctg att      2561
Arg Leu Gln Gly Gly Phe Val Trp Asp Trp Val Asp Gln Ser Leu Ile
730                     735                     740 aaa tat gat gaa aac ggc aac ccg tgg tcg gct tac ggc ggt gat ttt      2609
Lys Tyr Asp Glu Asn Gly Asn Pro Trp Ser Ala Tyr Gly Gly Asp Phe
745                     750                     755                 760 ggc gat acg ccg aac gat cgc cag ttc tgt atg aac ggt ctg gtc ttt      2657
Gly Asp Thr Pro Asn Asp Arg Gln Phe Cys Met Asn Gly Leu Val Phe
                765                     770                     775 gcc gac cgc acg ccg cat cca gcg ctg acg gaa gca aaa cac cag cag      2705
Ala Asp Arg Thr Pro His Pro Ala Leu Thr Glu Ala Lys His Gln Gln
            780                     785                     790 cag ttt ttc cag ttc cgt tta tcc ggg caa acc atc gaa gtg acc agc      2753
Gln Phe Phe Gln Phe Arg Leu Ser Gly Gln Thr Ile Glu Val Thr Ser
        795                     800                     805 gaa tac ctg ttc cgt cat agc gat aac gag ctc ctg cac tgg atg gtg      2801
Glu Tyr Leu Phe Arg His Ser Asp Asn Glu Leu Leu His Trp Met Val
810                     815                     820 gcg ctg gat ggt aag ccg ctg gca agc ggt gaa gtg cct ctg gat gtc      2849
Ala Leu Asp Gly Lys Pro Leu Ala Ser Gly Glu Val Pro Leu Asp Val
825                     830                     835                 840 gct cca caa ggt aaa cag ttg att gaa ctg cct gaa cta ccg cag ccg      2897
Ala Pro Gln Gly Lys Gln Leu Ile Glu Leu Pro Glu Leu Pro Gln Pro
                845                     850                     855 gag agc gcc ggg caa ctc tgg ctc aca gta cgc gta gtg caa ccg aac      2945
Glu Ser Ala Gly Gln Leu Trp Leu Thr Val Arg Val Val Gln Pro Asn
            860                     865                     870 gcg acc gca tgg tca gaa gcc ggg cac atc agc gcc tgg cag cag tgg      2993
Ala Thr Ala Trp Ser Glu Ala Gly His Ile Ser Ala Trp Gln Gln Trp
        875                     880                     885 cgt ctg gcg gaa aac ctc agt gtg acg ctc ccc gcc gcg tcc cac gcc      3041
Arg Leu Ala Glu Asn Leu Ser Val Thr Leu Pro Ala Ala Ser His Ala
890                     895                     900 atc ccg cat ctg acc acc agc gaa atg gat ttt tgc atc gag ctg ggt      3089
Ile Pro His Leu Thr Thr Ser Glu Met Asp Phe Cys Ile Glu Leu Gly
905                     910                     915                 920 aat aag cgt tgg caa ttt aac cgc cag tca ggc ttt ctt tca cag atg      3137
Asn Lys Arg Trp Gln Phe Asn Arg Gln Ser Gly Phe Leu Ser Gln Met
                925                     930                     935 tgg att ggc gat aaa aaa caa ctg ctg acg ccg ctg cgc gat cag ttc      3185
Trp Ile Gly Asp Lys Lys Gln Leu Leu Thr Pro Leu Arg Asp Gln Phe
```

```
Trp Ile Gly Asp Lys Lys Gln Leu Leu Thr Pro Leu Arg Asp Gln Phe
                940                 945                 950 acc cgt gca ccg ctg gat aac gac att ggc gta agt gaa gcg acc cgc    3233
Thr Arg Ala Pro Leu Asp Asn Asp Ile Gly Val Ser Glu Ala Thr Arg
            955                 960                 965 att gac cct aac gcc tgg gtc gaa cgc tgg aag gcg gcg ggc cat tac    3281
Ile Asp Pro Asn Ala Trp Val Glu Arg Trp Lys Ala Ala Gly His Tyr
970                 975                 980 cag gcc gaa gca gcg ttg ttg cag tgc acg gca gat aca ctt gct gat    3329
Gln Ala Glu Ala Ala Leu Leu Gln Cys Thr Ala Asp Thr Leu Ala Asp
985                 990                 995                 1000 gcg gtg ctg att acg acc gct cac gcg tgg cag cat cag ggg aaa acc    3377
Ala Val Leu Ile Thr Thr Ala His Ala Trp Gln His Gln Gly Lys Thr
                1005                1010                1015 tta ttt atc agc cgg aaa acc tac cgg att gat ggt agt ggt caa atg    3425
Leu Phe Ile Ser Arg Lys Thr Tyr Arg Ile Asp Gly Ser Gly Gln Met
            1020                1025                1030 gcg att acc gtt gat gtt gaa gtg gcg agc gat aca ccg cat ccg gcg    3473
Ala Ile Thr Val Asp Val Glu Val Ala Ser Asp Thr Pro His Pro Ala
        1035                1040                1045 cgg att ggc ctg aac tgc cag ctg gcg cag gta gca gag cgg gta aac    3521
Arg Ile Gly Leu Asn Cys Gln Leu Ala Gln Val Ala Glu Arg Val Asn
    1050                1055                1060 tgg ctc gga tta ggg ccg caa gaa aac tat ccc gac cgc ctt act gcc    3569
Trp Leu Gly Leu Gly Pro Gln Glu Asn Tyr Pro Asp Arg Leu Thr Ala
1065                1070                1075                1080 gcc tgt ttt gac cgc tgg gat ctg cca ttg tca gac atg tat acc ccg    3617
Ala Cys Phe Asp Arg Trp Asp Leu Pro Leu Ser Asp Met Tyr Thr Pro
                1085                1090                1095 tac gtc ttc ccg agc gaa aac ggt ctg cgc tgc ggg acg cgc gaa ttg    3665
Tyr Val Phe Pro Ser Glu Asn Gly Leu Arg Cys Gly Thr Arg Glu Leu
            1100                1105                1110 aat tat ggc cca cac cag tgg cgc ggc gac ttc cag ttc aac atc agc    3713
Asn Tyr Gly Pro His Gln Trp Arg Gly Asp Phe Gln Phe Asn Ile Ser
        1115                1120                1125 cgc tac agt caa cag caa ctg atg gaa acc agc cat cgc cat ctg ctg    3761
Arg Tyr Ser Gln Gln Gln Leu Met Glu Thr Ser His Arg His Leu Leu
    1130                1135                1140 cac gcg gaa gaa ggc aca tgg ctg aat atc gac ggt ttc cat atg ggg    3809
His Ala Glu Glu Gly Thr Trp Leu Asn Ile Asp Gly Phe His Met Gly
1145                1150                1155                1160 att ggt ggc gac gac tcc tgg agc ccg tca gta tcg gcg gaa ttt cag    3857
Ile Gly Gly Asp Asp Ser Trp Ser Pro Ser Val Ser Ala Glu Phe Gln
                1165                1170                1175 ctg agc gcc ggt cgc tac cat tac cag ttg gtc tgg tgt caa aaa       3902
Leu Ser Ala Gly Arg Tyr His Tyr Gln Leu Val Trp Cys Gln Lys
            1180                1185                1190 taataata accgggcagg ccatgtctgc ccgtatttcg cgtaaggaaa tccattatgt   3960
actatcgatc agaccagttt ttaatttgtg tgtttccatg                         4000

<210> SEQ ID NO 24
<211> LENGTH: 1191
<212> TYPE: PRT
<213> ORGANISM: Bacillus subtilis

<400> SEQUENCE: 24

Met Ser Glu Tyr Arg Glu Ile Ile Thr Lys Ala Val Val Ala Lys Gly
1               5                   10                  15

Arg Lys Phe Thr Gln Cys Thr Asn Thr Ile Ser Pro Glu Lys Lys Pro
```

```
                20                  25                  30
Ser Ser Ile Leu Gly Gly Trp Ile Ile Asn His Lys Tyr Asp Ala Glu
        35                  40                  45

Lys Ile Gly Lys Thr Val Glu Ile Glu Gly Tyr Tyr Asp Ile Asn Val
    50                  55                  60

Trp Tyr Ser Tyr Ala Asp Asn Thr Lys Thr Glu Val Val Thr Glu Arg
65                  70                  75                  80

Val Lys Tyr Val Asp Val Ile Lys Leu Arg Tyr Arg Asp Asn Asn Tyr
                85                  90                  95

Leu Asp Asp Glu His Glu Val Ile Ala Lys Val Leu Gln Gln Pro Asn
            100                 105                 110

Cys Leu Glu Val Thr Ile Ser Pro Asn Gly Asn Lys Ile Val Val Gln
        115                 120                 125

Ala Glu Arg Glu Phe Leu Ala Glu Val Val Gly Glu Thr Lys Val Val
    130                 135                 140

Val Glu Val Asn Pro Asp Trp Glu Glu Asp Glu Glu Asp Trp Glu
145                 150                 155                 160

Asp Glu Leu Asp Glu Glu Leu Glu Asp Ile Asn Pro Glu Phe Leu Val
                165                 170                 175

Gly Asp Pro Glu Glu Val Asp Arg Glu Asn Pro Gly Val Thr Gln Leu
            180                 185                 190

Asn Arg Leu Ala Ala His Pro Pro Phe Ala Ser Trp Arg Asn Ser Glu
        195                 200                 205

Glu Ala Arg Thr Asp Arg Pro Ser Gln Gln Leu Arg Ser Leu Asn Gly
    210                 215                 220

Glu Trp Arg Phe Ala Trp Phe Pro Ala Pro Glu Ala Val Pro Glu Ser
225                 230                 235                 240

Trp Leu Glu Cys Asp Leu Pro Glu Ala Asp Thr Val Val Pro Ser
                245                 250                 255

Asn Trp Gln Met His Gly Tyr Asp Ala Pro Ile Tyr Thr Asn Val Thr
            260                 265                 270

Tyr Pro Ile Thr Val Asn Pro Pro Phe Val Pro Thr Glu Asn Pro Thr
        275                 280                 285

Gly Cys Tyr Ser Leu Thr Phe Asn Val Asp Glu Ser Trp Leu Gln Glu
    290                 295                 300

Gly Gln Thr Arg Ile Ile Phe Asp Gly Val Asn Ser Ala Phe His Leu
305                 310                 315                 320

Trp Cys Asn Gly Arg Trp Val Gly Tyr Gly Gln Asp Ser Arg Leu Pro
                325                 330                 335

Ser Glu Phe Asp Leu Ser Ala Phe Leu Arg Ala Gly Glu Asn Arg Leu
            340                 345                 350

Ala Val Met Val Leu Arg Trp Ser Asp Gly Ser Tyr Leu Glu Asp Gln
        355                 360                 365

Asp Met Trp Arg Met Ser Gly Ile Phe Arg Asp Val Ser Leu Leu His
    370                 375                 380

Lys Pro Thr Thr Gln Ile Ser Asp Phe His Val Ala Thr Arg Phe Asn
385                 390                 395                 400

Asp Asp Phe Ser Arg Ala Val Leu Glu Ala Glu Val Gln Met Cys Gly
                405                 410                 415

Glu Leu Arg Asp Tyr Leu Arg Val Thr Val Ser Leu Trp Gln Gly Glu
            420                 425                 430

Thr Gln Val Ala Ser Gly Thr Ala Pro Phe Gly Gly Glu Ile Ile Asp
        435                 440                 445
```

-continued

Glu Arg Gly Gly Tyr Ala Asp Arg Val Thr Leu Arg Leu Asn Val Glu
    450                 455                 460

Asn Pro Lys Leu Trp Ser Ala Glu Ile Pro Asn Leu Tyr Arg Ala Val
465                 470                 475                 480

Val Glu Leu His Thr Ala Asp Gly Thr Leu Ile Glu Ala Glu Ala Cys
                    485                 490                 495

Asp Val Gly Phe Arg Glu Val Arg Ile Glu Asn Gly Leu Leu Leu Leu
                500                 505                 510

Asn Gly Lys Pro Leu Leu Ile Arg Gly Val Asn Arg His Glu His His
            515                 520                 525

Pro Leu His Gly Gln Val Met Asp Glu Gln Thr Met Val Gln Asp Ile
530                 535                 540

Leu Leu Met Lys Gln Asn Asn Phe Asn Ala Val Arg Cys Ser His Tyr
545                 550                 555                 560

Pro Asn His Pro Leu Trp Tyr Thr Leu Cys Asp Arg Tyr Gly Leu Tyr
                565                 570                 575

Val Val Asp Glu Ala Asn Ile Glu Thr His Gly Met Val Pro Met Asn
            580                 585                 590

Arg Leu Thr Asp Asp Pro Arg Trp Leu Pro Ala Met Ser Glu Arg Val
        595                 600                 605

Thr Arg Met Val Gln Arg Asp Arg Asn His Pro Ser Val Ile Ile Trp
    610                 615                 620

Ser Leu Gly Asn Glu Ser Gly His Gly Ala Asn His Asp Ala Leu Tyr
625                 630                 635                 640

Arg Trp Ile Lys Ser Val Asp Pro Ser Arg Pro Val Gln Tyr Glu Gly
                645                 650                 655

Gly Gly Ala Asp Thr Thr Ala Thr Asp Ile Ile Cys Pro Met Tyr Ala
            660                 665                 670

Arg Val Asp Glu Asp Gln Pro Phe Pro Ala Val Pro Lys Trp Ser Ile
        675                 680                 685

Lys Lys Trp Leu Ser Leu Pro Gly Glu Thr Arg Pro Leu Ile Leu Cys
    690                 695                 700

Glu Tyr Ala His Ala Met Gly Asn Ser Leu Gly Gly Phe Ala Lys Tyr
705                 710                 715                 720

Trp Gln Ala Phe Arg Gln Tyr Pro Arg Leu Gln Gly Gly Phe Val Trp
                725                 730                 735

Asp Trp Val Asp Gln Ser Leu Ile Lys Tyr Asp Glu Asn Gly Asn Pro
            740                 745                 750

Trp Ser Ala Tyr Gly Gly Asp Phe Gly Asp Thr Pro Asn Asp Arg Gln
        755                 760                 765

Phe Cys Met Asn Gly Leu Val Phe Ala Asp Arg Thr Pro His Pro Ala
    770                 775                 780

Leu Thr Glu Ala Lys His Gln Gln Gln Phe Phe Gln Phe Arg Leu Ser
785                 790                 795                 800

Gly Gln Thr Ile Glu Val Thr Ser Glu Tyr Leu Phe Arg His Ser Asp
                805                 810                 815

Asn Glu Leu Leu His Trp Met Val Ala Leu Asp Gly Lys Pro Leu Ala
            820                 825                 830

Ser Gly Glu Val Pro Leu Asp Val Ala Pro Gln Gly Lys Gln Leu Ile
        835                 840                 845

Glu Leu Pro Glu Leu Pro Gln Pro Glu Ser Ala Gly Gln Leu Trp Leu
850                 855                 860

```
Thr Val Arg Val Val Gln Pro Asn Ala Thr Ala Trp Ser Glu Ala Gly
865                 870                 875                 880

His Ile Ser Ala Trp Gln Gln Trp Arg Leu Ala Glu Asn Leu Ser Val
            885                 890                 895

Thr Leu Pro Ala Ala Ser His Ala Ile Pro His Leu Thr Thr Ser Glu
        900                 905                 910

Met Asp Phe Cys Ile Glu Leu Gly Asn Lys Arg Trp Gln Phe Asn Arg
    915                 920                 925

Gln Ser Gly Phe Leu Ser Gln Met Trp Ile Gly Asp Lys Lys Gln Leu
930                 935                 940

Leu Thr Pro Leu Arg Asp Gln Phe Thr Arg Ala Pro Leu Asp Asn Asp
945                 950                 955                 960

Ile Gly Val Ser Glu Ala Thr Arg Ile Asp Pro Asn Ala Trp Val Glu
                965                 970                 975

Arg Trp Lys Ala Ala Gly His Tyr Gln Ala Glu Ala Ala Leu Leu Gln
            980                 985                 990

Cys Thr Ala Asp Thr Leu Ala Asp Ala Val Leu Ile Thr Thr Ala His
        995                 1000                1005

Ala Trp Gln His Gln Gly Lys Thr Leu Phe Ile Ser Arg Lys Thr Tyr
    1010                1015                1020

Arg Ile Asp Gly Ser Gly Gln Met Ala Ile Thr Val Asp Val Glu Val
1025                1030                1035                1040

Ala Ser Asp Thr Pro His Pro Ala Arg Ile Gly Leu Asn Cys Gln Leu
                1045                1050                1055

Ala Gln Val Ala Glu Arg Val Asn Trp Leu Gly Leu Gly Pro Gln Glu
            1060                1065                1070

Asn Tyr Pro Asp Arg Leu Thr Ala Ala Cys Phe Asp Arg Trp Asp Leu
        1075                1080                1085

Pro Leu Ser Asp Met Tyr Thr Pro Tyr Val Phe Pro Ser Glu Asn Gly
    1090                1095                1100

Leu Arg Cys Gly Thr Arg Glu Leu Asn Tyr Gly Pro His Gln Trp Arg
1105                1110                1115                1120

Gly Asp Phe Gln Phe Asn Ile Ser Arg Tyr Ser Gln Gln Leu Met
                1125                1130                1135

Glu Thr Ser His Arg His Leu Leu His Ala Glu Glu Gly Thr Trp Leu
            1140                1145                1150

Asn Ile Asp Gly Phe His Met Gly Ile Gly Gly Asp Asp Ser Trp Ser
        1155                1160                1165

Pro Ser Val Ser Ala Glu Phe Gln Leu Ser Ala Gly Arg Tyr His Tyr
    1170                1175                1180

Gln Leu Val Trp Cys Gln Lys
1185                1190

<210> SEQ ID NO 25
<211> LENGTH: 4173
<212> TYPE: DNA
<213> ORGANISM: Bacillus subtilis
<220> FEATURE:
<221> NAME/KEY: CDS
<222> LOCATION: (461)..(4075)

<400> SEQUENCE: 25
ggatccagtg tccctagctc cgagaaaaaa tccagagaca atttgtttct catcaaggaa      60
gggtctttat actccgcatt taagtgaatc tctcgcgcgc cgcggaatgt tttcggctga     120
taaaaggaaa tatggtatga cttcttttttg aagtctctga tatgtgatcc ccgataagcg     180
```

-continued

```
atatcaatat ccagccttttt ttgatttacc ttcatcacag ctggcaccgg atcatcgtcc    240
catatatcct tttttaattc acgcaagtct tttggatgaa caaacagctg ataaagcggt    300
aaattggatt gattcttcat ccataatcct ccttacaaat tttaggcttt tatttttata    360
agatctcagc ggaacactta tacactttt aaaaccgcgc gtactatgag ggtagtaagg    420
atcttcatcc ttaacatatt tttaaaagga ggatttcaaa ttg ggc cac tat tcc    475
                                               Leu Gly His Tyr Ser
                                                1               5 cat tct gac atc gaa gaa gcg gtg aaa tcc gca aaa aaa gaa ggt tta    523
His Ser Asp Ile Glu Glu Ala Val Lys Ser Ala Lys Lys Glu Gly Leu
             10                  15                  20 aag gat tat tta tac caa gag cct cat gga aaa aaa cgc agt cat aaa    571
Lys Asp Tyr Leu Tyr Gln Glu Pro His Gly Lys Lys Arg Ser His Lys
         25                  30                  35 aag tcg cac cgc act cac aaa aaa tct cgc agc cat aaa aaa tca tac    619
Lys Ser His Arg Thr His Lys Lys Ser Arg Ser His Lys Lys Ser Tyr
     40                  45                  50 tgc tct cac aaa aaa tct cgc agt cac aaa aaa tca ttc tgt tct cac    667
Cys Ser His Lys Lys Ser Arg Ser His Lys Lys Ser Phe Cys Ser His
 55                  60                  65 aaa aaa tct cgc agc cac aaa aaa tca tac tgc tct cac aag aaa tct    715
Lys Lys Ser Arg Ser His Lys Lys Ser Tyr Cys Ser His Lys Lys Ser
 70                  75                  80                  85 cgc agc cac aaa aaa tcg tac cgt tct cac aaa aaa tct cgc agc tat    763
Arg Ser His Lys Lys Ser Tyr Arg Ser His Lys Lys Ser Arg Ser Tyr
         90                  95                 100 aaa aaa tct tac cgt tct tac aaa aaa tct cgt agc tat aaa aaa tct    811
Lys Lys Ser Tyr Arg Ser Tyr Lys Lys Ser Arg Ser Tyr Lys Lys Ser
        105                 110                 115 tgc cgt tct tac aaa aaa tct cgc agc tac aaa aag tct tac tgt tct    859
Cys Arg Ser Tyr Lys Lys Ser Arg Ser Tyr Lys Lys Ser Tyr Cys Ser
        120                 125                 130 cac aag aaa aaa tct cgc agc tat aag aag tca tgc cgc aca cac aaa    907
His Lys Lys Lys Ser Arg Ser Tyr Lys Lys Ser Cys Arg Thr His Lys
135                 140                 145 aaa tct tat cgt tcc cat aag aaa tac tac aaa aaa ccg cac cac cac    955
Lys Ser Tyr Arg Ser His Lys Lys Tyr Tyr Lys Lys Pro His His His
150                 155                 160                 165 tgc gac gac tac aaa aga cac gat gat tat gac agc aaa aaa gaa tac   1003
Cys Asp Asp Tyr Lys Arg His Asp Asp Tyr Asp Ser Lys Lys Glu Tyr
                170                 175                 180 tgg aaa gac ggc aat tgc tgg gta gtc aaa aag aaa tac aaa gtc gac   1051
Trp Lys Asp Gly Asn Cys Trp Val Val Lys Lys Lys Tyr Lys Val Asp
            185                 190                 195 cgg gaa aac cct ggc gtt acc caa ctt aat cgc ctt gca gca cat ccc   1099
Arg Glu Asn Pro Gly Val Thr Gln Leu Asn Arg Leu Ala Ala His Pro
        200                 205                 210 cct ttc gcc agc tgg cgt aat agc gaa gag gcc cgc acc gat cgc cct   1147
Pro Phe Ala Ser Trp Arg Asn Ser Glu Glu Ala Arg Thr Asp Arg Pro
    215                 220                 225 tcc caa cag ttg cgc agc ctg aat ggc gaa tgg cgc ttt gcc tgg ttt   1195
Ser Gln Gln Leu Arg Ser Leu Asn Gly Glu Trp Arg Phe Ala Trp Phe
230                 235                 240                 245 ccg gca cca gaa gcg gtg ccg gaa agc tgg ctg gag tgc gat ctt cct   1243
Pro Ala Pro Glu Ala Val Pro Glu Ser Trp Leu Glu Cys Asp Leu Pro
                250                 255                 260 gag gcc gat act gtc gtc gtc ccc tca aac tgg cag atg cac ggt tac   1291
Glu Ala Asp Thr Val Val Val Pro Ser Asn Trp Gln Met His Gly Tyr
```

-continued

```
                    265                 270                 275
gat gcg ccc atc tac acc aac gta acc tat ccc att acg gtc aat ccg     1339
Asp Ala Pro Ile Tyr Thr Asn Val Thr Tyr Pro Ile Thr Val Asn Pro
        280                 285                 290 ccg ttt gtt ccc acg gag aat ccg acg ggt tgt tac tcg ctc aca ttt     1387
Pro Phe Val Pro Thr Glu Asn Pro Thr Gly Cys Tyr Ser Leu Thr Phe
295                 300                 305 aat gtt gat gaa agc tgg cta cag gaa ggc cag acg cga att att ttt     1435
Asn Val Asp Glu Ser Trp Leu Gln Glu Gly Gln Thr Arg Ile Ile Phe
            310                 315                 320         325 gat ggc gtt aac tcg gcg ttt cat ctg tgg tgc aac ggg cgc tgg gtc     1483
Asp Gly Val Asn Ser Ala Phe His Leu Trp Cys Asn Gly Arg Trp Val
                330                 335                 340 ggt tac ggc cag gac agt cgt ttg ccg tct gaa ttt gac ctg agc gca     1531
Gly Tyr Gly Gln Asp Ser Arg Leu Pro Ser Glu Phe Asp Leu Ser Ala
                    345                 350                 355 ttt tta cgc gcc gga gaa aac cgc ctc gcg gtg atg gtg ctg cgt tgg     1579
Phe Leu Arg Ala Gly Glu Asn Arg Leu Ala Val Met Val Leu Arg Trp
                        360                 365                 370 agt gac ggc agt tat ctg gaa gat cag gat atg tgg cgg atg agc ggc     1627
Ser Asp Gly Ser Tyr Leu Glu Asp Gln Asp Met Trp Arg Met Ser Gly
375                 380                 385 att ttc cgt gac gtc tcg ttg ctg cat aaa ccg act aca caa atc agc     1675
Ile Phe Arg Asp Val Ser Leu Leu His Lys Pro Thr Thr Gln Ile Ser
            390                 395                 400         405 gat ttc cat gtt gcc act cgc ttt aat gat gat ttc agc cgc gct gta     1723
Asp Phe His Val Ala Thr Arg Phe Asn Asp Asp Phe Ser Arg Ala Val
                410                 415                 420 ctg gag gct gaa gtt cag atg tgc ggc gag ttg cgt gac tac cta cgg     1771
Leu Glu Ala Glu Val Gln Met Cys Gly Glu Leu Arg Asp Tyr Leu Arg
                    425                 430                 435 gta aca gtt tct tta tgg cag ggt gaa acg cag gtc gcc agc ggc acc     1819
Val Thr Val Ser Leu Trp Gln Gly Glu Thr Gln Val Ala Ser Gly Thr
                        440                 445                 450 gcg cct ttc ggc ggt gaa att atc gat gag cgt ggt ggt tat gcc gat     1867
Ala Pro Phe Gly Gly Glu Ile Ile Asp Glu Arg Gly Gly Tyr Ala Asp
455                 460                 465 cgc gtc aca cta cgt ctg aac gtc gaa aac ccg aaa ctg tgg agc gcc     1915
Arg Val Thr Leu Arg Leu Asn Val Glu Asn Pro Lys Leu Trp Ser Ala
470                 475                 480                 485 gaa atc ccg aat ctc tat cgt gcg gtg gtt gaa ctg cac acc gcc gac     1963
Glu Ile Pro Asn Leu Tyr Arg Ala Val Val Glu Leu His Thr Ala Asp
                490                 495                 500 ggc acg ctg att gaa gca gaa gcc tgc gat gtc ggt ttc cgc gag gtg     2011
Gly Thr Leu Ile Glu Ala Glu Ala Cys Asp Val Gly Phe Arg Glu Val
                505                 510                 515 cgg att gaa aat ggt ctg ctg ctg ctg aac ggc aag ccg ttg ctg att     2059
Arg Ile Glu Asn Gly Leu Leu Leu Leu Asn Gly Lys Pro Leu Leu Ile
                    520                 525                 530 cga ggc gtt aac cgt cac gag cat cat cct ctg cat ggt cag gtc atg     2107
Arg Gly Val Asn Arg His Glu His His Pro Leu His Gly Gln Val Met
535                 540                 545 gat gag cag acg atg gtg cag gat atc ctg ctg atg aag cag aac aac     2155
Asp Glu Gln Thr Met Val Gln Asp Ile Leu Leu Met Lys Gln Asn Asn
550                 555                 560                 565 ttt aac gcc gtg cgc tgt tcg cat tat ccg aac cat ccg ctg tgg tac     2203
Phe Asn Ala Val Arg Cys Ser His Tyr Pro Asn His Pro Leu Trp Tyr
                570                 575                 580 acg ctg tgc gac cgc tac ggc ctg tat gtg gtg gat gaa gcc aat att     2251
```

```
      Thr Leu Cys Asp Arg Tyr Gly Leu Tyr Val Val Asp Glu Ala Asn Ile
                  585                 590                 595 gaa acc cac ggc atg gtg cca atg aat cgt ctg acc gat gat ccg cgc      2299
Glu Thr His Gly Met Val Pro Met Asn Arg Leu Thr Asp Asp Pro Arg
            600                 605                 610 tgg cta ccg gcg atg agc gaa cgc gta acg cga atg gtg cag cgc gat      2347
Trp Leu Pro Ala Met Ser Glu Arg Val Thr Arg Met Val Gln Arg Asp
        615                 620                 625 cgt aat cac ccg agt gtg atc atc tgg tcg ctg ggg aat gaa tca ggc      2395
Arg Asn His Pro Ser Val Ile Ile Trp Ser Leu Gly Asn Glu Ser Gly
630                 635                 640                 645 cac ggc gct aat cac gac gcg ctg tat cgc tgg atc aaa tct gtc gat      2443
His Gly Ala Asn His Asp Ala Leu Tyr Arg Trp Ile Lys Ser Val Asp
                650                 655                 660 cct tcc cgc ccg gtg cag tat gaa ggc ggc gga gcc gac acc acg gcc      2491
Pro Ser Arg Pro Val Gln Tyr Glu Gly Gly Gly Ala Asp Thr Thr Ala
            665                 670                 675 acc gat att att tgc ccg atg tac gcg cgc gtg gat gaa gac cag ccc      2539
Thr Asp Ile Ile Cys Pro Met Tyr Ala Arg Val Asp Glu Asp Gln Pro
        680                 685                 690 ttc ccg gct gtg ccg aaa tgg tcc atc aaa aaa tgg ctt tcg cta cct      2587
Phe Pro Ala Val Pro Lys Trp Ser Ile Lys Lys Trp Leu Ser Leu Pro
695                 700                 705 gga gag acg cgc ccg ctg atc ctt tgc gaa tac gcc cac gcg atg ggt      2635
Gly Glu Thr Arg Pro Leu Ile Leu Cys Glu Tyr Ala His Ala Met Gly
710                 715                 720                 725 aac agt ctt ggc ggt ttc gct aaa tac tgg cag gcg ttt cgt cag tat      2683
Asn Ser Leu Gly Gly Phe Ala Lys Tyr Trp Gln Ala Phe Arg Gln Tyr
                730                 735                 740 ccc cgt tta cag ggc ggc ttc gtc tgg gac tgg gtg gat cag tcg ctg      2731
Pro Arg Leu Gln Gly Gly Phe Val Trp Asp Trp Val Asp Gln Ser Leu
            745                 750                 755 att aaa tat gat gaa aac ggc aac ccg tgg tcg gct tac ggc ggt gat      2779
Ile Lys Tyr Asp Glu Asn Gly Asn Pro Trp Ser Ala Tyr Gly Gly Asp
        760                 765                 770 ttt ggc gat acg ccg aac gat cgc cag ttc tgt atg aac ggt ctg gtc      2827
Phe Gly Asp Thr Pro Asn Asp Arg Gln Phe Cys Met Asn Gly Leu Val
775                 780                 785 ttt gcc gac cgc acg ccg cat cca gcg ctg acg gaa gca aaa cac cag      2875
Phe Ala Asp Arg Thr Pro His Pro Ala Leu Thr Glu Ala Lys His Gln
790                 795                 800                 805 cag cag ttt ttc cag ttc cgt tta tcc ggg caa acc atc gaa gtg acc      2923
Gln Gln Phe Phe Gln Phe Arg Leu Ser Gly Gln Thr Ile Glu Val Thr
                810                 815                 820 agc gaa tac ctg ttc cgt cat agc gat aac gag ctc ctg cac tgg atg      2971
Ser Glu Tyr Leu Phe Arg His Ser Asp Asn Glu Leu Leu His Trp Met
            825                 830                 835 gtg gcg ctg gat ggt aag ccg ctg gca agc ggt gaa gtg cct ctg gat      3019
Val Ala Leu Asp Gly Lys Pro Leu Ala Ser Gly Glu Val Pro Leu Asp
        840                 845                 850 gtc gct cca caa ggt aaa cag ttg att gaa ctg cct gaa cta ccg cag      3067
Val Ala Pro Gln Gly Lys Gln Leu Ile Glu Leu Pro Glu Leu Pro Gln
855                 860                 865 ccg gag agc gcc ggg caa ctc tgg ctc aca gta cgc gta gtg caa ccg      3115
Pro Glu Ser Ala Gly Gln Leu Trp Leu Thr Val Arg Val Val Gln Pro
870                 875                 880                 885 aac gcg acc gca tgg tca gaa gcc ggg cac atc agc gcc tgg cag cag      3163
Asn Ala Thr Ala Trp Ser Glu Ala Gly His Ile Ser Ala Trp Gln Gln
                890                 895                 900
```

```
tgg cgt ctg gcg gaa aac ctc agt gtg acg ctc ccc gcc gcg tcc cac     3211
Trp Arg Leu Ala Glu Asn Leu Ser Val Thr Leu Pro Ala Ala Ser His
            905                 910                 915 gcc atc ccg cat ctg acc acc agc gaa atg gat ttt tgc atc gag ctg     3259
Ala Ile Pro His Leu Thr Thr Ser Glu Met Asp Phe Cys Ile Glu Leu
            920                 925                 930 ggt aat aag cgt tgg caa ttt aac cgc cag tca ggc ttt ctt tca cag     3307
Gly Asn Lys Arg Trp Gln Phe Asn Arg Gln Ser Gly Phe Leu Ser Gln
935                 940                 945 atg tgg att ggc gat aaa aaa caa ctg ctg acg ccg ctg cgc gat cag     3355
Met Trp Ile Gly Asp Lys Lys Gln Leu Leu Thr Pro Leu Arg Asp Gln
950                 955                 960                 965 ttc acc cgt gca ccg ctg gat aac gac att ggc gta agt gaa gcg acc     3403
Phe Thr Arg Ala Pro Leu Asp Asn Asp Ile Gly Val Ser Glu Ala Thr
                970                 975                 980 cgc att gac cct aac gcc tgg gtc gaa cgc tgg aag gcg gcg ggc cat     3451
Arg Ile Asp Pro Asn Ala Trp Val Glu Arg Trp Lys Ala Ala Gly His
            985                 990                 995 tac cag gcc gaa gca gcg ttg ttg cag tgc acg gca gat aca ctt gct     3499
Tyr Gln Ala Glu Ala Ala Leu Leu Gln Cys Thr Ala Asp Thr Leu Ala
            1000                1005                1010 gat gcg gtg ctg att acg acc gct cac gcg tgg cag cat cag ggg aaa     3547
Asp Ala Val Leu Ile Thr Thr Ala His Ala Trp Gln His Gln Gly Lys
            1015                1020                1025 acc tta ttt atc agc cgg aaa acc tac cgg att gat ggt agt ggt caa     3595
Thr Leu Phe Ile Ser Arg Lys Thr Tyr Arg Ile Asp Gly Ser Gly Gln
1030                1035                1040                1045 atg gcg att acc gtt gat gtt gaa gtg gcg agc gat aca ccg cat ccg     3643
Met Ala Ile Thr Val Asp Val Glu Val Ala Ser Asp Thr Pro His Pro
                1050                1055                1060 gcg cgg att ggc ctg aac tgc cag ctg gcg cag gta gca gag cgg gta     3691
Ala Arg Ile Gly Leu Asn Cys Gln Leu Ala Gln Val Ala Glu Arg Val
            1065                1070                1075 aac tgg ctc gga tta ggg ccg caa gaa aac tat ccc gac cgc ctt act     3739
Asn Trp Leu Gly Leu Gly Pro Gln Glu Asn Tyr Pro Asp Arg Leu Thr
            1080                1085                1090 gcc gcc tgt ttt gac cgc tgg gat ctg cca ttg tca gac atg tat acc     3787
Ala Ala Cys Phe Asp Arg Trp Asp Leu Pro Leu Ser Asp Met Tyr Thr
            1095                1100                1105 ccg tac gtc ttc ccg agc gaa aac ggt ctg cgc tgc ggg acg cgc gaa     3835
Pro Tyr Val Phe Pro Ser Glu Asn Gly Leu Arg Cys Gly Thr Arg Glu
1110                1115                1120                1125 ttg aat tat ggc cca cac cag tgg cgc ggc gac ttc cag ttc aac atc     3883
Leu Asn Tyr Gly Pro His Gln Trp Arg Gly Asp Phe Gln Phe Asn Ile
                1130                1135                1140 agc cgc tac agt caa cag caa ctg atg gaa acc agc cat cgc cat ctg     3931
Ser Arg Tyr Ser Gln Gln Gln Leu Met Glu Thr Ser His Arg His Leu
            1145                1150                1155 ctg cac gcg gaa gaa ggc aca tgg ctg aat atc gac ggt ttc cat atg     3979
Leu His Ala Glu Glu Gly Thr Trp Leu Asn Ile Asp Gly Phe His Met
            1160                1165                1170 ggg att ggt ggc gac gac tcc tgg agc ccg tca gta tcg gcg gaa ttt     4027
Gly Ile Gly Gly Asp Asp Ser Trp Ser Pro Ser Val Ser Ala Glu Phe
            1175                1180                1185 cag ctg agc gcc ggt cgc tac cat tac cag ttg gtc tgg tgt caa aaa     4075
Gln Leu Ser Ala Gly Arg Tyr His Tyr Gln Leu Val Trp Cys Gln Lys
1190                1195                1200                1205 taata ataaccgggc aggccatgtc tgcccgtatt tcgcgtaagg aaatccatta  4130
tgtactatcg atcagaccag ttttaatttt gtgtgtttcc atg                     4173
```

<210> SEQ ID NO 26
<211> LENGTH: 1205
<212> TYPE: PRT
<213> ORGANISM: Bacillus subtilis

<400> SEQUENCE: 26

```
Leu Gly His Tyr Ser His Ser Asp Ile Glu Glu Ala Val Lys Ser Ala
 1               5                  10                  15

Lys Lys Glu Gly Leu Lys Asp Tyr Leu Tyr Gln Glu Pro His Gly Lys
            20                  25                  30

Lys Arg Ser His Lys Ser His Arg Thr His Lys Lys Ser Arg Ser
        35                  40                  45

His Lys Lys Ser Tyr Cys Ser His Lys Lys Ser Arg Ser His Lys Lys
    50                  55                  60

Ser Phe Cys Ser His Lys Lys Ser Arg Ser His Lys Lys Ser Tyr Cys
 65                  70                  75                  80

Ser His Lys Lys Ser Arg Ser His Lys Lys Ser Tyr Arg Ser His Lys
                85                  90                  95

Lys Ser Arg Ser Tyr Lys Lys Ser Tyr Arg Ser Tyr Lys Lys Ser Arg
            100                 105                 110

Ser Tyr Lys Lys Ser Cys Arg Ser Tyr Lys Lys Ser Arg Ser Tyr Lys
        115                 120                 125

Lys Ser Tyr Cys Ser His Lys Lys Ser Arg Ser Tyr Lys Lys Ser
    130                 135                 140

Cys Arg Thr His Lys Lys Ser Tyr Arg Ser His Lys Lys Tyr Tyr Lys
145                 150                 155                 160

Lys Pro His His His Cys Asp Asp Tyr Lys Arg His Asp Asp Tyr Asp
                165                 170                 175

Ser Lys Lys Glu Tyr Trp Lys Asp Gly Asn Cys Trp Val Val Lys Lys
            180                 185                 190

Lys Tyr Lys Val Asp Arg Glu Asn Pro Gly Val Thr Gln Leu Asn Arg
        195                 200                 205

Leu Ala Ala His Pro Pro Phe Ala Ser Trp Arg Asn Ser Glu Glu Ala
    210                 215                 220

Arg Thr Asp Arg Pro Ser Gln Gln Leu Arg Ser Leu Asn Gly Glu Trp
225                 230                 235                 240

Arg Phe Ala Trp Phe Pro Ala Pro Glu Ala Val Pro Glu Ser Trp Leu
                245                 250                 255

Glu Cys Asp Leu Pro Glu Ala Asp Thr Val Val Pro Ser Asn Trp
            260                 265                 270

Gln Met His Gly Tyr Asp Ala Pro Ile Tyr Thr Asn Val Thr Tyr Pro
        275                 280                 285

Ile Thr Val Asn Pro Pro Phe Val Pro Thr Glu Asn Pro Thr Gly Cys
    290                 295                 300

Tyr Ser Leu Thr Phe Asn Val Asp Glu Ser Trp Leu Gln Glu Gly Gln
305                 310                 315                 320

Thr Arg Ile Ile Phe Asp Gly Val Asn Ser Ala Phe His Leu Trp Cys
                325                 330                 335

Asn Gly Arg Trp Val Gly Tyr Gly Gln Asp Ser Arg Leu Pro Ser Glu
            340                 345                 350

Phe Asp Leu Ser Ala Phe Leu Arg Ala Gly Glu Asn Arg Leu Ala Val
        355                 360                 365

Met Val Leu Arg Trp Ser Asp Gly Ser Tyr Leu Glu Asp Gln Asp Met
```

-continued

```
            370                 375                 380
Trp Arg Met Ser Gly Ile Phe Arg Asp Val Ser Leu Leu His Lys Pro
385                 390                 395                 400

Thr Thr Gln Ile Ser Asp Phe His Val Ala Thr Arg Phe Asn Asp Asp
                405                 410                 415

Phe Ser Arg Ala Val Leu Glu Ala Glu Val Gln Met Cys Gly Glu Leu
                420                 425                 430

Arg Asp Tyr Leu Arg Val Thr Val Ser Leu Trp Gln Gly Glu Thr Gln
                435                 440                 445

Val Ala Ser Gly Thr Ala Pro Phe Gly Gly Glu Ile Ile Asp Glu Arg
450                 455                 460

Gly Gly Tyr Ala Asp Arg Val Thr Leu Arg Leu Asn Val Glu Asn Pro
465                 470                 475                 480

Lys Leu Trp Ser Ala Glu Ile Pro Asn Leu Tyr Arg Ala Val Val Glu
                485                 490                 495

Leu His Thr Ala Asp Gly Thr Leu Ile Glu Ala Glu Ala Cys Asp Val
                500                 505                 510

Gly Phe Arg Glu Val Arg Ile Glu Asn Gly Leu Leu Leu Leu Asn Gly
                515                 520                 525

Lys Pro Leu Leu Ile Arg Gly Val Asn Arg His Glu His His Pro Leu
530                 535                 540

His Gly Gln Val Met Asp Glu Gln Thr Met Val Gln Asp Ile Leu Leu
545                 550                 555                 560

Met Lys Gln Asn Asn Phe Asn Ala Val Arg Cys Ser His Tyr Pro Asn
                565                 570                 575

His Pro Leu Trp Tyr Thr Leu Cys Asp Arg Tyr Gly Leu Tyr Val Val
                580                 585                 590

Asp Glu Ala Asn Ile Glu Thr His Gly Met Val Pro Met Asn Arg Leu
                595                 600                 605

Thr Asp Asp Pro Arg Trp Leu Pro Ala Met Ser Glu Arg Val Thr Arg
610                 615                 620

Met Val Gln Arg Asp Arg Asn His Pro Ser Val Ile Ile Trp Ser Leu
625                 630                 635                 640

Gly Asn Glu Ser Gly His Gly Ala Asn His Asp Ala Leu Tyr Arg Trp
                645                 650                 655

Ile Lys Ser Val Asp Pro Ser Arg Pro Val Gln Tyr Glu Gly Gly Gly
                660                 665                 670

Ala Asp Thr Thr Ala Thr Asp Ile Ile Cys Pro Met Tyr Ala Arg Val
                675                 680                 685

Asp Glu Asp Gln Pro Phe Pro Ala Val Pro Lys Trp Ser Ile Lys Lys
                690                 695                 700

Trp Leu Ser Leu Pro Gly Glu Thr Arg Pro Leu Ile Leu Cys Glu Tyr
705                 710                 715                 720

Ala His Ala Met Gly Asn Ser Leu Gly Gly Phe Ala Lys Tyr Trp Gln
                725                 730                 735

Ala Phe Arg Gln Tyr Pro Arg Leu Gln Gly Gly Phe Val Trp Asp Trp
                740                 745                 750

Val Asp Gln Ser Leu Ile Lys Tyr Asp Glu Asn Gly Asn Pro Trp Ser
                755                 760                 765

Ala Tyr Gly Gly Asp Phe Gly Asp Thr Pro Asn Asp Arg Gln Phe Cys
                770                 775                 780

Met Asn Gly Leu Val Phe Ala Asp Arg Thr Pro His Pro Ala Leu Thr
785                 790                 795                 800
```

```
Glu Ala Lys His Gln Gln Gln Phe Phe Gln Phe Arg Leu Ser Gly Gln
                805                 810                 815
Thr Ile Glu Val Thr Ser Glu Tyr Leu Phe Arg His Ser Asp Asn Glu
                820                 825                 830
Leu Leu His Trp Met Val Ala Leu Asp Gly Lys Pro Leu Ala Ser Gly
                835                 840                 845
Glu Val Pro Leu Asp Val Ala Pro Gln Gly Lys Gln Leu Ile Glu Leu
            850                 855                 860
Pro Glu Leu Pro Gln Pro Glu Ser Ala Gly Gln Leu Trp Leu Thr Val
865                 870                 875                 880
Arg Val Val Gln Pro Asn Ala Thr Ala Trp Ser Glu Ala Gly His Ile
                885                 890                 895
Ser Ala Trp Gln Gln Trp Arg Leu Ala Glu Asn Leu Ser Val Thr Leu
            900                 905                 910
Pro Ala Ala Ser His Ala Ile Pro His Leu Thr Thr Ser Glu Met Asp
            915                 920                 925
Phe Cys Ile Glu Leu Gly Asn Lys Arg Trp Gln Phe Asn Arg Gln Ser
    930                 935                 940
Gly Phe Leu Ser Gln Met Trp Ile Gly Asp Lys Lys Gln Leu Leu Thr
945                 950                 955                 960
Pro Leu Arg Asp Gln Phe Thr Arg Ala Pro Leu Asp Asn Asp Ile Gly
                965                 970                 975
Val Ser Glu Ala Thr Arg Ile Asp Pro Asn Ala Trp Val Glu Arg Trp
            980                 985                 990
Lys Ala Ala Gly His Tyr Gln Ala Glu Ala Ala Leu Leu Gln Cys Thr
            995                 1000                1005
Ala Asp Thr Leu Ala Asp Ala Val Leu Ile Thr Thr Ala His Ala Trp
        1010                1015                1020
Gln His Gln Gly Lys Thr Leu Phe Ile Ser Arg Lys Thr Tyr Arg Ile
1025                1030                1035                1040
Asp Gly Ser Gly Gln Met Ala Ile Thr Val Asp Val Glu Val Ala Ser
                1045                1050                1055
Asp Thr Pro His Pro Ala Arg Ile Gly Leu Asn Cys Gln Leu Ala Gln
            1060                1065                1070
Val Ala Glu Arg Val Asn Trp Leu Gly Leu Gly Pro Gln Glu Asn Tyr
        1075                1080                1085
Pro Asp Arg Leu Thr Ala Ala Cys Phe Asp Arg Trp Asp Leu Pro Leu
    1090                1095                1100
Ser Asp Met Tyr Thr Pro Tyr Val Phe Pro Ser Glu Asn Gly Leu Arg
1105                1110                1115                1120
Cys Gly Thr Arg Glu Leu Asn Tyr Gly Pro His Gln Trp Arg Gly Asp
                1125                1130                1135
Phe Gln Phe Asn Ile Ser Arg Tyr Ser Gln Gln Gln Leu Met Glu Thr
                1140                1145                1150
Ser His Arg His Leu Leu His Ala Glu Glu Gly Thr Trp Leu Asn Ile
            1155                1160                1165
Asp Gly Phe His Met Gly Ile Gly Gly Asp Asp Ser Trp Ser Pro Ser
        1170                1175                1180
Val Ser Ala Glu Phe Gln Leu Ser Ala Gly Arg Tyr His Tyr Gln Leu
1185                1190                1195                1200
Val Trp Cys Gln Lys
            1205
```

<210> SEQ ID NO 27
<211> LENGTH: 47
<212> TYPE: DNA
<213> ORGANISM: Artificial Sequence
<220> FEATURE:
<223> OTHER INFORMATION: cotG-linker 5' primer

<400> SEQUENCE: 27
ctattgctgc agtgaacccc cacctccttt gtatttcttt ttgacta                    47

<210> SEQ ID NO 28
<211> LENGTH: 49
<212> TYPE: DNA
<213> ORGANISM: Artificial Sequence
<220> FEATURE:
<223> OTHER INFORMATION: CMCase 5' primer

<400> SEQUENCE: 28
ggcatgctgc aggcatgcgc tagccgatcg gggacaaaaa cgccagtag                  49

<210> SEQ ID NO 29
<211> LENGTH: 24
<212> TYPE: DNA
<213> ORGANISM: Artificial Sequence
<220> FEATURE:
<223> OTHER INFORMATION: CMCase 3' primer

<400> SEQUENCE: 29
gccaaaaaaa agcttaacta attt                                             24

<210> SEQ ID NO 30
<211> LENGTH: 32
<212> TYPE: DNA
<213> ORGANISM: Artificial Sequence
<220> FEATURE:
<223> OTHER INFORMATION: levU 5' primer

<400> SEQUENCE: 30
aagtgcctgc agatgttgaa taaagcaggc at                                    32

<210> SEQ ID NO 31
<211> LENGTH: 32
<212> TYPE: DNA
<213> ORGANISM: Artificial Sequence
<220> FEATURE:
<223> OTHER INFORMATION: levU 3' primer

<400> SEQUENCE: 31
aatgaaaagc ttttatttat tcaataaaga ca                                    32

<210> SEQ ID NO 32
<211> LENGTH: 32
<212> TYPE: DNA
<213> ORGANISM: Artificial Sequence
<220> FEATURE:
<223> OTHER INFORMATION: tliA 5' primer

<400> SEQUENCE: 32
ctgcaggaat tcatgggtgt atttgactac aa                                    32

<210> SEQ ID NO 33
<211> LENGTH: 27
<212> TYPE: DNA
<213> ORGANISM: Artificial Sequence
<220> FEATURE:
<223> OTHER INFORMATION: tliA 3' primer

<400> SEQUENCE: 33
gaagcttgcg caaggaagac tgagatg                                                        27

<210> SEQ ID NO 34
<211> LENGTH: 2510
<212> TYPE: DNA
<213> ORGANISM: Bacillus subtilis
<220> FEATURE:
<221> NAME/KEY: CDS
<222> LOCATION: (461)..(2491)

<400> SEQUENCE: 34

```
ggatccagtg tccctagctc cgagaaaaaa tccagagaca atttgtttct catcaaggaa      60
gggtctttat actccgcatt taagtgaatc tctcgcgcgc cgcggaatgt tttcggctga     120
taaaaggaaa tatggtatga cttcttttg aagtctctga tatgtgatcc ccgataagcg      180
atatcaatat ccagcctttt tgatttacc ttcatcacag ctggcaccgg atcatcgtcc      240
catatatcct tttttaattc acgcaagtct tttggatgaa caaacagctg ataaagcggt     300
aaattggatt gattcttcat ccataatcct ccttacaaat tttaggcttt tatttttata    360
agatctcagc ggaacactta tacttttt aaaaccgcgc gtactatgag gtagtaagg       420 atcttcatcc ttaacatatt tttaaaagga ggatttcaaa ttg ggc cac tat tcc      475
                                              Leu Gly His Tyr Ser
                                                1               5 cat tct gac atc gaa gaa gcg gtg aaa tcc gca aaa aaa gaa ggt tta      523
His Ser Asp Ile Glu Glu Ala Val Lys Ser Ala Lys Lys Glu Gly Leu
         10                  15                  20 aag gat tat tta tac caa gag cct cat gga aaa aaa cgc agt cat aaa      571
Lys Asp Tyr Leu Tyr Gln Glu Pro His Gly Lys Lys Arg Ser His Lys
     25                  30                  35 aag tcg cac cgc act cac aaa aaa tct cgc agc cat aaa aaa tca tac      619
Lys Ser His Arg Thr His Lys Lys Ser Arg Ser His Lys Lys Ser Tyr
 40                  45                  50 tgc tct cac aaa aaa tct cgc agt cac aaa aaa tca ttc tgt tct cac      667
Cys Ser His Lys Lys Ser Arg Ser His Lys Lys Ser Phe Cys Ser His
                 55                  60                  65 aaa aaa tct cgc agc cac aaa aaa tca tac tgc tct cac aag aaa tct      715
Lys Lys Ser Arg Ser His Lys Lys Ser Tyr Cys Ser His Lys Lys Ser
             70                  75                  80                  85 cgc agc cac aaa aaa tcg tac cgt tct cac aaa aaa tct cgc agc tat      763
Arg Ser His Lys Lys Ser Tyr Arg Ser His Lys Lys Ser Arg Ser Tyr
                 90                  95                 100 aaa aaa tct tac cgt tct tac aaa aaa tct cgt agc tat aaa aaa tct      811
Lys Lys Ser Tyr Arg Ser Tyr Lys Lys Ser Arg Ser Tyr Lys Lys Ser
            105                 110                 115 tgc cgt tct tac aaa aaa tct cgc agc tac aaa aag tct tac tgt tct      859
Cys Arg Ser Tyr Lys Lys Ser Arg Ser Tyr Lys Lys Ser Tyr Cys Ser
        120                 125                 130 cac aag aaa aaa tct cgc agc tat aag aag tca tgc cgc aca cac aaa      907
His Lys Lys Lys Ser Arg Ser Tyr Lys Lys Ser Cys Arg Thr His Lys
    135                 140                 145 aaa tct tat cgt tcc cat aag aaa tac tac aaa aaa ccg cac cac cac      955
Lys Ser Tyr Arg Ser His Lys Lys Tyr Tyr Lys Lys Pro His His His
150                 155                 160                 165 tgc gac gac tac aaa aga cac gat gat tat gac agc aaa aaa gaa tac     1003
Cys Asp Asp Tyr Lys Arg His Asp Asp Tyr Asp Ser Lys Lys Glu Tyr
                170                 175                 180 tgg aaa gac ggc aat tgc tgg gta gtc aaa aag aaa tac aaa gga ggt     1051
```

```
                Trp Lys Asp Gly Asn Cys Trp Val Val Lys Lys Tyr Lys Gly Gly
                            185                 190                 195 ggg ggt tca ctg cag gca tgc gct agc cga tcg gga aca aaa acg cca        1099
Gly Gly Ser Leu Gln Ala Cys Ala Ser Arg Ser Gly Thr Lys Thr Pro
        200                 205                 210 gta gcc aag aat ggc cag ctt agc ata aaa ggt aca cag ctc gtt aac        1147
Val Ala Lys Asn Gly Gln Leu Ser Ile Lys Gly Thr Gln Leu Val Asn
    215                 220                 225 cga gac ggt aaa gcg gta cag ctg aag ggg atc agt tca cac gga ttg        1195
Arg Asp Gly Lys Ala Val Gln Leu Lys Gly Ile Ser Ser His Gly Leu
230                 235                 240                 245 caa tgg tat gga gaa tat gtc aat aaa gac agc tta aaa tgg ctg agg        1243
Gln Trp Tyr Gly Glu Tyr Val Asn Lys Asp Ser Leu Lys Trp Leu Arg
            250                 255                 260 gac gat tgg ggt atc acc gtt ttc cgt gca gcg atg tat acg gca gat        1291
Asp Asp Trp Gly Ile Thr Val Phe Arg Ala Ala Met Tyr Thr Ala Asp
                265                 270                 275 ggc ggt ata att gac aac ccg tcc gtg aaa aat aaa atg aaa gaa gcg        1339
Gly Gly Ile Ile Asp Asn Pro Ser Val Lys Asn Lys Met Lys Glu Ala
                    280                 285                 290 gtt gaa gcg gca aaa gag ctt ggg ata tat gtc atc att gac tgg cat        1387
Val Glu Ala Ala Lys Glu Leu Gly Ile Tyr Val Ile Ile Asp Trp His
295                 300                 305 atc tta aat gac ggt aat cca aac caa aat aaa gag aag gca aaa gaa        1435
Ile Leu Asn Asp Gly Asn Pro Asn Gln Asn Lys Glu Lys Ala Lys Glu
310                 315                 320                 325 ttc ttc aag gaa atg tca agc ctt tac gga aac acg cca aac gtc att        1483
Phe Phe Lys Glu Met Ser Ser Leu Tyr Gly Asn Thr Pro Asn Val Ile
                330                 335                 340 tat gaa att gca aac gaa cca aac ggt gat gtg aac tgg aag cgt gat        1531
Tyr Glu Ile Ala Asn Glu Pro Asn Gly Asp Val Asn Trp Lys Arg Asp
                345                 350                 355 att aaa ccg tat gcg gaa gaa gtg att tcc gtt atc cgc aaa aat gat        1579
Ile Lys Pro Tyr Ala Glu Glu Val Ile Ser Val Ile Arg Lys Asn Asp
            360                 365                 370 cca gac aac att atc att gtc gga acc ggt aca tgg agc cag gat gtg        1627
Pro Asp Asn Ile Ile Ile Val Gly Thr Gly Thr Trp Ser Gln Asp Val
375                 380                 385 aat gat gct gcc gat gac cag cta aaa gat gca aac gtt atg gac gca        1675
Asn Asp Ala Ala Asp Asp Gln Leu Lys Asp Ala Asn Val Met Asp Ala
390                 395                 400                 405 ctt cat ttt tat gcc ggc aca cac ggc caa ttt tta cgg gat aaa gca        1723
Leu His Phe Tyr Ala Gly Thr His Gly Gln Phe Leu Arg Asp Lys Ala
                410                 415                 420 aac tat gca ctc agc aaa gga gca cct att ttt gtg aca gag tgg gga        1771
Asn Tyr Ala Leu Ser Lys Gly Ala Pro Ile Phe Val Thr Glu Trp Gly
                425                 430                 435 aca agc gac gcg tct ggc aat ggc ggt gta ttc ctt gat caa tcg agg        1819
Thr Ser Asp Ala Ser Gly Asn Gly Gly Val Phe Leu Asp Gln Ser Arg
            440                 445                 450 gaa tgg ctg aaa tat ctc gac agc aag acc atc agc tgg gtg aac tgg        1867
Glu Trp Leu Lys Tyr Leu Asp Ser Lys Thr Ile Ser Trp Val Asn Trp
455                 460                 465 aat ctt tct gat aag cag gaa tca tcc tca gct tta aag ccg ggg gca        1915
Asn Leu Ser Asp Lys Gln Glu Ser Ser Ser Ala Leu Lys Pro Gly Ala
470                 475                 480                 485 tct aaa aca ggc ggc tgg cgg ttg tca gat tta tct gct tca gga aca        1963
Ser Lys Thr Gly Gly Trp Arg Leu Ser Asp Leu Ser Ala Ser Gly Thr
                490                 495                 500
```

```
ttc gtt aga gaa aac att ctc ggc acc aaa gat tcg acg aag gac att      2011
Phe Val Arg Glu Asn Ile Leu Gly Thr Lys Asp Ser Thr Lys Asp Ile
            505                 510                 515 cct gaa acg cca gca aaa gat aaa ccc aca cag gaa aac ggt att tct      2059
Pro Glu Thr Pro Ala Lys Asp Lys Pro Thr Gln Glu Asn Gly Ile Ser
520                 525                 530 gta caa tac aga gca ggg gat ggg agt atg aac agc aac caa atc cgt      2107
Val Gln Tyr Arg Ala Gly Asp Gly Ser Met Asn Ser Asn Gln Ile Arg
    535                 540                 545 ccg cag ctt caa ata aaa aat aac ggc aat acc acg gtt gat tta aaa      2155
Pro Gln Leu Gln Ile Lys Asn Asn Gly Asn Thr Thr Val Asp Leu Lys
550                 555                 560                 565 gat gtc act gcc cgt tac tgg tat aac gcg aaa aac aaa ggc caa aac      2203
Asp Val Thr Ala Arg Tyr Trp Tyr Asn Ala Lys Asn Lys Gly Gln Asn
                570                 575                 580 gtt gac tgt gac tac gcg cag ctt gga tgc ggc aat gtg aca tac aag      2251
Val Asp Cys Asp Tyr Ala Gln Leu Gly Cys Gly Asn Val Thr Tyr Lys
            585                 590                 595 ttt gtg acg ttg cat aaa cca aag caa ggt gca gat acc tat ctg gaa      2299
Phe Val Thr Leu His Lys Pro Lys Gln Gly Ala Asp Thr Tyr Leu Glu
        600                 605                 610 ctt gga ttt aaa aac gga acg ctg gca ccg gga gca agc aca ggg aat      2347
Leu Gly Phe Lys Asn Gly Thr Leu Ala Pro Gly Ala Ser Thr Gly Asn
    615                 620                 625 att cag ctt cgt ctt cac aat gat gac tgg agc aat tat gca caa agc      2395
Ile Gln Leu Arg Leu His Asn Asp Asp Trp Ser Asn Tyr Ala Gln Ser
630                 635                 640                 645 ggc gat tat tcc ttt ttc aaa tca aat acg ttt aaa aca acg aaa aaa      2443
Gly Asp Tyr Ser Phe Phe Lys Ser Asn Thr Phe Lys Thr Thr Lys Lys
                650                 655                 660 atc aca tta tat gat caa gga aaa ctg att tgg gga aca gaa cca aat      2491
Ile Thr Leu Tyr Asp Gln Gly Lys Leu Ile Trp Gly Thr Glu Pro Asn
            665                 670                 675 tagttaagc tttttttggc                                             2510

<210> SEQ ID NO 35
<211> LENGTH: 677
<212> TYPE: PRT
<213> ORGANISM: Bacillus subtilis

<400> SEQUENCE: 35

Leu Gly His Tyr Ser His Ser Asp Ile Glu Glu Ala Val Lys Ser Ala
1               5                   10                  15

Lys Lys Glu Gly Leu Lys Asp Tyr Leu Tyr Gln Glu Pro His Gly Lys
            20                  25                  30

Lys Arg Ser His Lys Ser His Arg Thr His Lys Lys Ser Arg Ser
        35                  40                  45

His Lys Lys Ser Tyr Cys Ser His Lys Ser Arg Ser His Lys Lys
    50                  55                  60

Ser Phe Cys Ser His Lys Lys Ser Arg Ser His Lys Lys Ser Tyr Cys
65                  70                  75                  80

Ser His Lys Lys Ser Arg Ser His Lys Lys Ser Tyr Arg Ser His Lys
                85                  90                  95

Lys Ser Arg Ser Tyr Lys Ser Tyr Arg Ser Tyr Lys Lys Ser Arg
            100                 105                 110

Ser Tyr Lys Lys Ser Cys Arg Ser Tyr Lys Lys Ser Arg Ser Tyr Lys
        115                 120                 125

Lys Ser Tyr Cys Ser His Lys Lys Lys Ser Arg Ser Tyr Lys Lys Ser
```

-continued

```
            130                 135                 140
Cys Arg Thr His Lys Lys Ser Tyr Arg Ser His Lys Lys Tyr Tyr Lys
145                 150                 155                 160

Lys Pro His His His Cys Asp Asp Tyr Lys Arg His Asp Asp Tyr Asp
                165                 170                 175

Ser Lys Lys Glu Tyr Trp Lys Asp Gly Asn Cys Trp Val Val Lys Lys
            180                 185                 190

Lys Tyr Lys Gly Gly Gly Ser Leu Gln Ala Cys Ala Ser Arg Ser
            195                 200                 205

Gly Thr Lys Thr Pro Val Ala Lys Asn Gly Gln Leu Ser Ile Lys Gly
210                 215                 220

Thr Gln Leu Val Asn Arg Asp Gly Lys Ala Val Gln Leu Lys Gly Ile
225                 230                 235                 240

Ser Ser His Gly Leu Gln Trp Tyr Gly Glu Tyr Val Asn Lys Asp Ser
                245                 250                 255

Leu Lys Trp Leu Arg Asp Asp Trp Gly Ile Thr Val Phe Arg Ala Ala
            260                 265                 270

Met Tyr Thr Ala Asp Gly Gly Ile Ile Asp Asn Pro Ser Val Lys Asn
            275                 280                 285

Lys Met Lys Glu Ala Val Glu Ala Ala Lys Glu Leu Gly Ile Tyr Val
290                 295                 300

Ile Ile Asp Trp His Ile Leu Asn Asp Gly Asn Pro Asn Gln Asn Lys
305                 310                 315                 320

Glu Lys Ala Lys Glu Phe Phe Lys Glu Met Ser Ser Leu Tyr Gly Asn
                325                 330                 335

Thr Pro Asn Val Ile Tyr Glu Ile Ala Asn Glu Pro Asn Gly Asp Val
            340                 345                 350

Asn Trp Lys Arg Asp Ile Lys Pro Tyr Ala Glu Glu Val Ile Ser Val
            355                 360                 365

Ile Arg Lys Asn Asp Pro Asn Ile Ile Ile Val Gly Thr Gly Thr
370                 375                 380

Trp Ser Gln Asp Val Asn Asp Ala Ala Asp Gln Leu Lys Asp Ala
385                 390                 395                 400

Asn Val Met Asp Ala Leu His Phe Tyr Ala Gly Thr His Gly Gln Phe
                405                 410                 415

Leu Arg Asp Lys Ala Asn Tyr Ala Leu Ser Lys Gly Ala Pro Ile Phe
            420                 425                 430

Val Thr Glu Trp Gly Thr Ser Asp Ala Ser Gly Asn Gly Val Phe
            435                 440                 445

Leu Asp Gln Ser Arg Glu Trp Leu Lys Tyr Leu Asp Ser Lys Thr Ile
450                 455                 460

Ser Trp Val Asn Trp Asn Leu Ser Asp Lys Gln Glu Ser Ser Ala
465                 470                 475                 480

Leu Lys Pro Gly Ala Ser Lys Thr Gly Gly Trp Arg Leu Ser Asp Leu
                485                 490                 495

Ser Ala Ser Gly Thr Phe Val Arg Glu Asn Ile Leu Gly Thr Lys Asp
            500                 505                 510

Ser Thr Lys Asp Ile Pro Glu Thr Pro Ala Lys Asp Lys Pro Thr Gln
            515                 520                 525

Glu Asn Gly Ile Ser Val Gln Tyr Arg Ala Gly Asp Gly Ser Met Asn
530                 535                 540

Ser Asn Gln Ile Arg Pro Gln Leu Gln Ile Lys Asn Asn Gly Asn Thr
545                 550                 555                 560
```

-continued

```
Thr Val Asp Leu Lys Asp Val Thr Ala Arg Tyr Trp Tyr Asn Ala Lys
            565                 570                 575
Asn Lys Gly Gln Asn Val Asp Cys Asp Tyr Ala Gln Leu Gly Cys Gly
        580                 585                 590
Asn Val Thr Tyr Lys Phe Val Thr Leu His Lys Pro Lys Gln Gly Ala
    595                 600                 605
Asp Thr Tyr Leu Glu Leu Gly Phe Lys Asn Gly Thr Leu Ala Pro Gly
610                 615                 620
Ala Ser Thr Gly Asn Ile Gln Leu Arg Leu His Asn Asp Asp Trp Ser
625                 630                 635                 640
Asn Tyr Ala Gln Ser Gly Asp Tyr Ser Phe Phe Lys Ser Asn Thr Phe
                645                 650                 655
Lys Thr Thr Lys Lys Ile Thr Leu Tyr Asp Gln Gly Lys Leu Ile Trp
            660                 665                 670
Gly Thr Glu Pro Asn
        675

<210> SEQ ID NO 36
<211> LENGTH: 24
<212> TYPE: PRT
<213> ORGANISM: Hepatitis B virus

<400> SEQUENCE: 36

Met Gln Trp Asn Ser Thr Thr Phe His Leu Gln Asp Pro Arg Val Arg
 1               5                  10                  15
Gly Leu Tyr Phe Pro Ala Gly Gly
            20

<210> SEQ ID NO 37
<211> LENGTH: 30
<212> TYPE: DNA
<213> ORGANISM: Artificial Sequence
<220> FEATURE:
<223> OTHER INFORMATION: Fv 5' primer

<400> SEQUENCE: 37
gaggctagct cgactgagga gtctggagga                                      30

<210> SEQ ID NO 38
<211> LENGTH: 30
<212> TYPE: DNA
<213> ORGANISM: Artificial Sequence
<220> FEATURE:
<223> OTHER INFORMATION: Fv 3' primer

<400> SEQUENCE: 38
ggagggccct taacgtttta tttccaggta                                      30

<210> SEQ ID NO 39
<211> LENGTH: 29
<212> TYPE: DNA
<213> ORGANISM: Artificial Sequence
<220> FEATURE:
<223> OTHER INFORMATION: egfp 5' primer

<400> SEQUENCE: 39
cggctagcgc tatggtgagc aagggcgag                                       29

<210> SEQ ID NO 40
<211> LENGTH: 32
<212> TYPE: DNA
```

```
<213> ORGANISM: Artificial Sequence
<220> FEATURE:
<223> OTHER INFORMATION: egfp 3' primer

<400> SEQUENCE: 40
gcgggcccaa gcttttactt gtacagctcg tc                              32

<210> SEQ ID NO 41
<211> LENGTH: 32
<212> TYPE: DNA
<213> ORGANISM: Artificial Sequence
<220> FEATURE:
<223> OTHER INFORMATION: gfpuv 5' primer

<400> SEQUENCE: 41
gcggatccct gcagatgagt aaaggagaag aa                              32

<210> SEQ ID NO 42
<211> LENGTH: 32
<212> TYPE: DNA
<213> ORGANISM: Artificial Sequence
<220> FEATURE:
<223> OTHER INFORMATION: gfpuv 3' primer

<400> SEQUENCE: 42
cgaagcttga attcttattt gtagagctca tc                              32
```